US012751914B2

(12) United States Patent
DeSimone et al.

(10) Patent No.: US 12,751,914 B2
(45) Date of Patent: Oct. 6, 2026

(54) POLYMERIC MICROSTRUCTURES AND SYSTEMS AND METHODS FOR MAKING SAME

(71) Applicants: The Board of Trustees of the Leland Stanford Junior University, Stanford, CA (US); The University of North Carolina at Chapel Hill, Chapel Hill, NC (US)

(72) Inventors: Joseph M. DeSimone, Stanford, CA (US); Gunilla B. Jacobson, Stanford, CA (US); Maria T. Dulay, Stanford, CA (US); Brian J. Lee, Stanford, CA (US); Kai-Wen Hsiao, Stanford, CA (US); Netra Rajesh, Stanford, CA (US); Madison M. Driskill, Stanford, CA (US); Audrey Shih, Stanford, CA (US); Jillian Perry, Durham, NC (US); Shaomin Tian, Chapel Hill, NC (US)

(73) Assignees: The Board of Trustees of the Leland Stanford Junior University, Stanford, CA (US); The University of North Carolina at Chapel Hill, Chapel Hill, NC (US)

( * ) Notice: Subject to any disclaimer, the term of this patent is extended or adjusted under 35 U.S.C. 154(b) by 312 days.

(21) Appl. No.: 18/693,904

(22) PCT Filed: Sep. 22, 2022

(86) PCT No.: PCT/US2022/044393

§ 371 (c)(1),
(2) Date: Mar. 20, 2024

(87) PCT Pub. No.: WO2023/049267

PCT Pub. Date: Mar. 30, 2023

(65) Prior Publication Data

US 2024/0382413 A1 Nov. 21, 2024

Related U.S. Application Data

(60) Provisional application No. 63/248,280, filed on Sep. 24, 2021.

(51) Int. Cl.
*A61K 9/00* (2006.01)
*B29C 64/135* (2017.01)
(Continued)

(52) U.S. Cl.
CPC .......... *A61K 9/0021* (2013.01); *B29C 64/135* (2017.08); *B29C 64/232* (2017.08);
(Continued)

(58) Field of Classification Search
CPC .............. A61M 37/00; A61M 37/0015; A61M 2037/0023; A61M 2037/003;
(Continued)

(56) References Cited

U.S. PATENT DOCUMENTS

| | | | |
|---|---|---|---|
| 6,537,242 | B1 | 3/2003 | Palmer |
| 9,216,546 | B2 | 12/2015 | DeSimone et al. |

(Continued)

FOREIGN PATENT DOCUMENTS

| | | | |
|---|---|---|---|
| CN | 106976232 | A | 7/2017 |
| CN | 112641931 | A | 4/2021 |

(Continued)

OTHER PUBLICATIONS

Lipkowitz et al., Injection continuous liquid interface production of 3D objects, Sci. Adv. 8, eabq3917 (2022).

(Continued)

*Primary Examiner* — Dung T Ulsh
(74) *Attorney, Agent, or Firm* — Bret E. Field; Bozicevic, Field & Francis LLP

(57) ABSTRACT

Aspects of the present disclosure include polymeric structures (e.g., microneedles) having a lattice microstructure composed of one or more lattice cell units. Polymeric structures according to certain embodiments have repeating lattice cell units that are formed by high resolution continuous liquid interface production. Aspects also include systems for making polymeric structures having a lattice microstructure. Systems according to certain embodiments include a micro-digital light projection system having a light (Continued)

beam generator component and a light projection monitoring component and a liquid interface polymerization module having a build elevator and a build surface configured for generating the polymeric lattice microstructure from a polymerizable composition positioned therebetween. Methods for making polymeric structures having a lattice microstructure with the subject systems are also provided. Patches having an array of polymeric microneedles for applying to a skin surface of a subject are also described. In some embodiments, patches include microneedles that contain an active agent compound (e.g., an immunogenic active agent). Methods for applying the patches to the skin surface of a subject are also described.

14 Claims, 35 Drawing Sheets

(51) Int. Cl.

| | |
|---|---|
| ***B29C 64/232*** | (2017.01) |
| ***B29C 64/255*** | (2017.01) |
| ***B29C 64/268*** | (2017.01) |
| ***B29K 23/00*** | (2006.01) |
| ***B29L 31/00*** | (2006.01) |
| ***B33Y 10/00*** | (2015.01) |
| ***B33Y 30/00*** | (2015.01) |
| ***B33Y 70/00*** | (2020.01) |
| ***B33Y 80/00*** | (2015.01) |
| ***C08F 122/10*** | (2006.01) |

(52) U.S. Cl.

CPC ............ *B29C 64/268* (2017.08); *B33Y 10/00* (2014.12); *B33Y 30/00* (2014.12); *B33Y 70/00* (2014.12); *B33Y 80/00* (2014.12); *C08F 122/1006* (2020.02); *B29C 64/255* (2017.08); *B29K 2023/08* (2013.01); *B29L 2031/7544* (2013.01)

(58) Field of Classification Search

CPC .. A61M 2037/0038; A61M 2037/0046; A61M 2037/0053; A61M 2037/0061

See application file for complete search history.

(56) References Cited

U.S. PATENT DOCUMENTS

| | | | | |
|---|---|---|---|---|
| 10,155,882 | B2 | 12/2018 | Rolland et al. | |
| 10,232,605 | B2 | 3/2019 | DeSimone et al. | |
| 10,618,215 | B2 | 4/2020 | DeSimone et al. | |
| 2002/0171178 | A1 | 11/2002 | Dean et al. | |
| 2008/0183144 | A1 | 7/2008 | Trautman et al. | |
| 2010/0305473 | A1* | 12/2010 | Yuzhakov ......... | A61M 37/0015 604/173 |
| 2012/0105534 | A1 | 5/2012 | Boday et al. | |
| 2015/0102532 | A1 | 4/2015 | DeSimone et al. | |
| 2017/0095972 | A1 | 4/2017 | DeSimone et al. | |
| 2018/0064920 | A1* | 3/2018 | Desimone ......... | A61M 37/0015 |
| 2018/0326193 | A1 | 11/2018 | Kobayashi | |
| 2020/0179123 | A1* | 6/2020 | Steinmann ................ | A61F 2/34 |
| 2020/0384695 | A1 | 12/2020 | Mardjono et al. | |
| 2021/0031439 | A1 | 2/2021 | Desimone et al. | |
| 2021/0246252 | A1 | 8/2021 | Poelma et al. | |
| 2022/0080171 | A1 | 3/2022 | Yoshida et al. | |
| 2023/0321419 | A1 | 10/2023 | Khademhosseini et al. | |
| 2025/0178280 | A1 | 6/2025 | Lipkowitz et al. | |
| 2025/0186754 | A1 | 6/2025 | DeSimone et al. | |

FOREIGN PATENT DOCUMENTS

| | | | |
|---|---|---|---|
| EP | 3137125 | B1 | 3/2020 |
| EP | 3766670 | A1 | 1/2021 |
| WO | WO2014126837 | A1 | 8/2014 |
| WO | WO2016145050 | A1 | 9/2016 |
| WO | WO2017112521 | A1 | 6/2017 |
| WO | WO2017210298 | A1 | 12/2017 |
| WO | WO2019089596 | A1 | 5/2019 |
| WO | WO2020184909 | A1 | 9/2020 |
| WO | WO2023205341 | A1 | 10/2023 |
| WO | WO2024086096 | A1 | 4/2024 |
| WO | WO2024227075 | A1 | 10/2024 |

OTHER PUBLICATIONS

Tumbleston et al., Continuous liquid interface production of 3D objects, Science, 347(6228):1349-1352 (2015).

Ge et al., Projection micro stereolithography based 3D printing and its applications, Int. J. Extrem. Manuf. vol. 2, Issue 2, pp. 022004 (19pp), Jun. 4, 2020.

* cited by examiner

1.5-μm-resolution

Resolution characterization: Line pattern, Square array, Hole pattern

Print dimension extraction from SEM

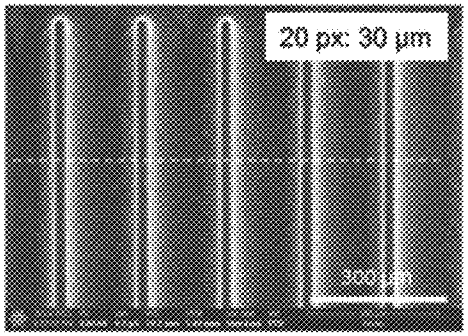

Extract the distance between peaks

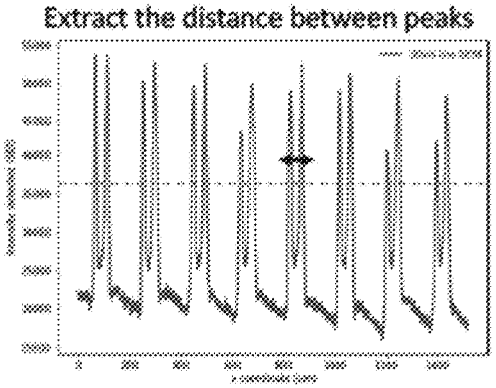

Square array (60 pixels)

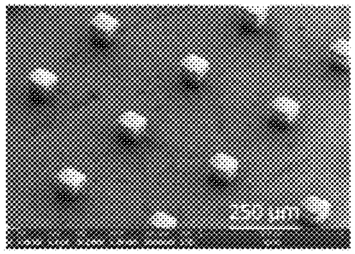

Hole array (30 pixels)

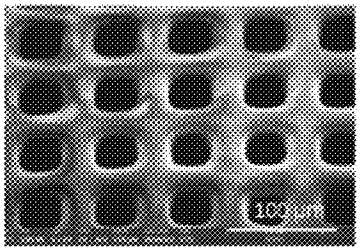

Hole array (25 pixels)

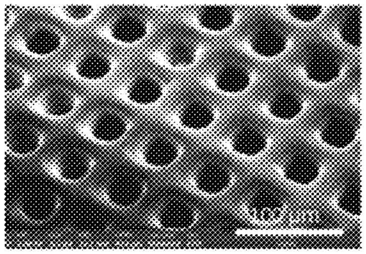

Summary Table : Resolution Characterization (1.5 μm CLIP)

| Pattern | Design width | | Measured width | μm/pixel |
|---|---|---|---|---|
| Line | 135 μm | 90 pixels | 138.97 μm ± 1.84 μm | 1.54 μm |
| | 30 μm | 20 pixels | 30.98 μm ± 2.97 μm | 1.54 μm |
| | 15 μm | 10 pixels | 13.62 μm ± 0.71 μm | 1.36 μm |
| | 7.5 μm | 5 pixels | 7.18 μm ± 1.87 μm | 1.43 μm |
| | 6 μm | 4 pixels | 4.63 μm ± 0.51 μm | 1.15 μm |
| | 4.5 μm | 3 pixels | 3.37 μm ± 0.45 μm | 1.12 μm |
| Hole | 45 μm | 30 pixels | 34.76 μm ± 1.48 μm | 1.15 μm |
| | 25 μm | 25 pixels | 27.85 μm ± 2.28 μm | 1.11 μm |
| | 20 μm | 20 pixels | 14.84 μm ± 3.45 μm | 0.72 μm |
| Square | 90 μm | 60 pixels | 88.57 μm ± 3.80 μm | 1.47 μm |

FIG. 2B 1.5-µm-resolution

| CLIP Printers (@ Stanford) | | Pixel size (µm x µm) | Build area (mm x mm) |
|---|---|---|---|
| **Carbon L1** | | 160 x 160 | 400 x 250 |
| **Carbon M2** | | 75 x 75 | 190 x 120 |
| **3DLP9000** | 30 µm projection lens | 30 x 30 | 77 x 48 |
| **Light engine** (Digital Light Innovations) | Native (No lens) | 7.45 x 7.45 | 19.1 x 11.9 |
| | 2x microscope objective | 3.7 x 3.7 | 9.5 x 6.0 |
| | 5x microscope objective | 1.5 x 1.5 | 3.8 x 2.4 |

Parameters

| Parameter | Value | Units | Source |
|---|---|---|---|
| $k_p$ | 15 | $m^3/(mol\ s)$ | [50] |
| $k_t$ | 3500 | $m^3/(mol\ s)$ | [50] |
| $k_o$ | $2 \times 10^5$ | $m^3/(mol\ s)$ | [49] |
| $D_o$ | $3.5 \times 10^{-11}$ | $m^2/s$ | [51] |
| H | $10 \times 10^4$ | m | Estimated |
| $I_o$ | 1.0 | $E/(m^2\ s)$ | Estimated |
| [PI] | 60 | $mol/m^3$ | Measured |
| e | 1.3 | $m^3/(mol\ m)$ | [52] |
| $[O_{2,eqb}]$ | 4.5 | $mol/m^3$ | [53][54] |
| $f$ | 0.6 | - | [52] |

| | Print time | Print height |
|---|---|---|
| This work | 1.5 hour | 2000 μm |
| NanoScribe | 48 hour + | 0.2 μm |

*Minimum feature size: 100 mm

Sample image at position 150 mm

Feature detection on all slanted edges

Full field edge profile extraction

Create average sampling of edges

POLYMERIC MICROSTRUCTURES AND SYSTEMS AND METHODS FOR MAKING SAME

CROSS-REFERENCE TO RELATED APPLICATIONS

This application is a U.S. National Stage Application of PCT Application No. PCT/US2022/044393 filed Sep. 22, 2022, which application, pursuant to 35 U.S.C. § 119 (e), claims priority to the filing date of U.S. Provisional Patent Application Ser. No. 63/248,280 filed Sep. 24, 2021; the disclosures of which applications are incorporated herein by reference in their entirety.

INTRODUCTION

The intradermal (ID) space has been actively explored as a means for drug delivery and diagnostics that are minimally invasive. Intradermal drug delivery is the process of delivering formulations into layers of skin. ID access necessitates puncturing the outermost layer of skin called the stratum corneum (StC), a tough barrier that provides mechanical integrity for the skin. Human skin is a complex, multi-layer organ, that includes the stratum corneum, epidermis, dermis and hypodermis. Often, these treatments target either the epidermal or dermal layers of skin, which are situated above blood vessels and nerve fibers of the skin. It offers an attractive alternative to intravenous (IV) injection, which often elicits systemic effects and can be particularly advantageous for targeted, local drug delivery. ID drug delivery can provide for the ability to deliver compounds with a significant first-pass effect, or metabolization by the liver which can prematurely degrade the therapeutic compound, upon systemic administration. Further, ID access also reduces pain associated with hypodermic injections and can help eliminate the risk of transmitting blood-borne diseases through the generation of dangerous medical waste. ID access can also be self-administered and can eliminate reliance on trained medical professionals.

Microneedles or microneedle patches or Micro-Array Patches (MAPs) are comprised of a series of micrometer-sized projections that can painlessly puncture the skin and access the epidermal/dermal layer. MAPs are employed in cosmetics, such as for use in treating acne scars and stretch marks by penetrating the stratum corneum to create micro conduits that stimulate growth factor secretion and collagen production. Microneedles are generally fabricated by a three-step process master fabrication, mold fabrication and mold filling to generate hollow, metallic projections with uniform geometries. Microneedles have been generally manufactured to be produced in a manner like conventional hypodermic needles.

SUMMARY

Aspects of the present disclosure include polymeric structures (e.g., microneedles) having a lattice microstructure composed of one or more lattice cell units. Polymeric structures according to certain embodiments have repeating lattice cell units that are formed by high resolution continuous liquid interface production. Aspects also include systems for making polymeric structures having a lattice microstructure. Systems according to certain embodiments include a micro-digital light projection system having a light beam generator component and a light projection monitoring component and a liquid interface polymerization module having a build elevator and a build surface configured for generating the polymeric lattice microstructure from a polymerizable composition positioned therebetween. Methods for making polymeric structures having a lattice microstructure with the subject systems are also provided. Patches having an array of polymeric microneedles for applying to a skin surface of a subject are also described. In some embodiments, patches include microneedles that contain an active agent compound (e.g., an immunogenic active agent). Methods for applying the patches to the skin surface of a subject are also described.

In some embodiments, the lattice microstructures of the polymeric structures described herein have 2 or more repeating lattice cell units, such as 5 or more repeating lattice cell units. In certain embodiments, the lattice microstructure has a gradient in the lattice cell units such that the density of lattice cell units increases across a longitudinal axis of the polymeric structure. In some embodiments, the lattice cell unit has a lattice shape that is tetrahedral, Kagome, rhombic, icosahedral, Voronoi or triangular. In embodiments, the lattice cells have a unit size of from 10 μm to 1000 μm, such as from 200 μm to 500 μm. In some embodiments, the lattice microstructure includes a plurality of struts. In some instances, the struts have a thickness of from 25 μm to 150 μm, such as from 50 μm to 100 μm, for example 70 μm to 90 μm. Polymeric structures having a lattice microstructure of interest may have a length of from 500 μm to 2000 μm, such as from 700 μm to 1200 μm. In some embodiments, the lattice microstructure has a volume of from 0.01 μL to 2 μL. In embodiments, the polymeric structure is formed from a polymerizable material such as polycaprolactone, polyalycolic acid, polylactic acid, polylactic-co-glycolic acid, polyethylene glycol, thiol-enes, anhydrides, polyacrylic acid, poly methylmethacrylate, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof. In certain embodiments, the polymeric structure is formed from polyethylene glycol dimethacrylate (PEGDMA). In some instances, the polymerizable material is biodegradable. In some instances, the polymeric structure is dissolvable in an aqueous medium.

In some embodiments, polymeric structures described herein are polymeric microneedles having a lattice microstructure with one or more lattice cell units. In certain embodiments, the lattice microstructures of the polymeric microneedles have 2 or more repeating lattice cell units. In certain embodiments, the lattice microstructure of the polymeric microneedle has a gradient in the lattice cell units such that the density of lattice cell units increases across a longitudinal axis of the microneedle. In some embodiments, the lattice cell unit has a lattice shape that is tetrahedral, Kagome, rhombic, icosahedral, Voronoi or triangular. In embodiments, the lattice cells have a unit size of from 10 μm to 1000 μm, such as from 200 μm to 500 μm. In some embodiments, the lattice microstructure includes a plurality of struts. In some instances, the struts have a thickness of from 25 μm to 150 μm, such as from 50 μm to 100 μm, for example 70 μm to 90 μm. Polymeric structures having a lattice microstructure of interest may have a length of from 500 μm to 2000 μm, such as from 700 μm to 1200 μm. In some embodiments, the lattice microstructure has a volume of from 0.01 μL to 2 μL. In some embodiments, the microneedle has a square pyramidal shape. In other embodiments, the microneedle has a conical projection shape. In yet other embodiments, the microneedle has an obelisk projection shape. In some embodiments, the microneedle includes a tip section comprising a solid structure, a body section comprising a lattice structure and a base section comprising a solid structure. In these embodiments, the tip section may be a length of from 25 μm to 500 μm, such as from 50 μm to 300 μm. In some instances, the microneedle has a tip diameter of from 0.1 μm to 10 μm. In some embodiments, the body section has a length of from 50 μm to 1000 μm, such as from 50 μm to 300 μm. In some embodiments, the base section has a length of from 25 μm to 500 μm, such as from 50 μm to 300 μm. In certain embodiments, the body section has a lattice microstructure has a gradient in the lattice cell unit density that increases across a longitudinal axis of the body section of the microneedle.

In certain embodiments, polymeric microneedles described herein are dynamic microneedles which can alter geometry or shape in response to an applied stimulus. In certain embodiments, the stimulus is applied mechanical pressure (e.g., pressure when inserted through a skin surface of a subject). In some instances, the dynamic microneedle is compliant and exhibits motion through elastic deformation of the polymeric microstructure. In some embodiments, the microneedle deploys a barb structure in response to the applied stimulus.

In embodiments, polymeric microneedles are formed from a polymerizable material. In some instances, the polymeric microneedle is biodegradable. In some instances, the polymeric microneedle is dissolvable in aqueous medium, such as when applied intradermally to a subject.

Aspects of the disclosure also include patches having a backing layer and a plurality of polymeric microneedles in contact with the backing layer where each microneedle includes a lattice microstructure having one or more lattice cell units. In some embodiments, the plurality of microneedles form an array of microneedles on the backing layer. In some instances, the microneedles are separated from each other on the backing layer by an average distance of from 5 μm to 1000 μm, such as from 100 μm to 500 μm. Patches may include microneedles having different lattice shapes such as where the patch include one or more microneedles with a lattice microstructure having a tetrahedral lattice shape, one or more microneedles with a lattice microstructure having a Kagome lattice shape, one or more microneedles with a lattice microstructure having a rhombic lattice shape, one or more microneedles with a lattice microstructure having an icosahedral lattice shape, one or more microneedles with a lattice microstructure having a Voronoi lattice shape or one or more microneedles with a lattice microstructure having a triangular lattice shape. In some instances, patches have microneedles that have 2 or more different lattice shapes, such as 3 or more different lattice shapes. In certain instances, one or more of the microneedles of the patch have different lengths or different base widths. In certain embodiments, one or more of the microneedles of the patch have different mechanical integrity (e.g., can withstand different load bearings). In certain embodiments, patches of interest include one or more dynamic microneedles, such as one or more microneedles which can alter geometry or shape, one or more microneedles which exhibit motion through elastic deformation or one or more microneedles which deploy a barb structure. In certain embodiments, patches of interest include a pressure sensitive adhesive, such as for maintaining the patch in contact with the skin surface of a subject for an extended period of time.

In certain embodiments, polymeric microneedles also include an active agent compound. In some instances, the active agent compound is coated onto one or more surfaces of the microneedle. In some instances, the active agent compound is coated onto a tip section of the microneedle. In some instances, the active agent compound is coated onto a body section of the microneedle. In some instances, the active agent compound is coated onto a base section of the microneedle. In some embodiments, the active agent compound is contained within the lattice microstructure of the polymeric microneedle. In some embodiments, the active agent compound fills 1% or more of the void volume of the lattice microstructure, such as 10% or more, such as 25% or more and including 50% or more of the void volume of the lattice microstructure. In some embodiments, each polymeric microneedle contains 0.01 μL or more of the active agent, such as 0.05 μL or more and including 0.1 μL or more of the active agent. The active agent compound in some instances is a small molecule active agent. In other instances, the active agent is an immunogenic active agent, such as a vaccine.

Aspects of the present disclosure also include methods for applying a patch having a plurality of polymeric microneedles to a skin surface of a subject. In some instances, the patch includes microneedles arranged in an array on a backing layer. In certain instances, the patch is applied to the skin surface of the subject and maintained in contact with the subject for an extended period of time, such as for 30 minutes or longer, such as 1 hour or longer and including for 6 hours or longer. In certain instances, the patch is applied to the skin surface of the subject and removed within 15 minutes or less, such as within 5 minutes or less and including within 1 minute or less.

In some embodiments, methods include applying the patch to deliver a therapeutically effective amount of an active agent compound to the subject. In these embodiments, the plurality of polymeric microneedles contain an active agent compound and the patch is maintained in contact with the subject for a period of time sufficient to deliver one or more doses of the active agent compounds, such 2 or more doses and include 5 or more doses. In certain cases, some instances, the patch is maintained in contact with the subject for sustained release of the active agent to the subject over a period of time. In some instances, methods include applying the patch to the skin surface of the subject in a manner sufficient to collect a biological fluid sample from the subject into the microneedles. In some embodiments, methods include collecting interstitial fluid from the subject into the microneedles. In other embodiments, methods include collecting dermal fluid from the subject into the microneedles. Methods according to certain instances, include collecting 0.01 μL to 250 μL of the biological fluid from the subject, such as from 0.01 μL to 2 μL. In some embodiments, methods include collecting a biological fluid sample from the subject (e.g., interstitial fluid, dermal fluid) for detecting an analyte present in the biological sample, such as for detecting glucose.

Aspects of the present disclosure also include systems for making a polymeric structure having a lattice microstructure with one or more lattice cell units, such as a polymeric microneedle. Systems according to certain embodiments include a micro-digital light projection system having a light beam generator component and a light projection monitoring component and a liquid interface polymerization module that includes a build elevator and a build surface configured for generating the lattice microstructure from a polymerizable composition positioned therebetween. In some embodiments, the light beam generator component includes a light source, a tube lens and one or more projection lenses. In some instances, the light beam generator component includes a digital micromirror device. For instance, the light beam generator may include two or more projection lenses, such as where one or more of the projection lenses is a magnification lens (e.g., a 2-fold or more magnification lens). In some embodiments, the light source is a laser. In other embodiments, the light source is a light emitting diode. In some instances, the light source is a continuous light source. In other instances, the light source is configured to emit light in predetermined intervals, such as a stroboscopic light source. In some embodiments, the light beam generator component is configured to generate light sheets, such as light sheets having a predetermined optical pattern. In some embodiments, the light projection monitoring component includes a photodetector. In some instances, the photodetector includes a charged-coupled device (CCD).

In some embodiments, systems also include a processor having memory operably coupled to the processor where the memory includes instructions stored thereon, which when executed by the processor, cause the processor to irradiate a polymerizable composition positioned between a build elevator and a build surface to generate a polymerizable composition having a first polymerized region of the polymerizable composition in contact with the build elevator and a first non-polymerized region of the polymerizable composition in contact with the build surface; displace the build elevator away from the build surface; irradiate the first non-polymerized region of the polymerizable composition to generate a second polymerized region of the polymerizable composition in contact with the first polymerized region and a second non-polymerized region in contact with the build surface. These steps are repeated in a manner sufficient to generate the polymer microstructure having a lattice microstructure. In some embodiments, the memory includes instructions to irradiate the polymerizable composition for a duration sufficient to bond the first polymerized region of the polymerizable composition to the build elevator. In some embodiments, the memory includes instructions to displace the build elevator in predetermined increments of from 0.5 μm to 1.0 μm. In some embodiments, systems also include a source of the polymerizable composition. In some instances, the source is configured to continuously deliver polymerizable composition to the build surface. In some instances, the system is configured to add polymerizable composition to the build surface after each displacement of the build elevator away from the build surface. In some embodiments, the light source is configured to irradiate through the build surface. In some instances, at least a part of the build surface is permeable to a polymerization inhibitor, such as where the polymerization inhibitor is oxygen.

In some embodiments, the memory includes instructions to determine a focal plane on the build surface from the micro-digital light projection system. In some instances, the memory includes instructions to determine the focal plane by irradiating the build surface with a stroboscopic light source through the tube lens and displacing the build surface until the light is focused on the build surface through the tube lens. In some instances, the memory includes instructions to irradiate the build surface with a plane of light having a projected image pattern with the stroboscopic light source. In some embodiments, the memory includes instructions to displace the build surface until the projected image pattern is in focus with the build surface. In some instances, the memory includes instructions to generate an image stack comprising a plurality of the projected image patterns. In certain instances, the memory includes instructions to determine the focal plane of the build surface based on the generated image stack. In certain cases, the memory includes instructions to determine the focal plane through a displacement depth of the build surface of 400 μm or less. In embodiments, the system provides for generating polymeric structures (e.g., polymeric microneedles) having a lattice microstructure resolution of 10 μm or less, such as 5 μm or less. In certain embodiments, the system is configured to provide for a resolution of from 1.0 μm to 4 μm, such as from 1.5 μm to 3.8 μm.

Aspects of the disclosure also include methods for making a polymeric microneedle having a lattice microstructure with one or more lattice cell units. Methods according to certain embodiments, include irradiating a polymerizable composition positioned between a build elevator and a build surface to generate a polymerizable composition having a first polymerized region of the polymerizable composition in contact with the build elevator and a first non-polymerized region of the polymerizable composition in contact with the build surface; displacing the build elevator away from the build surface; irradiating the first non-polymerized region of the polymerizable composition to generate a second polymerized region of the polymerizable composition in contact with the first polymerized region and a second non-polymerized region in contact with the build surface and repeating in a manner sufficient to generate a microneedle having a lattice microstructure. In some embodiments, the polymerizable composition is in contact with the build elevator and the build surface. In some instances, methods include irradiating the polymerizable composition for a duration sufficient to bond the first polymerized region of the polymerizable composition to the build elevator. In some instances, the build elevator is displaced in predetermined increments of from 0.5 μm to 1.0 μm. In certain instances, polymerizable composition is added to the build surface after each displacement of the build elevator away from the build surface. In some embodiments, the polymerizable composition is irradiated through build surface. In some instances, the polymerizable composition is irradiated in the presence of a polymerization inhibitor. In certain embodiments, the polymerizable composition is continuously polymerized while displacing the build elevator away from the build surface. In certain cases, the polymerization inhibitor is oxygen and the build surface is permeable to oxygen.

In some embodiments, methods include irradiating the polymerizable composition with a micro-digital light projection system. In some instances, a focal plane on the build surface is determined using the micro-digital light projection system. In some embodiments, determining the focal plane on the build surface includes irradiating the build surface with a stroboscopic light source through the tube lens and displacing the build surface until the light is focused on the build surface through the tube lens. In some instances, the build surface is irradiated with a plane of light having a projected image pattern with the stroboscopic light source. In certain instances, the build surface is displaced (e.g., continuously or in predetermined intervals) until the projected image pattern is in focus with the build surface. In some embodiments, the focal plane is determined with the photodetector of the micro-digital light projection system. In some instances, an image stack having a plurality of projected image patterns is generated. In some embodiments, the focal plane of the build surface is determined from the generated image stack. In certain embodiments, the focal plane is determined through a displacement depth of the build surface of 400 μm or less. In embodiments, methods as described here for generating polymeric microstructures (e.g., polymeric microneedles) having a lattice microstructure provide for a resolution of 10 μm or less, such as 5 μm or less. In certain embodiments, the subject methods provide for a resolution of from 1.0 μm to 4 μm, such as from 1.5 μm to 3.8 μm.

In some embodiments, methods include preparing a polymeric microneedle having an active agent compound. In some instances, the active agent compound is coated onto a surface of the polymeric microneedle. In some embodiments, the active agent compound is coated onto the surface of the polymeric microneedle by dip-coating or by spray coating. In other instances, the active agent compound is dry-cast (e.g., as a powder) onto the surface of the polymeric microneedle. In some instances, the active agent compound is incorporated into an interior space of the lattice microstructure of the polymeric microneedle. In some instances, the active agent is injected into the lattice microstructure. In other instances, the active agent is introduced into the polymeric microneedle by contacting the lattice microstructure with a composition containing the active agent compound and incorporating the active agent by capillary action. In yet other instances, the active agent compound is incorporated into the polymerizable composition and is incorporated within the interior space of the polymeric microneedle while forming the lattice microstructure.

BRIEF DESCRIPTION OF THE FIGURES

The invention may be best understood from the following detailed description when read in conjunction with the accompanying drawings. Included in the drawings are the following figures:

FIG. 2B depicts a comparison of line patterns, square arrays and hole arrays to demonstrate 1.5 μm-resolution by high resolution digital light projection continuous liquid interface production according to certain embodiments.

FIG. 9A depicts focus on the build platform with strobe light by finely adjusting the tube lens (highlighted in green); (i) build platform is out of focus, (ii) build platform is in focus. Scale bar: 2.5 mm. FIG. 9B depicts focus on a projected pattern by finely adjusting the vertical position of the build platform (highlighted in green); (i) projected pattern on the build platform is out of focus, (ii) adjusted build platform brings the projected pattern into focus. Scale bar: 2.5 mm. FIG. 9C depicts an edge profile of the projected pattern. FIG. 9D depicts the calculated modulation transfer function (MTF) of the edge profile. FIG. 9E depicts the through-focus sharpness performance obtained from scanning near a rough estimation of the optimal focal plane of 400 μm. Best focal plane with the highest sharpness performance is found and compared with actual prints. The z position with the highest sharpness also has the best resolved 3D print. Scale bar: 1.0 mm.

FIG. 10A depicts schematic of the single-digit-micron-resolution CLIP-based 3D printer. The 3D printer consists of a UV projector, a projection lens, a resin vat that contains an oxygen-permeable window, and a translation stage. FIG. 10B depicts a projection optics system that includes a UV camera and a computer for real-time monitoring, where the projected UV light path (purple) is reflected through the beam splitter and the reflected projection (yellow) is captured by the UV camera, thereby allowing for real-time monitoring of the projected images and enabling fine adjustment of the focal plane. FIG. 10C depicts a CLIP process that contains an oxygen-permeable window, which is not only highly transmissive to UV (385 nm) but also is permeable to oxygen. The permeated oxygen forms a thin layer of dead-zone above the window, where photopolymerization is inhibited, allowing a continuous 3D print.

FIG. 11A depicts a schematic of a general CLIP printing setup. The setup includes (from bottom to top) a UV light engine that illuminates UV projection at wavelength of 385 nm, an oxygen permeable window, a dead-zone (height h) where uncured resin flows through, cured resin, and a build platform that travels at a pulling rate U. FIG. 11B depicts a schematic of the stepped printing processes containing (i) initial step, (ii) stage movement, (iii) stage stoppage, and (iv) UV exposure, that are (v) repeated throughout the print process.

FIG. 12A depicts a simulation of point spread function (PSF) from Zemax and Gaussian approximation (for (i) 30-μm-pixel projection lens) and Gaussian approximation (for (ii) 1.5-μm-pixel projection lens). Insets are 2D visualization of the PSF. FIG. 12B depicts simulations of a full 3D print that combines optical Gaussian approximation and photopolymerization to predict the overall printing performance of a square pyramid structure (width 500 μm, height 1000 μm). Insets are SEM images of an actual 3D printed part for comparison (scale bar 250 μm).

FIG. 13A depicts transient photopolymerization gradient simulation. (i) Transient oxygen concentration profile in the dead-zone regime. (ii) Transient converted oligomer concentration in the dead-zone regime. (iii) Concentration of all components in the dead-zone regime at t=0.1(−). FIG. 13B depicts the steady state oxygen concentration in the dead-zone regime for both the analytical expression and numerical solution from PDEs. FIG. 13C depicts the dead-zone thickness at various values of the Damköhler number (Da) from both the analytical expression and the numerical solution of the PDEs. FIG. 13D provides the parameters used in the study.

FIG. 14A(i) depicts the velocity flow profile in the dead-zone regime for Newtonian fluid using the analytical expression derived. FIG. 14A(ii) depicts the velocity flow profile in the dead-zone regime for non-Newtonian fluid using the analytical expression derived. Notice here the non-Newtonian fluid is modeled with a power-law fluid with shear-thinning coefficient of n=0.87. FIG. 14B depicts the direct measurement of Stefan force. Experimental data are obtained through recording the Stefan force during print process for different 3D print part radius, ranging from 0.5 mm to 2.2 cm. Inset: Load-cell experimental setup for Stefan force measurement.

FIG. 15A depicts David by Michelangelo (1.2 cm height) (Florence, Italy), FIG. 15B depicts Rocky Statue (2 cm height) (Philadelphia, PA, USA), FIG. 15C depicts Statue of Liberty (1.5 cm) (New York, NY, USA), FIG. 15D depicts Lattice twisted bar (1.25 cm height), FIG. 15E depicts Eiffel Tower (Paris, France), FIG. 15F depicts Terraced microneedle, FIG. 15G depicts Square block array, FIG. 15H depicts Lattice block (Scale bar 1 mm).

FIGS. 16A-16D depict the resolution and print speed characterization of CLIP-based printing according to certain embodiments. FIG. 16A depicts a comparison plot of print speed and resolution between high-resolution CLIP and other high-resolution 3D printing technologies. FIG. 16B depicts a twisted lattice bar; The high-resolution CLIP 3D print and two-photon polymerization (TPP) (NanoScribe, Germany) show that the CLIP technology completed the full print in a much shorter print time compared to the TPP technology. FIG. 16C depicts sample images of 1.5 μm resolution CLIP printer resolution characterization designs for lines (top row) 30 μm (20 pixels), 15 μm (10 pixels) and 7.5 μm (5 pixels). (insets) side-view of lines resolvability. (bottom row) holes ranging from 37.5 μm (15 pixels) to 18 μm (12 pixels). FIG. 16D depicts a summary table of resolution characterization for single-digit-micron-resolution CLIP-based 3D printer.

FIG. 17A depicts a sample image at a through-focus position 150 μm away from the scan starting position. FIG. 17B depicts applied feature detection, extraction, and centroid analysis for full field of view. Field-of-view (FOV) at various distance from the image center are shown. FIG. 17C depicts Full FOV edge profile extraction by finding the nearest adjacent neighbors of a given centroid. FIG. 17D depicts an average box of width 10 pixels is placed around each sampled edge profile to obtain the average edge profile for each edge.

FIG. 18A depicts critical dimension (CD) extraction using the 150 threshold method. FIG. 18B depicts sample line edge profile of a line designed to print at 15 μm width. FIG. 18C depicts Valley-to-peak intensity profile extraction and polynomial fitting is imposed to obtain the mid-point in the intensity profile. FIG. 18D depicts peak-to-valley intensity profile extraction and polynomial fitting is imposed to obtain the mid-point in the intensity profile FIG. 19A depicts flow sweep of TMPTA resin. FIG. 19B depicts flow sweep of EPU 40 resin. FIG. 19C depicts stress relaxation of uncured TMPTA and EPU 40 resin.

FIG. 20A depicts transient stress-relaxation vs. print diameter for TMPTA resin at different print diameters ranging from dark, 4 mm, 1 cm, 1.6 cm, and 2.2 cm. FIG. 20B depicts Extracted stress-relaxation time plotted against print diameters.

DETAILED DESCRIPTION

Figure 1:
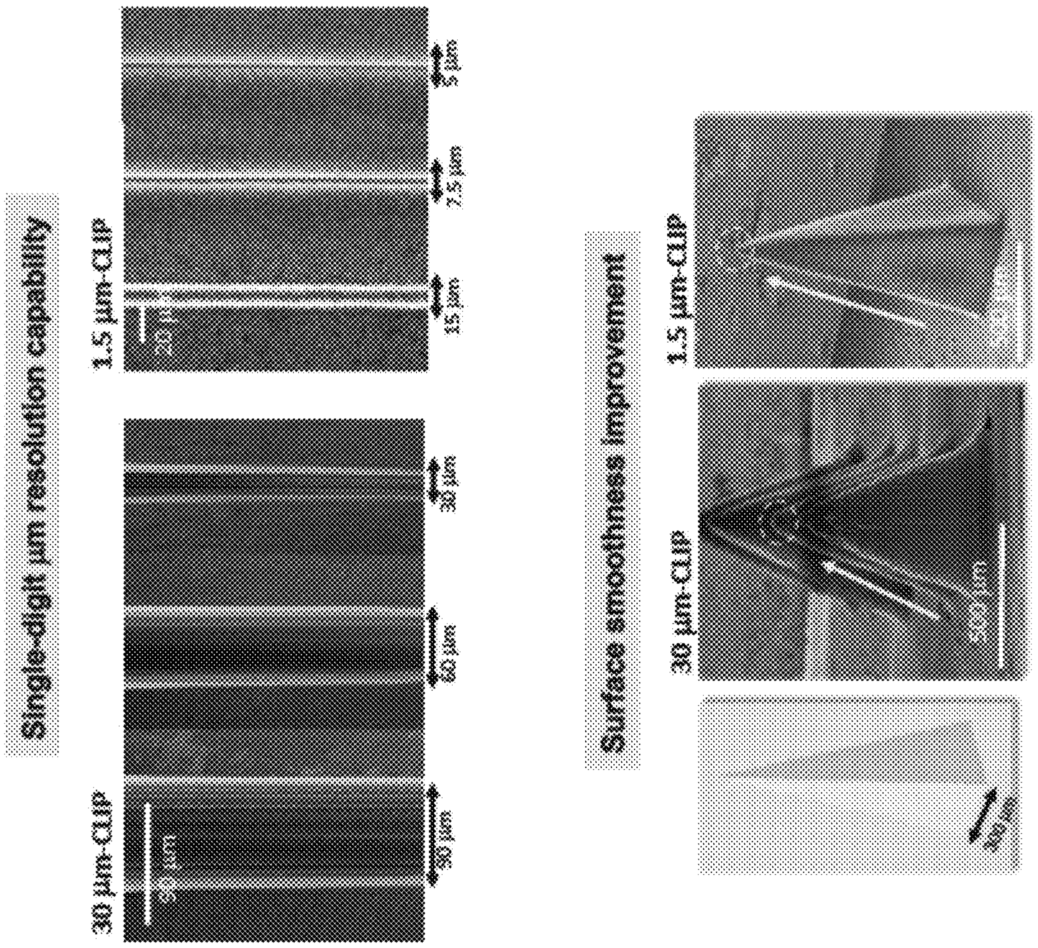
FIG. 1 depicts a comparison of single digit μm resolution capability by high resolution digital light projection continuous liquid interface production according to certain embodiments.

Aspects of the present disclosure include polymeric structures (e.g., microneedles) having a lattice microstructure composed of one or more lattice cell units. Polymeric structures according to certain embodiments have repeating lattice cell units that are formed by high resolution continuous liquid interface production. Aspects also include systems for making polymeric structures having a lattice microstructure. Systems according to certain embodiments include a micro-digital light projection system having a light beam generator component and a light projection monitoring component and a liquid interface polymerization module having a build elevator and a build surface configured for generating the polymeric lattice microstructure from a polymerizable composition positioned therebetween. Methods for making polymeric structures having a lattice microstructure with the subject systems are also provided. Patches having an array of polymeric microneedles for applying to a skin surface of a subject are also described. In some embodiments, patches include microneedles that contain an active agent compound (e.g., an immunogenic active agent). Methods for applying the patches to the skin surface of a subject are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

As summarized above, the present disclosure provides polymeric microstructures (e.g., microneedles) having a lattice microstructure composed of one or more lattice cell units. In further describing embodiments of the disclosure, polymeric structures having have repeating lattice cell units, such as formed by high resolution continuous liquid interface production are first described in greater detail. Next, systems and methods for making polymeric microstructures having lattice microstructures are described. Patches having an array of polymeric microneedles for applying to a skin surface of a subject are also provided. In some embodiments, patches include microneedles that contain an active agent compound (e.g., an immunogenic active agent). Methods for applying the patches to the skin surface of a subject are described.

Polymeric Microneedles Having a Lattice Microstructure

Figure 2A:
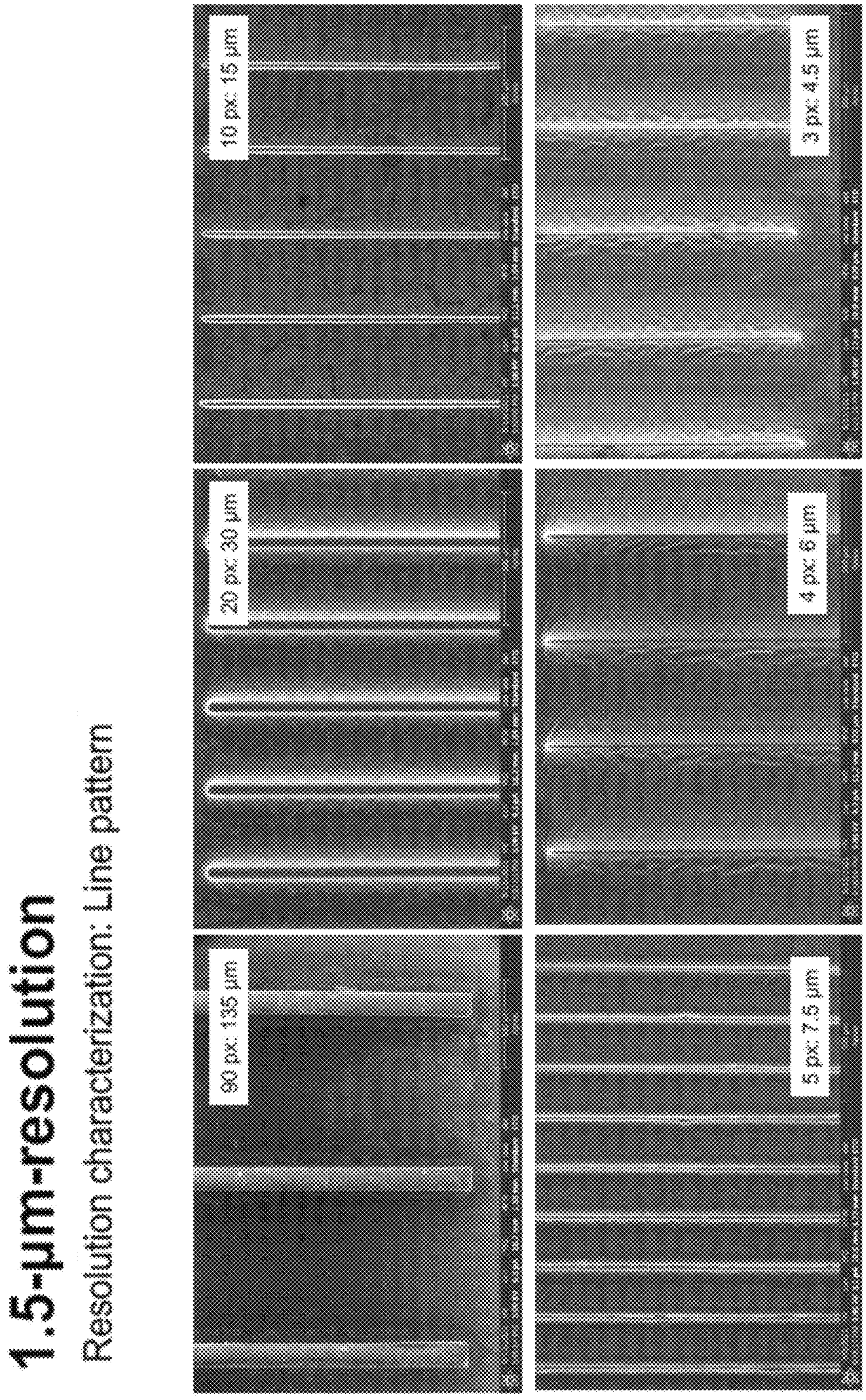
FIG. 2A depicts line patterns demonstrating 1.5 μm-resolution by high resolution digital light projection continuous liquid interface production according to certain embodiments.

Aspects of the present disclosure include polymeric microneedles having a lattice microstructure with of one or more lattice cell units. As described in greater detail below, in certain instances the polymeric structures are formed by high resolution digital light projection continuous liquid interface production (e.g., DLP-CLIP) which provide for microarchitectures having resolutions of 100 μm or less, such as 90 μm or less such as 75 μm or less and including resolutions of 50 μm or less. FIG. 1 depicts a comparison of single digit μm resolution capability by high resolution digital light projection continuous liquid interface production as described herein. In contrast to conventional additive manufacturing such as stereolithography (SLA), direct ink writing (DIW), two-photo polymerization (TPP) which cannot provide for lattice microstructures having resolutions as described herein due to low printing resolution, the polymeric structures described herein can have pixel sizes of 150 μm×150 μm or less, such as 75 μm×75 μm or less, such as 30 μm×30 μm or less, such as 7.45 μm×7.45 μm or less, such as 3.7 μm×3.7 μm or less and including pixel sizes of 1.5 μm×1.5 μm or less. FIG. 2A depicts line patterns to demonstrate 1.5 μm-resolution by high resolution digital light projection continuous liquid interface production. FIG. 2B depicts a comparison of line patterns, square arrays and hole arrays to demonstrate 1.5 μm-resolution by high resolution digital light projection continuous liquid interface production.

In some embodiments, methods for making polymeric structures described herein provide for increase speed in additive manufacturing, such as where production can be achieved in 200 ms or less, such as 190 ms or less, such as 180 ms or less, such as 170 ms or less, such as 160 ms or less, such as 150 ms or less, such as 100 ms or less and including 50 ms or less. In certain instances, high resolution digital light projection continuous liquid interface production described herein provides for generating polymeric structures having a lattice microstructure that is 10-fold faster or more than conventional additive manufacturing (e.g., stereolithography (SLA), direct ink writing (DIW), two-photo polymerization (TPP)), such as 20-fold faster or more, such as 50-fold faster or more, such as 102-fold faster or more, such as 103-fold faster or more, such as 104-fold faster or more and including 105-fold faster or more.

Figure 3A:
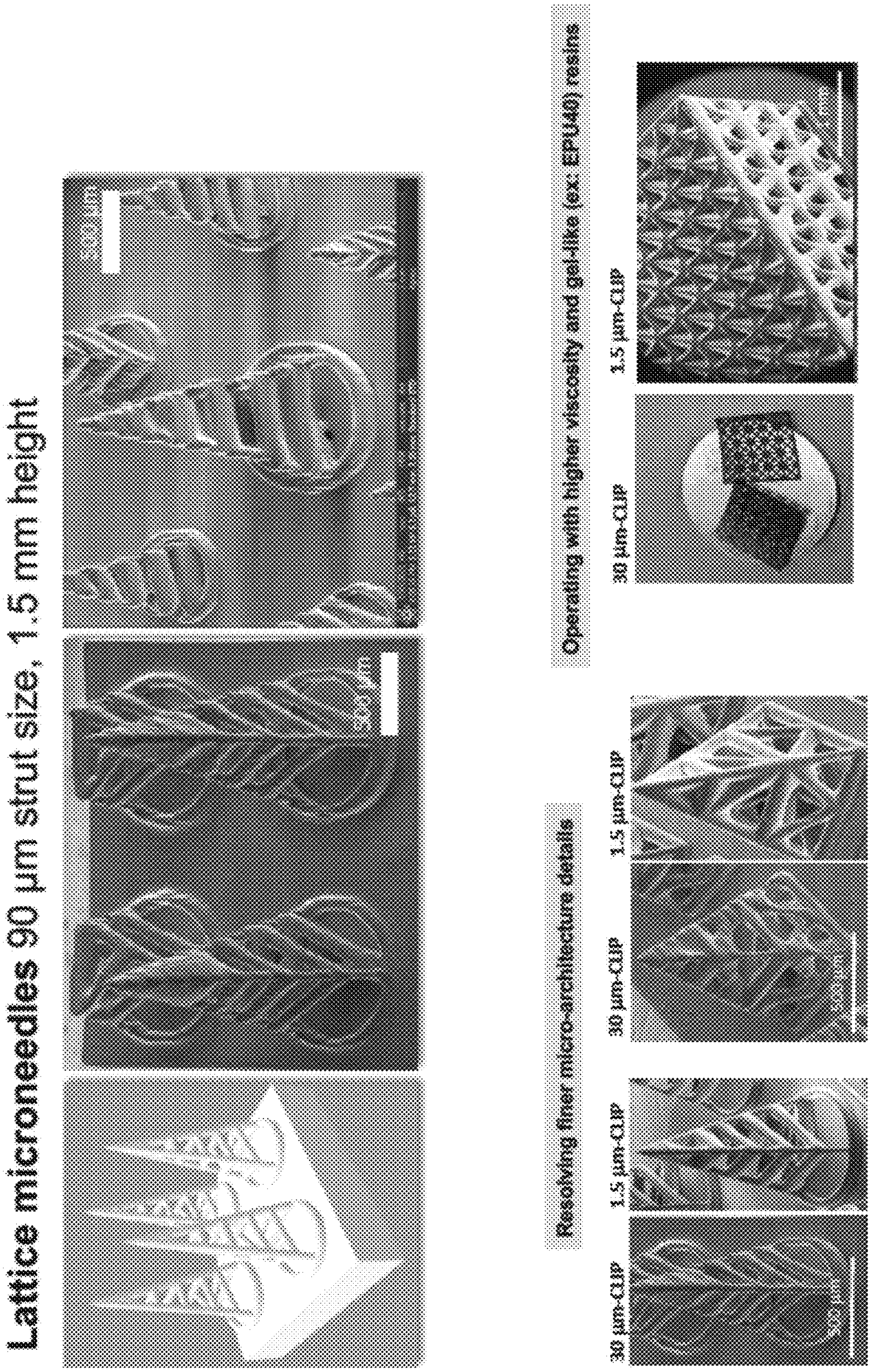
FIG. 3A depicts examples of lattice microneedles according to certain embodiments.
Figure 3A:
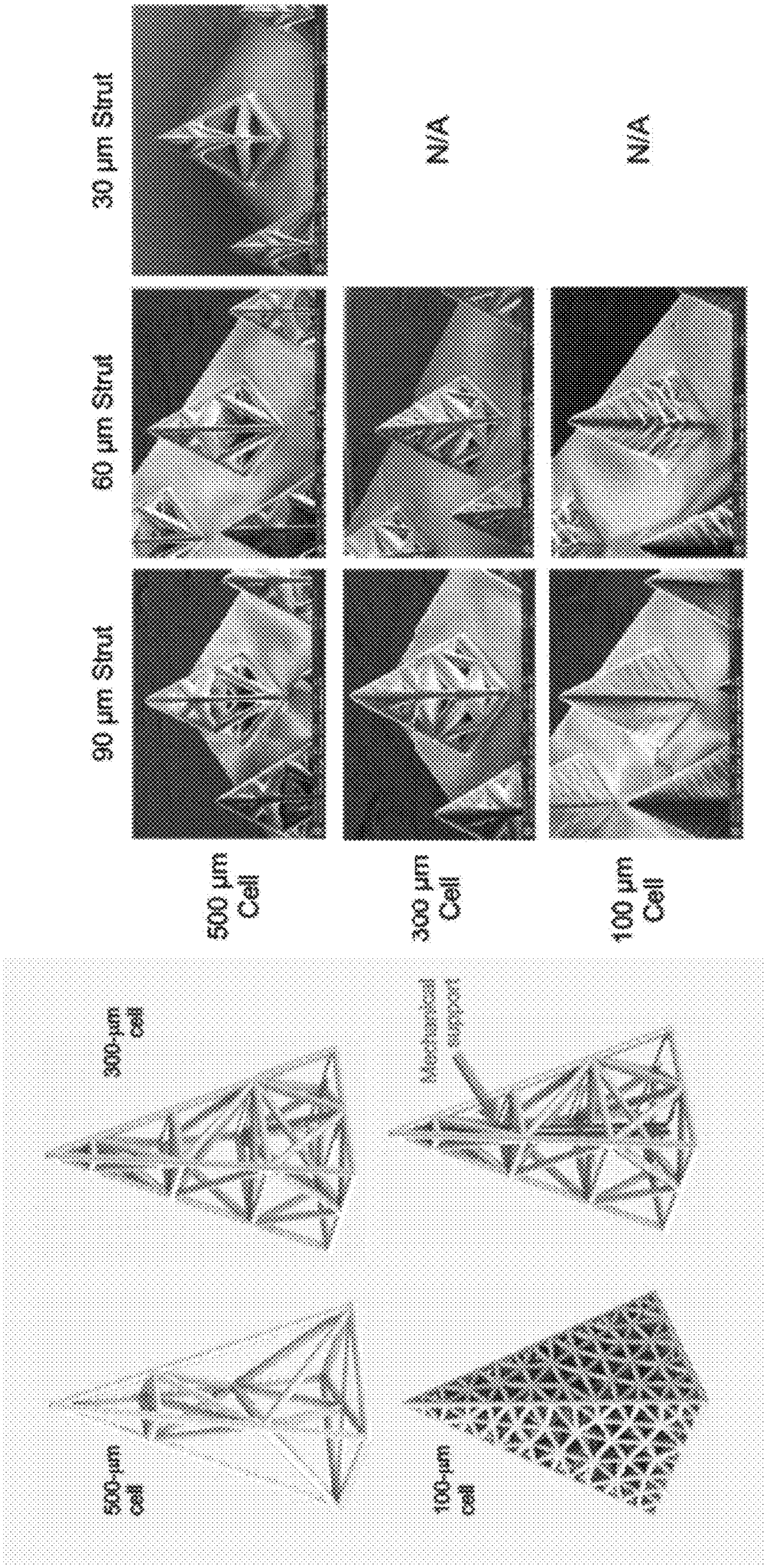
Figure 3B:
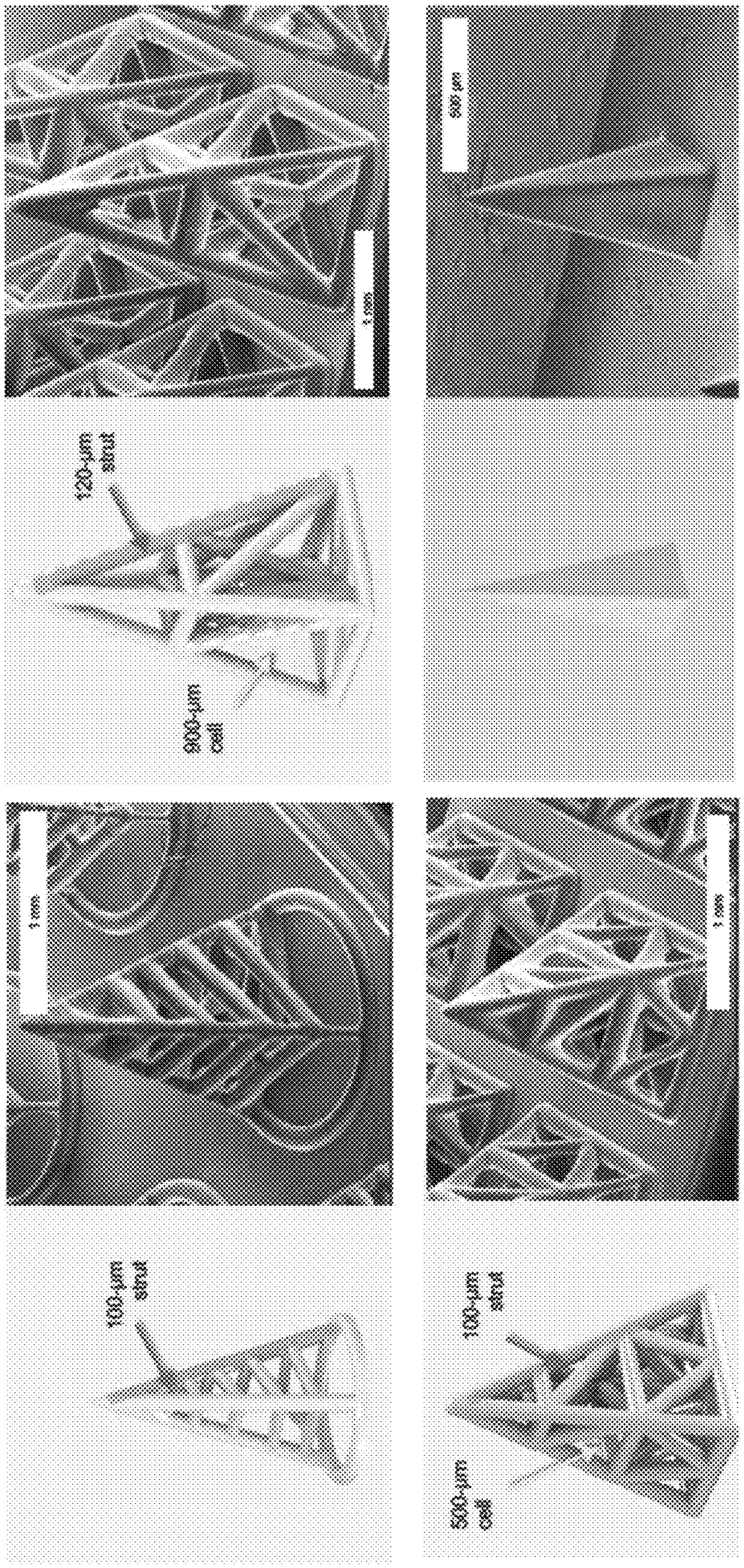
FIG. 3B depicts examples of lattice microneedles generated by 1.5 μm resolution digital light projection continuous liquid interface production according to certain embodiments.

In addition, the subject polymeric microneedles have microarchitecture including struts which provide for mechanical integrity sufficient for use in delivering an active agent compound as a polymeric microneedle or for collecting (e.g., by fluidic wicking) a biological fluid from a subject. The subject polymeric microneedles provide for enhance drug delivery such as by sustained or controlled release as compared to solid microstructures which can only employ an active agent surface coating and better mechanical integrity as compared to hollow microneedles. FIG. 3A depicts examples of lattice microneedles according to certain embodiments. In some instances, the micro-architecture has 30 μm resolution. In some instances, the micro-architecture has 1.5 μm resolution. FIG. 3B depicts examples of lattice microneedles generated by 1.5 μm resolution digital light projection continuous liquid interface production according to certain embodiments. In some instances, the polymeric microneedles have a cell size of 500 μm or 900 μm and struts sizes of 100 μm or 120 μm.

Figure 4B:
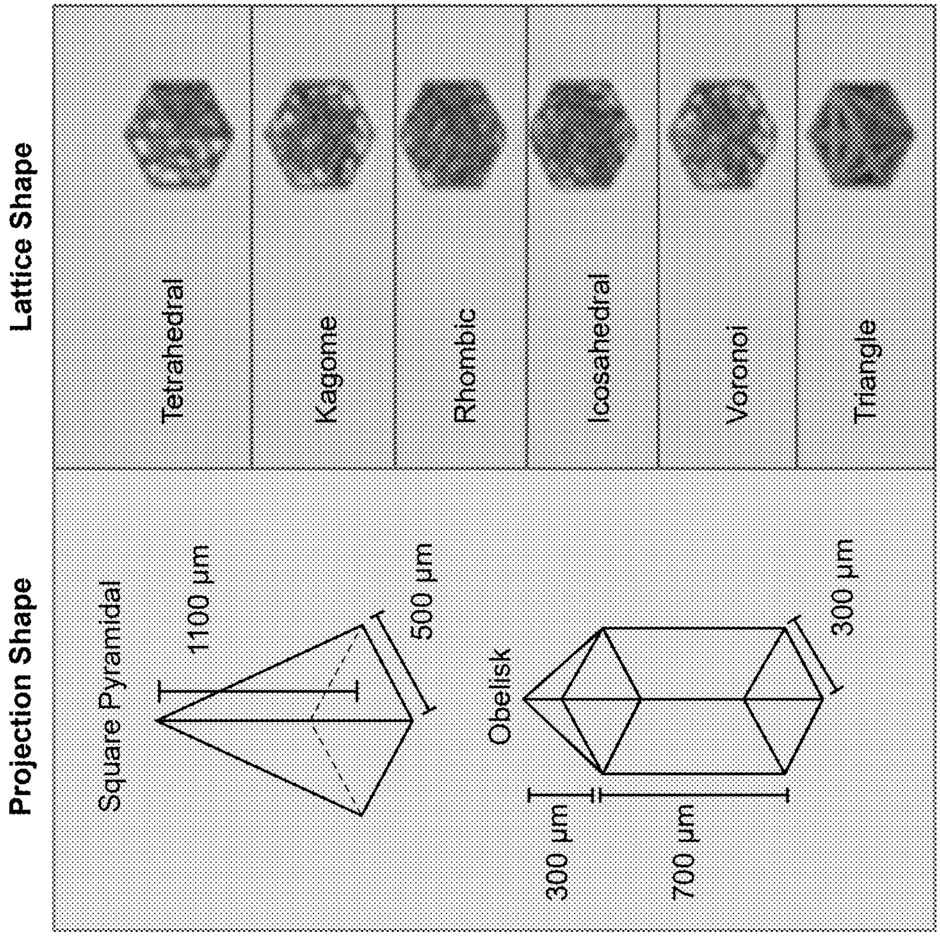
FIG. 4B depicts different projection shapes and lattice shapes for lattice microstructure of a polymeric microneedle.
Figure 4A:
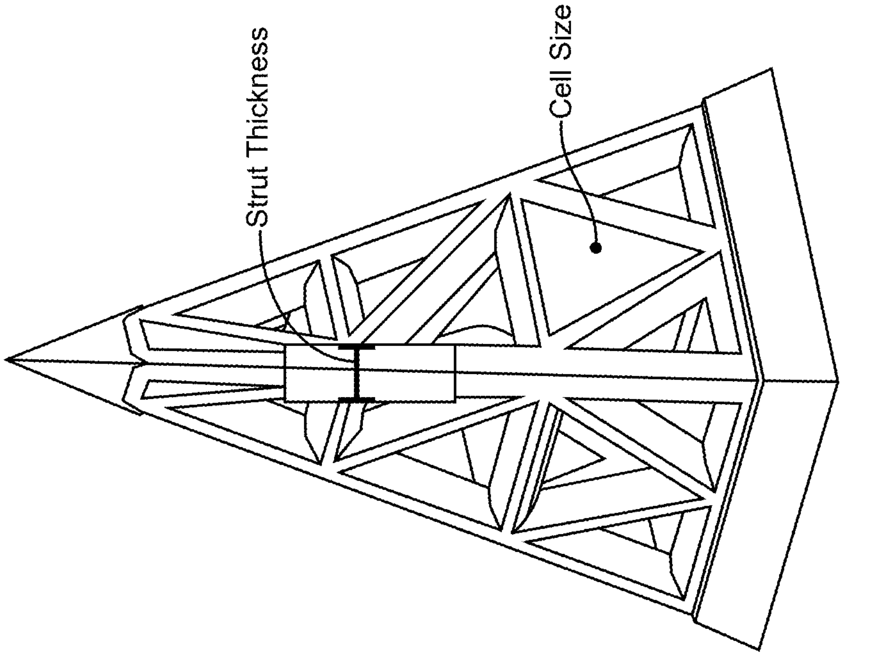
FIG. 4A depicts an example of a lattice microstructure of a polymeric microneedle according to certain embodiments.

In some embodiments, the lattice microstructures of the polymeric microneedles described herein have 2 or more repeating lattice cell units, such as 3 or more repeating lattice cell units, such as 4 or more repeating lattice cell units and including 5 or more repeating lattice cell units. In some instances, the lattice microstructure has a lattice shape selected from tetrahedral, Kagome, rhombic, icosahedral, Voronoi or triangular. In some instances, the lattice microstructure is composed of two or more lattice cell units having different lattice shapes, such where the lattice microstructure is composed of 3 or more different lattice shapes, such as 4 or more different lattice shapes and including where the lattice microstructure is composed of 5 or more different lattice shapes. FIG. 4A depicts an example of a lattice microstructure of a polymeric microneedle according to certain embodiments. FIG. 4B depicts different projection shapes and lattice shapes for lattice microstructure of a polymeric microneedle.

Figure 5:
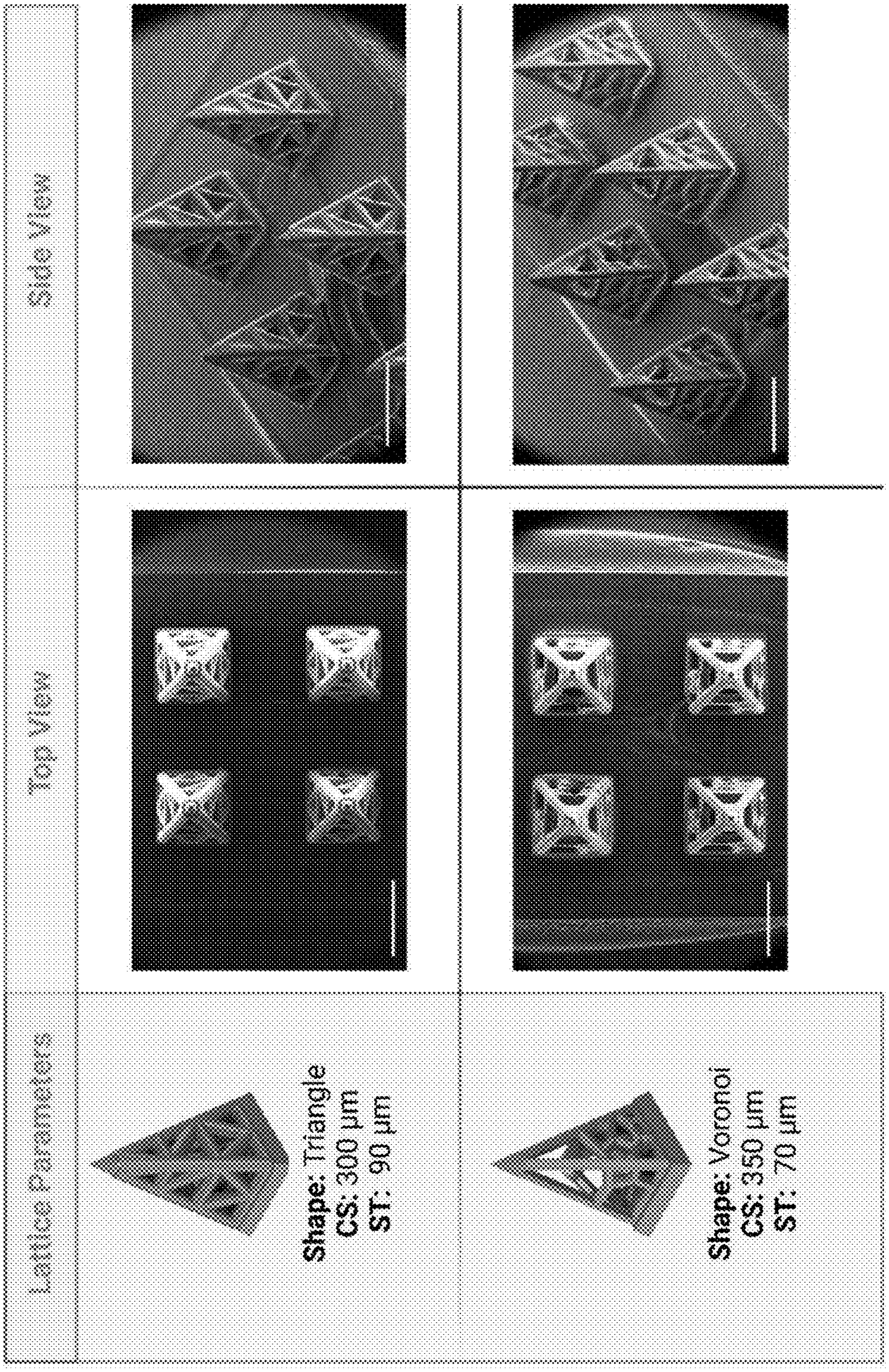
FIG. 5 depicts SEM Images of polymeric microneedles having a triangular-shaped lattice microstructure and a Voronoi-shaped lattice microstructure according to certain embodiments.

In some embodiments, the lattice microstructure is formed from lattice cells having a unit size of from 1 μm to 1000 μm, such as from 5 μm to 950 μm, such as from 10 μm to 900 μm, such as from 15 μm to 850 μm, such as from 20 μm to 800 μm, such as from 25 μm to 750 μm, such as from 30 μm to 700 μm, such as from 35 μm to 650 μm, such as from 40 μm to 600 μm, such as from 45 μm to 550 μm and including from 50 μm to 500 μm, for example from 200 μm to 500 μm. In embodiments, the lattice microstructure has a volume of from 0.01 μL to 25 μL, such as from 0.02 μL to 24.5 μL, such as from 0.03 μL to 24 μL, such as from 0.04 μL to 23.5 μL, such as rom 0.05 μL to 23 μL, such as from 0.6 μL to 22.5 μL, such as from 0.07 μL to 22 μL, such as from 0.08 μL to 21.5 μL, such as from 0.09 μL to 21 μL, such as from 0.1 μL to 20 μL, such as from 0.5 μL to 19 μL, such as from 1 μL to 18 μL, such as from 2 μL to 17 μL, such as from 3 μL to 16 μL and including from 4 μL to 15 μL. As described in greater detail below, the polymeric structure may be configured to contain a composition within the lattice microstructure (e.g., a fluidic composition) where in some embodiments the lattice microstructure is configured to contain a volume of from 0.1 μL to 25 μL, such as from 0.2 μL to 24 μL, such as from 0.3 μL to 23 μL, such as from 0.4 μL to 22 μL, such as rom 0.5 μL to 21 μL, such as from 0.6 μL to 20 μL, such as from 0.7 μL to 19 μL, such as from 0.8 μL to 18 μL, such as from 0.9 μL to 17 μL and including where the lattice microstructure is configured to contain a volume of from 1 μL to 15 μL. FIG. 5 depicts SEM Images of polymeric microneedles having a triangular-shaped lattice microstructure and a Voronoi-shaped lattice microstructure according to certain embodiments. The polymeric microneedles were formed from using Keysplint hard resin. (Scale Bar=500 μm. CS=cell size, ST=strut thickness).

Figure 6A:
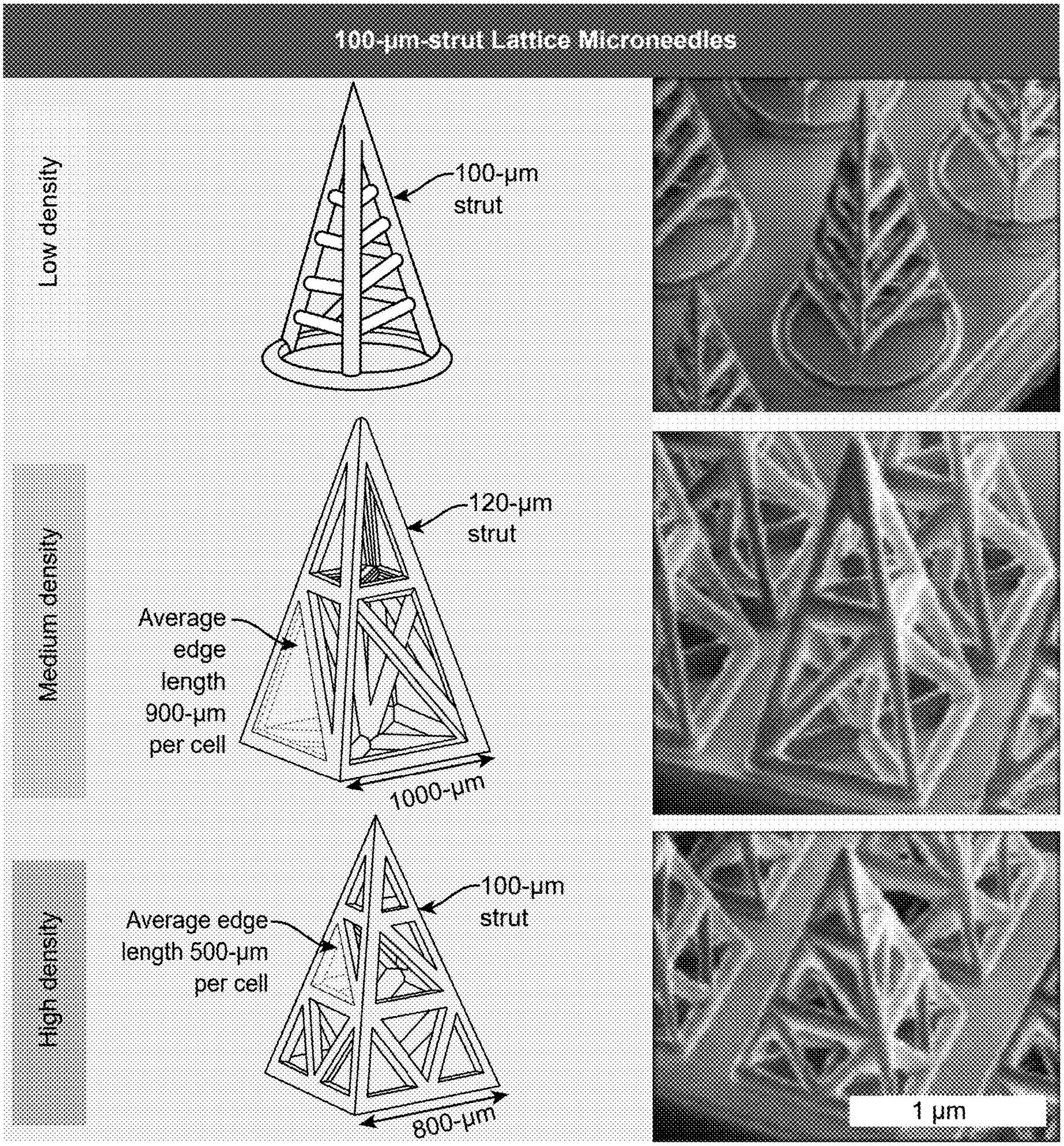
FIG. 6A depicts lattice microstructures having different densities of lattice cell units according to certain embodiments.
Figure 6B:
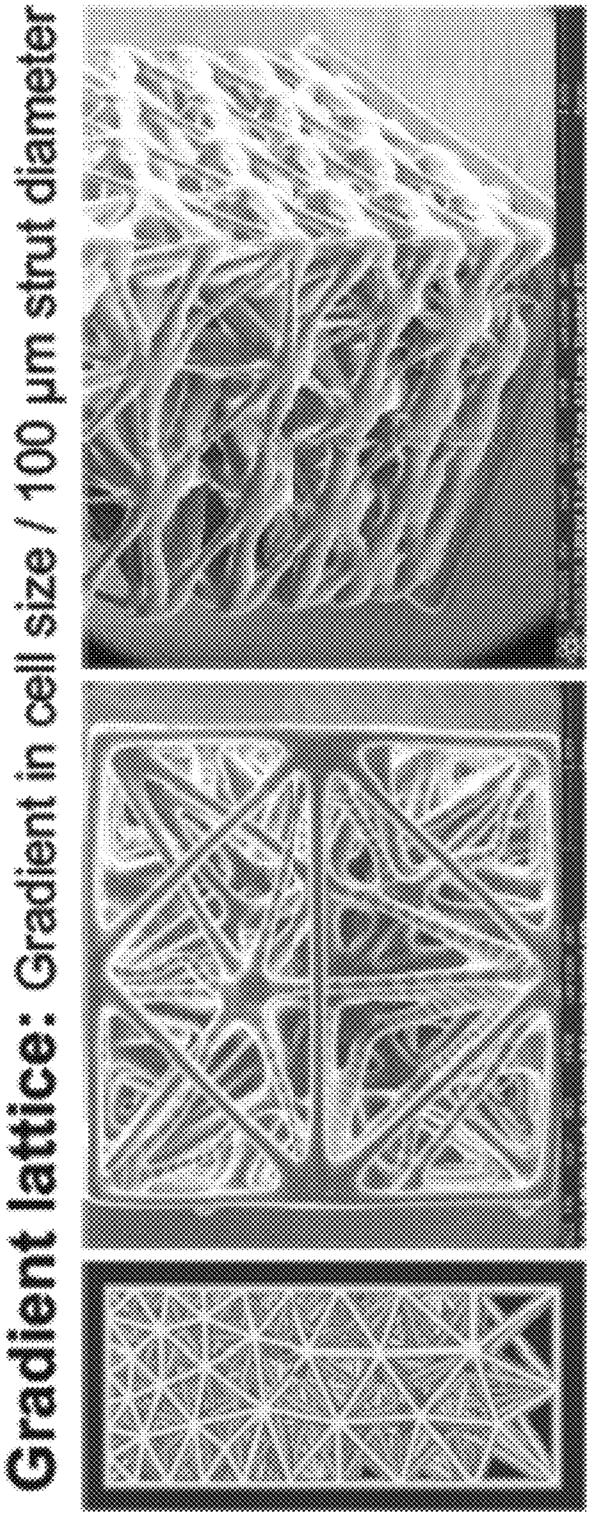
FIG. 6B depicts lattice microstructures having a gradient in the density of lattice cell units according to certain embodiments.

In some embodiments, the density of lattice cell units remains constant throughout the lattice microstructure of polymeric structures of interest. FIG. 6A depicts lattice microstructures having different densities of lattice cell units according to certain embodiments. As shown in FIG. 6A, polymeric microneedles according to certain embodiments can have a low density of lattice cell units, a medium density of lattice cell units and a high density of lattice cell units. In other embodiments, the density of lattice cell units varies at one or more parts the lattice microstructure. In some embodiments, the lattice microstructure contains regions of increased lattice cell density, such as where the lattice cell density in these regions is increased by 1% or more across the longitudinal axis of the lattice microstructure, such as by 2% or more, such as by 3% or more, such as by 4% or more, such as by 5% or more, such as by 10% or more, such as by 20% or more, such as by 30% or more, such as by 40% or more and including by 50% or more. In some instances, the regions of increased lattice cell density are present at various increments across the longitudinal axis of the lattice microstructure. For example, the regions of increased lattice cell density may be present at increments of every 10 μm or more across the longitudinal axis of the lattice microstructure, such as every 20 μm or more, such as every 30 μm or more, such as every 40 μm or more and including every 50 μm or more. FIG. 6B depicts lattice microstructures having a gradient in the density of lattice cell units according to certain embodiments.

In some instances, the density of lattice cell units exhibits a gradient in one or more parts of the lattice microstructure. In certain instances, the density of lattice cell units gradually increases across a longitudinal axis of the lattice microstructure. For example, the density of the lattice cell units may increase by 1% or more across the longitudinal axis of the lattice microstructure, such as by 2% or more, such as by 3% or more, such as by 4% or more, such as by 5% or more, such as by 10% or more, such as by 20% or more, such as by 30% or more, such as by 40% or more and including by 50% or more. In some embodiments, the density of the lattice cell units increases at predetermined increments across the longitudinal axis of the lattice microstructure, such as where the density of the lattice cell units increases every 1% or more of the length across the longitudinal axis of the lattice microstructure, such as every 2% or more, such as every 3% or more, such as every 4% or more, such as every 5% or more, such as every 6% or more, such as every 7% or more, such as every 8% or more, such as every 9% or more and including every 10% or more. Depending on the size of the lattice microstructure, the density of the lattice cell units may increase every 1 μm or more across the longitudinal axis, such as every 2 μm or more, such as every 3 μm or more, such as every 4 μm or more, such as every 5 μm or more, such as every 10 μm or more, such as every 20 μm or more, such as every 30 μm or more, such as every 40 μm or more and including every 50 μm or more. For example, the density of the lattice cell units may increase by 1% or more every 25 μm or more across the longitudinal axis of the lattice microstructure, such as by 2% or more every 25 μm or more across the longitudinal axis of the lattice microstructure, such as 5% or more every 25 μm or more across the longitudinal axis of the lattice microstructure.

In some embodiments, the lattice microstructure includes a plurality of struts. Struts according to certain embodiments provide mechanical integrity to the lattice microstructure. In some instances, struts have a thickness which range from 1 μm to 200 μm, such as from 2 μm to 190 μm, such as from 3 μm to 180 μm, such as from 4 μm to 170 μm, such as from 5 μm to 160 μm, such as from 6 μm to 150 μm, such as from 7 μm to 140 μm, such as from 8 μm to 130 μm, such as from 9 μm to 120 μm and including from 10 μm to 100 μm. For instance, the strut size may be in certain examples from 50 μm to 100 μm such as 70 μm to 90 μm. (see e.g., FIG. 3A)

Figure 7:
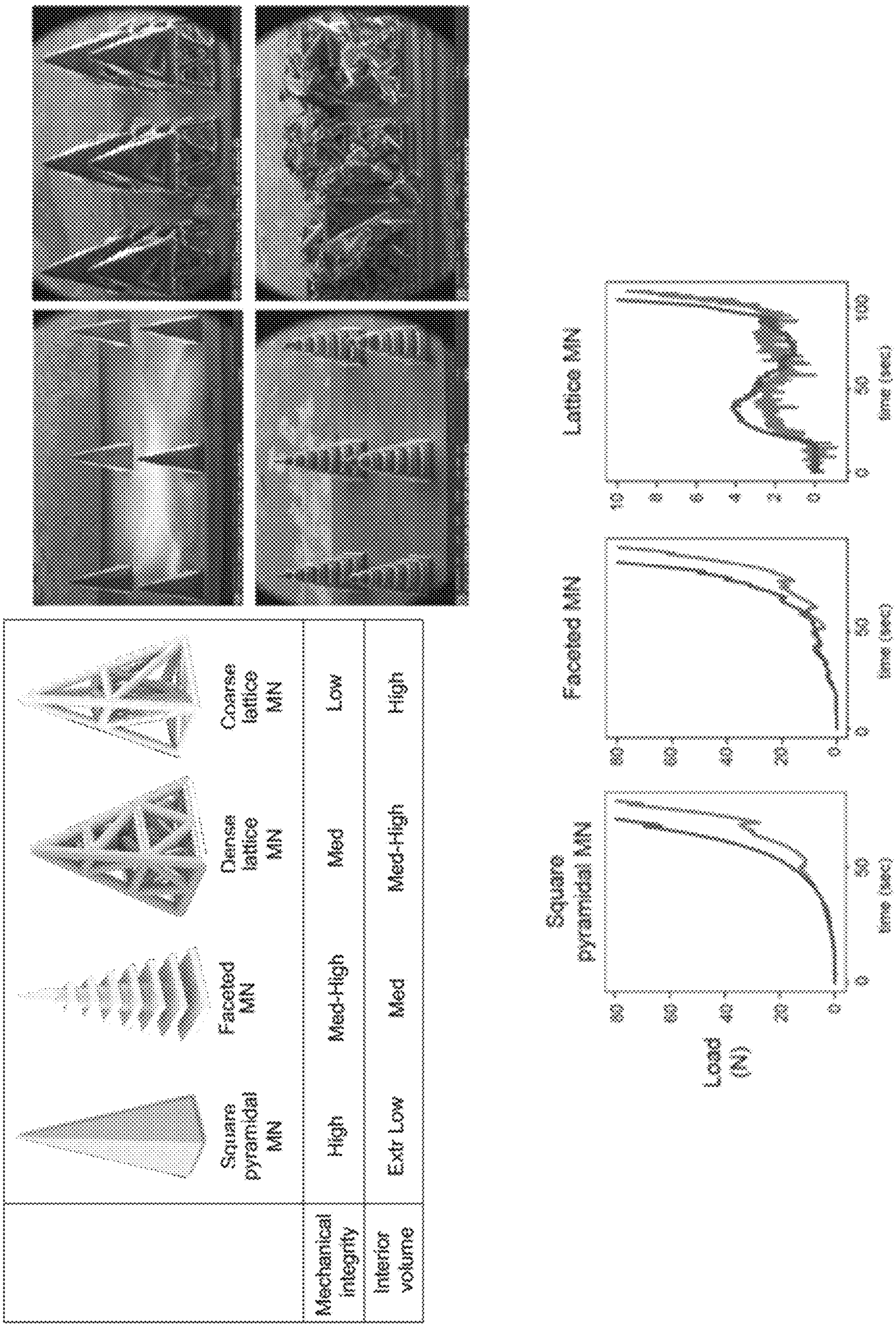
FIG. 7 depicts a comparison of the mechanical integrity of different polymeric microneedles generated by 1.5 μm-resolution digital light projection continuous liquid interface production according to certain embodiments.

In some instances, the lattice microstructures exhibit a mechanical integrity sufficient to be load bearing, such as for example as a polymeric microneedle (as described below) that can be administered to a subject. Depending on the density of the lattice microstructure, in some embodiments polymeric structures exhibit a mechanical integrity sufficient to carry a load of 0.1 N or more, such as 0.5 N or more, such as 1 N or more, such as 2 N or more, such as 3 N or more, such as 4 N or more, such as 5 N or more, such as 10 N or more, such as 15 N or more, such as 20 N or more, such as 25 N or more, such as 50 N or more, such as 75 N or more and including 100 N or more. In some embodiments, the lattice microstructure includes one or more structural support struts which is positioned within the lattice microstructure to provide increased mechanical integrity, such as where the mechanical integrity is increased by 5% or more, such as by 25% or more and including by 75% or more. For example, the structural support struts may increase the load that the lattice microstructure can carry by 0.5 N or more, such as by 1 N or more, such as by 5 N or more, such as by 10 N or more, such as by 25 N or more, such as by 50 N or more and including by 100 N or more. In some instances, the structural support struts are positioned within the interior of the lattice microstructure. In other embodiments, the support struts are positioned along the exterior of the lattice microstructure. FIG. 7 depicts a comparison of the mechanical integrity of different polymeric microneedles generated by 1.5 μm-resolution digital light projection continuous liquid interface production according to certain embodiments. Polymeric microneedles having a lattice microstructure were load-tested against square pyramidal solid and faceted microneedles. As shown in FIG. 7, the mechanical integrity of microneedles increased with decreasing interior volume where coarse microlattice microneedles having high interior volume exhibited the lowest mechanical integrity whereas solid square pyramidal microneedles having no interior volume exhibited the greatest mechanical integrity.

Polymeric microneedles may be any three-dimensional geometric shape including but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. Polymeric structures having a lattice microstructure of interest may have a length of from 50 μm to 2000 μm, such as from 75 μm to 1950 μm, such as from 100 μm to 1900 μm, such as from 125 μm to 1850 μm, such as from 150 μm to 1800 μm, such as from 175 μm to 1750 μm, such as from 200 μm to 1700 μm, such as from 225 μm to 1650 μm, such as from 250 μm to 1600 μm, such as from 275 μm to 1550 μm and including from 300 μm to 1500 μm. Polymeric structures having a lattice microstructure of interest may have a width of from 50 μm to 1000 μm, such as from 75 μm to 950 μm, such as from 100 μm to 900 μm, such as from 125 μm to 850 μm, such as from 150 μm to 800 μm, such as from 175 μm to 750 μm, such as from 200 μm to 700 μm, such as from 225 μm to 650 μm, such as from 250 μm to 600 μm, such as from 275 μm to 550 μm and including from 300 μm to 500 μm.

In embodiments, the polymeric structure is formed from a polymerizable material which may include but is not limited to polycaprolactone, polyalycolic acid, polylactic acid, polylactic-co-glycolic acid, polyethylene glycol, thiolenes, anhydrides, polyacrylic acid, poly methylmethacrylate, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof. In certain embodiments, the polymeric structure is formed from polyethylene glycol dimethacrylate (PEGDMA). In certain embodiments, the polymeric structure is formed from trimethylolpropane triacrylate (TMPTA) monomer. In certain embodiments, the polymerizable material is selected from polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the beam-splitter is formed from a polyester, where polyesters of interest may include, but are not limited to, poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(¿-caprolactone) and poly(β-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); polyethylene Terephthalate (e.g., Mylar™ Polyethylene Terephthalate), combinations thereof, and the like.

In some embodiments, the polymeric structures are formed from a polymerizable material which is biodegradable. The term "biodegradable" is used herein in its conventional sense to refer to a material which is capable of being decomposed, broken down or degraded by a living organism, such as microorganisms for example bacteria. In certain embodiments, the polymerizable material is dissolvable in an aqueous medium. In embodiments where the polymeric structure is formed from a dissolvable material, the lattice microstructure may be dissolved in water over a period of time of 0.01 hours or more, such as over 0.05 hours or more, such as over 0.1 hours or more, such as over 0.5 hours or more, such as over 1 hour or more, such as over 2 hours or more, such as over 6 hours or more, such as over 12 hours or more, such as over 18 hours or more, such as over 24 hours or more, such as over 36 hours or more, such as over 48 hours or more, such as over 72 hours or more, such as over 96 hours or more, such as over 120 hours or more, such as over 144 hours or more and including over 168 hours or more.

In some embodiments, the microneedle includes a tip section, a body section and a base section. In embodiments, one or more of the tip section, body section and base section of the polymeric microneedle have a lattice microstructure as described above. In some instances, one or more of the tip section, body section and base section have a solid structure (i.e., interior space that is completely filled). In some instances, one or more of the tip section, body section and base section have a hollow interior space. In certain embodiments, the microneedle includes a tip section having a solid structure, a body section having a lattice microstructure and a base section having a solid structure. In embodiments, the tip section may be a length of from 10 μm to 500 μm, such as from 20 μm to 490 μm, such as from 30 μm to 480 μm, such as from 40 μm to 470 μm, such as from 50 μm to 460 μm, such as from 60 μm to 450 μm, such as from 70 μm to 440 μm, such as from 80 μm to 430 μm, such as from 90 μm to 420 μm, such as from 100 μm to 410 μm, such as from 110 μm to 400 μm, such as from 120 μm to 390 μm, such as from 130 μm to 380 μm, such as from 140 μm to 370 μm and including from 150 μm to 360 μm. In some instances, the microneedle has a tip diameter of from 0.1 μm to 10 μm, such as from 0.5 μm to 9 μm, such as from 1 μm to 8 μm and including from 2 μm to 7 μm. In some embodiments, the body section has a length of from 10 μm to 500 μm, such as from 20 μm to 490 μm, such as from 30 μm to 480 μm, such as from 40 μm to 470 μm, such as from 50 μm to 460 μm, such as from 60 μm to 450 μm, such as from 70 μm to 440 μm, such as from 80 μm to 430 μm, such as from 90 μm to 420 μm, such as from 100 μm to 410 μm, such as from 110 μm to 400 μm, such as from 120 μm to 390 μm, such as from 130 μm to 380 μm, such as from 140 μm to 370 μm and including from 150 μm to 360 μm. In some embodiments, the base section has a length of from 10 μm to 500 μm, such as from 20 μm to 490 μm, such as from 30 μm to 480 μm, such as from 40 μm to 470 μm, such as from 50 μm to 460 μm, such as from 60 μm to 450 μm, such as from 70 μm to 440 μm, such as from 80 μm to 430 μm, such as from 90 μm to 420 μm, such as from 100 μm to 410 μm, such as from 110 μm to 400 μm, such as from 120 μm to 390 μm, such as from 130 μm to 380 μm, such as from 140 μm to 370 μm and including from 150 μm to 360 μm.

In some embodiments, the lattice microstructure of the polymeric microneedles is formed from lattice cells having a unit size of from 1 μm to 1000 μm, such as from 5 μm to 950 μm, such as from 10 μm to 900 μm, such as from 15 μm to 850 μm, such as from 20 μm to 800 μm, such as from 25 μm to 750 μm, such as from 30 μm to 700 μm, such as from 35 μm to 650 μm, such as from 40 μm to 600 μm, such as from 45 μm to 550 μm and including from 50 μm to 500 μm, for example from 200 μm to 500 μm. In embodiments, the polymeric microneedles has a volume of from 0.01 μL to 25 μL, such as from 0.02 μL to 24.5 μL, such as from 0.03 μL to 24 μL, such as from 0.04 μL to 23.5 μL, such as rom 0.05 μL to 23 μL, such as from 0.6 μL to 22.5 μL, such as from 0.07 μL to 22 μL, such as from 0.08 μL to 21.5 μL, such as from 0.09 μL to 21 μL, such as from 0.1 μL to 20 μL, such as from 0.5 μL to 19 μL, such as from 1 μL to 18 μL, such as from 2 μL to 17 μL, such as from 3 μL to 16 μL and including from 4 μL to 15 μL. In some embodiments, the polymeric microneedle is configured to deliver a volume (e.g., administering an active agent to a subject by injection) of from 0.1 μL to 25 μL, such as from 0.2 μL to 24 μL, such as from 0.3 μL to 23 μL, such as from 0.4 μL to 22 μL, such as rom 0.5 μL to 21 μL, such as from 0.6 μL to 20 μL, such as from 0.7 μL to 19 μL, such as from 0.8 μL to 18 μL, such as from 0.9 μL to 17 μL and including where the lattice microstructure is configured to contain a volume of from 1 μL to 15 μL.

In certain embodiments, polymeric microneedles described herein are dynamic microneedles which can alter geometry or shape in response to an applied stimulus. In certain embodiments, the stimulus is applied mechanical pressure (e.g., pressure when inserted through a skin surface of a subject). In some instances, the dynamic microneedle is compliant and exhibits motion through elastic deformation of the polymeric microstructure. In some embodiments, the microneedle deploys a barb structure in response to the applied stimulus.

Figure 8A:
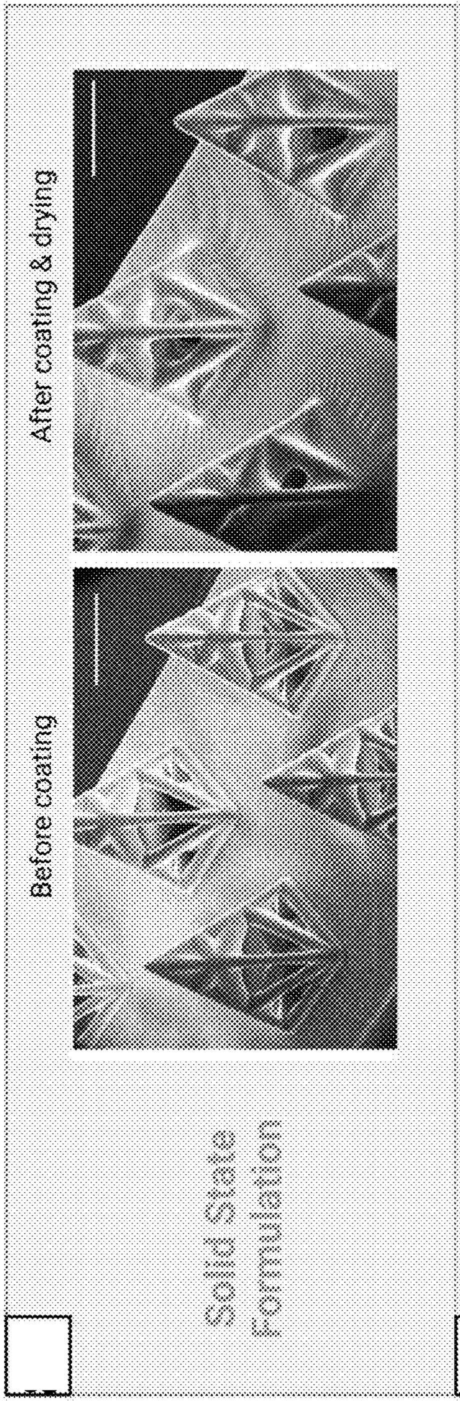
FIG. 8A depicts polymeric microneedles having a solid active agent compound according to certain embodiments.
Figure 8B:
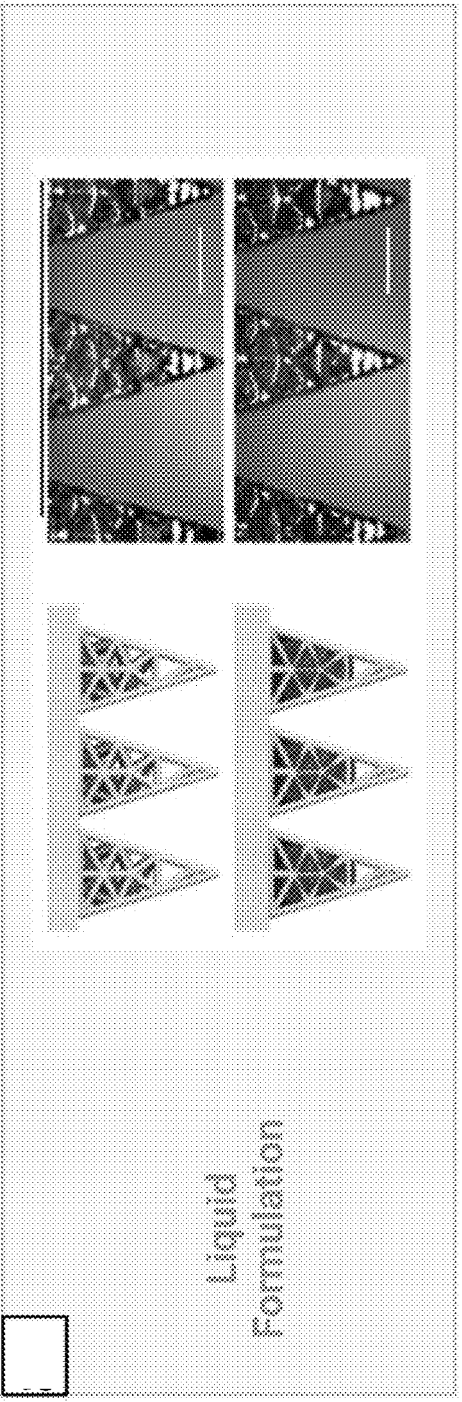
FIG. 8B depicts polymeric microneedles having a liquid active agent compound according to certain embodiments.
Figure 8C:
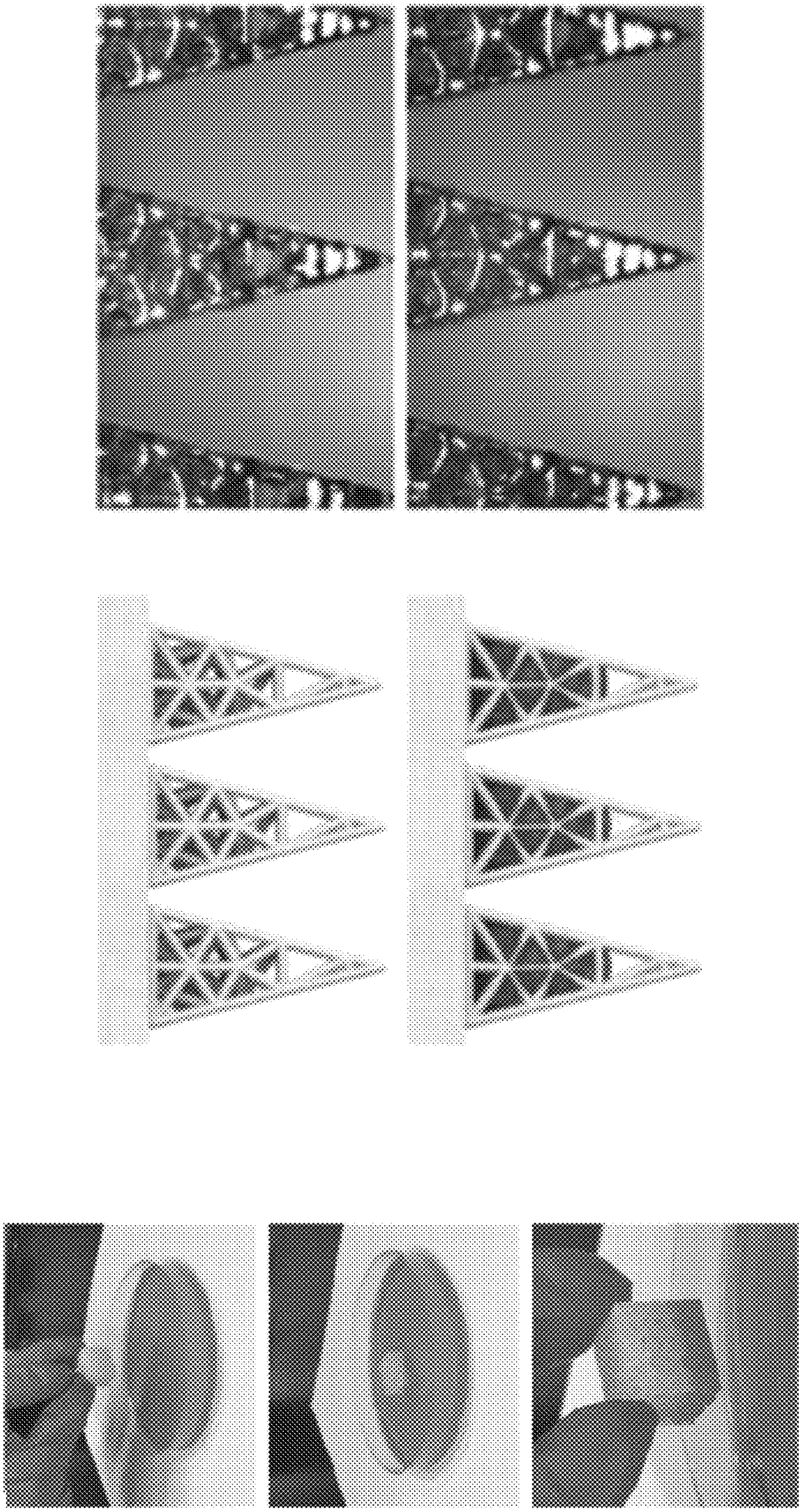
FIG. 8C depicts capillary action by lattice microstructures according to certain embodiments.

In some embodiments, polymeric microneedles also include an active agent compound. The amount of active agent compound that may be incorporated in the lattice microstructures of the polymeric microneedles described herein can vary from picogram levels to milligram levels, depending on the size of microneedles. In some embodiments, the active agent compound is a solid. In some instances where the active agent is a solid, the active is coated (e.g., by spray-coating or dip coating) onto a surface of the lattice microstructure of the polymeric microneedle. In some embodiments, the active agent compound is a liquid. In some instances where the active agent compound is a liquid, the active agent is incorporated into the lattice microstructure by liquid injection or by dip coating. In certain instances, the liquid active agent compound is incorporated into the lattice microstructure by capillary action. FIG. 8A depicts polymeric microneedles having a solid active agent compound according to certain embodiments. The solid active agent compound shown in FIG. 8A is coated onto the surface of the lattice microstructure. FIG. 8B depicts polymeric microneedles having a liquid active agent compound according to certain embodiments. The solid active agent compound shown in FIG. 8B is incorporated into the interior of the lattice microstructure by capillary action. FIG. 8C depicts capillary action by lattice microstructures according to certain embodiments. Polymeric microneedles having a lattice microstructure as described herein are placed in a colored solution. After leaving the lattice microstructure in the colored solution for a period of time, the colored solution fills the interior volume of the lattice microstructure.

Active agent compounds of interest include but are not limited to organic materials such as horseradish peroxidase, phenolsulfonphthalein, nucleotides, nucleic acids (e.g., oligonucleotides, polynucleotides, siRNA, shRNA), aptamers, antibodies or portions thereof (e.g., antibody-like molecules), hormones (e.g., insulin, testosterone), growth factors, enzymes (e.g., peroxidase, lipase, amylase, organophosphate dehydrogenase, ligases, restriction endonucleases, ribonucleases, RNA or DNA polymerases, glucose oxidase, lactase), cells (e.g., red blood cells, stem cells), bacteria or viruses, other proteins or peptides, small molecules (e.g., drugs, dyes, amino acids, vitamins, antioxidants), lipids, carbohydrates, chromophores, light emitting organic compounds (such as luciferin, carotenes) and light emitting inorganic compounds (e.g., chemical dyes and/or contrast enhancing agents such as indocyanine green), immunogenic substances such as vaccines, antibiotics, antifungal agents, antiviral agents, therapeutic agents, diagnostic agents or pro-drugs, analogs or combinations of any of the foregoing.

Examples of immunogenic vaccine substances that can be included in the microneedles described herein include, but are not limited to, those in BIOTHRAX®(anthrax vaccine adsorbed, Emergent Biosolutions, Rockville, Md.); TICE® BCG Live (*Bacillus* Calmette-Guerin for intravesical use, Organon Tekina Corp. LLC, Durham, N.C.); MYCOBAX®

BCG Live (Sanofi Pasteur Inc); DAPTACEL® (diphtheria and tetanus toxoids and acellular pertussis [DTaP] vaccine adsorbed, Sanofi Pasteur Inc.); INFANRIX® (DTaP vaccine adsorbed, GlaxoSmithKline); TRIPEDIA® (DTaP vaccine, Sanofi Pasteur); TRIHIBIT® (DTaP/Hib, sanofi pasteur); KINRIX® (diphtheria and tetanus toxoids, acellular pertussis adsorbed and inactivated poliovirus vaccine, GlaxoSmithKline); PEDIARIX® (DTaP-HepB-IPV, GlaxoSmithKline); PENTACEL® (diphtheria and tetanus toxoids and acellular pertussis adsorbed, inactivated poliovirus and *Haemophilus* b conjugate [tetanus toxoid conjugate] vaccine, sanofi pasteur); Diphtheria and Tetanus Toxoids, adsorbed (for pediatric use, Sanofi Pasteur); DECAVAC® (diphtheria and tetanus toxoids adsorbed, for adult use, Sanofi Pasteur); ACTHIB® (*Haemophilus* b tetanus toxoid conjugate vaccine, Sanofi Pasteur); PEDVAXHIB® (Hib vaccine, Merck); Hiberix (*Haemophilus* b tetanus toxoid conjugate vaccine, booster dose, GlaxoSmithKline); COMVAX® (Hepatitis B-Hib vaccine, Merck); HAVRIX® (Hepatitis A vaccine, pediatric, GlaxoSmithKline); VAQTA® (Hepatitis A vaccine, pediatric, Merck); ENGERIX-B® (Hep B, pediatric, adolescent, GlaxoSmithKline); RECOMBIVAX HB® (hepatitis B vaccine, Merck); TWINRIX®, (HepA/HepB vaccine, 18 years and up, GlaxoSmithKline); CERVARIX® (human papillomavirus bivalent [types 16 and 18] vaccine, recombinant, GlaxoSmithKline); GARDASIL® (human papillomavirus bivalent [types 6, 11, 16 and 18] vaccine, recombinant, Merck); AFLURIA® (Influenza vaccine, 18 years and up, CSL); AGRIFLU™ (influenza virus vaccine for intramuscular injection, Novartis Vaccines); FLUARIX® (Influenza vaccine, 18 years and up, GlaxoSmithKline); FLULAVAL® (Influenza vaccine, 18 years and up, GlaxoSmithKline); FLUVIRIN® (Influenza vaccine, 4 years and up, Novartis Vaccine); FLUZONE® (Influenza vaccine, 6 months and up, Sanofi Pasteur); FLUMIST® (Influenza vaccine, 2 years and up, MedImmune); IPOL® (e-IPV polio vaccine, sanofi Pasteur); JE VAX® (Japanese encephalitis virus vaccine inactivated, BIKEN, Japan); IXIARO® (Japanese encephalitis virus vaccine inactivated, Novartis); MENACTRA® (Meningococcal [Groups A, C, Y and W-135] and diphtheria vaccine, Sanofi Pasteur); MENOMUNE@-A/C/Y/W-135 (Meningococcal polysaccharide vaccine, sanofi pasteur); MMRII® (MMR vaccine, Merck); MENVEO® (Meningococcal [Groups A, C, Y and W-135] oligosaccharide diphtheria CRM 197 conjugate vaccine, Novartis Vaccines); PROQUAD® (MMR and varicella vaccine, Merck); PNEUMOVAX 23® (pneumococcal polysaccharide vaccine, Merck); PREVNAR® (pneumococcal vaccine, 7-valent, Wyeth/Lederle); PREVNAR-13® (pneumococcal vaccine, 13-valent, Wyeth/Lederle); POLIO VAX™ (poliovirus inactivated, sanofi pasteur); IMOVAX® (Rabies vaccine, Sanofi Pasteur); RABAVERT™ (Rabies vaccine, Chiron); ROTATEQ® (Rotavirus vaccine, live, oral pentavalent, Merck); ROTARIX® (Rotavirus, live, oral vaccine, GlaxoSmithKline); DECAVAC™ (tetanus and diphtheria toxoids vaccine, sanofi pasteur); Td (generic) (tetanus and diphtheria toxoids, adsorbed, Massachusetts Biol. Labs); TYPHIMV1® (typhoid Vi polysaccharide vaccine, Sanofi Pasteur); ADACEL® (tetanus toxoid, reduced diphtheria toxoid and acellular pertussis, sanofi pasteur); BOOSTRIX® (tetanus toxoid, reduced diphtheria toxoid and acellular pertussis, GlaxoSmithKline); VIVOTIF® (typhoid vaccine live oral Ty21a, Bema Biotech); ACAM2000™ (Smallpox (vaccinia) vaccine, live, Acambis, Inc.); DRYVAX® (Smallpox (vaccinia) vaccine); VARIVAX® (varicella [live] vaccine, Merck); YF-VAX® (Yellow fever vaccine, Sanofi Pasteur); ZOSTAVAX®, (Varicella zoster, Merck); or combinations thereof. Any vaccine products listed in database of Center for Disease Control and Prevention (CDC) can also be included in the compositions described herein.

The term small molecule is used herein in its conventional sense to refer to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. The term "antibiotic" is used herein to describe a compound that acts as an antimicrobial, bacteriostatic, or bactericidal agent. Example antibiotics include, but are not limited to, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, and sulfamethoxazole.

In some embodiments, the active agent compound includes but is not limited to steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzino statin chromophore, and kedarcidin chromophore), heavy metal complexes e.g., cisplatin), hormone antagonists (e.g., tamoxifen), non-specific (non-antibody) proteins (e.g., sugar oligomers), oligonucleotides antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

In certain embodiments, the polymeric microneedles include active agent compounds selected from acetaminophen, non-steroidal anti-inflammatory medications (NSAIDs), corticosteroids; narcotics; anti-convulsants; local anesthetics, and any combinations thereof. In various aspects of the microneedles provided herein include, but not limited to, ibuprofen, naproxin, aspirin, fenoprofen, flurbiprofen, ketoprofen, oxaprozin, diclofenac sodium, etodolac, indomethacin, ketorolac, sulindac, tolmetin, meclofenamate, mefenamic acid, nabumetone, piroxicam and COX-2 inhibitors. In some instances, the pain medications can include acetaminophen combinations (e.g., acetaminophen with a narcotic) such as acetaminophen with codeine; acetaminophen with hydrocodone; and acetaminophen with oxycodone.

In some instances, the active agent compound is coated onto one or more surfaces of the microneedle. In some instances, the active agent compound is coated onto a tip section of the microneedle. In some instances, the active agent compound is coated onto a body section of the microneedle. In some instances, the active agent compound is coated onto a base section of the microneedle. In some embodiments, the active agent compound is contained within the lattice microstructure of the polymeric microneedle. In some embodiments, the active agent compound fills 1% or more of the void volume of the lattice microstructure, such as 2% or more, such as 3% or more, such as 4% or more, such as 5% or more, such as 6% or more, such as 7% or more, such as 8% or more, such as 9% or more, such as 10% or more, such as 15% or more, such as 20% or more, such as 25% or more and including 50% or more of the void volume of the lattice microstructure. In some embodiments, each polymeric microneedle contains 0.01 μL or more of the active agent compound, such as 0.05 μL or more, such as 0.1 μL or more, such as 0.2 μL or more, such as 0.3 μL or more, such as 0.4 μL, such as 0.5 μL or more, such as 1 μL or more, such as 2 μL or more, such as 3 μL or more, such as 4 μL or more, such as 5 μL and including 10 μL or more of the active agent compound.

In certain embodiments, the active agent compound further includes one or more excipients, such as one or more pharmaceutically acceptable excipients. In certain embodiments, the excipients include a stabilizing excipient. In certain instances, the excipient allows for dissolution of the active agent compound. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For example, the one or more excipients may include sucrose, starch, mannitol, sorbitol, lactose, glucose, cellulose, talc, calcium phosphate or calcium carbonate, a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

The active agent compound may be formulated into pharmaceutical compositions by combination with appropriate, pharmaceutically acceptable carriers or diluents, and may be formulated into preparations in solid, semi-solid, liquid or gaseous forms, such as powders, granules, solutions, injections, inhalants. In certain embodiments, the active agent compound is formulated for injection. For example, compositions of interest may be formulated for interstitial or dermal administration.

In pharmaceutical dosage forms, the active agent compound may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, compositions of interest include an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. In some instances, compositions of interest further include a preservative. Suitable preservatives include, but are not limited to, a benzyl alcohol, phenol, chlorobutanol, benzalkonium chloride, and the like. In many cases, the composition is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, compositions include other additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Where the composition is formulated for injection (subcutaneous or dermal injection), the active agent compound may be formulated by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Patches Having a Plurality of Polymeric Microneedles

Aspects of the disclosure also include patches having a backing layer and a plurality of polymeric microneedles (as described in detail above) in contact with the backing layer. In some embodiments, patches provide for transdermal administration of one or more active agent compounds. In other embodiments, patches may be employed to collect a biological fluid sample by applying the patch to a skin surface of the subject. The term "transdermal" is used in its conventional sense to refer to the route of administration where an active agent (i.e., drug) is delivered across the skin (e.g., topical administration) or mucous membrane or where a biological sample such as interstitial fluid is collected from the subject (e.g., for analyte detection in the biological sample).

In embodiments, patches include a plurality of polymeric microneedles. In some embodiments, patches include 5 microneedles or more, such as 10 microneedles or more, such as 15 microneedles or more, such as 20 microneedles or more, such as 25 microneedles or more, such as 50 microneedles or more, such as 100 microneedles or more, such as 250 microneedles or more, such as 500 microneedles or more and including 1000 microneedles or more. In some embodiments, the plurality of microneedles form an array of microneedles on the backing layer. In some instances, the polymeric microneedles are arranged on the backing layer in one or more lines. For example, the polymeric microneedles may be positioned along 2 or more parallel lines, such as 3 or more, such as 4 or more, such as 5 or more, such as 6 or more, such as 7 or more, such as 8 or more, such as 9 or more, such as 10 or more, such as 15 or more, such as 20 or more and including 25 or more parallel lines of microneedles. In certain instances, the polymeric microneedles are arranged into a geometric configuration, where arrangements of interest include, but are not limited to a square configuration, rectangular configuration, trapezoidal configuration, triangular configuration, hexagonal configuration, heptagonal configuration, octagonal configuration, nonagonal configuration, decagonal configuration, dodecagonal configuration, circular configuration, oval configuration as well as irregular shaped configurations.

In some embodiments, the microneedles are separated from each other on the backing layer by an average distance of from 1 μm to 1000 μm, such as from 2 μm to 950 μm, such as from 3 μm to 900 μm, such as from 4 μm to 850 μm, such as from 5 μm to 800 μm, such as from 6 μm to 750 μm, such as from 7 μm to 700 μm, such as from 8 μm to 650 μm, such as from 9 μm to 600 μm, such as from 10 μm to 550 μm, such as from 15 μm to 500 μm, such as from 20 μm to 450 μm and including from 25 μm to 400 μm. The plurality of polymeric microneedles may each be the same size or patches may include plurality of polymeric microneedles having different sizes. Each polymeric microneedle independently may have a length of from 50 μm to 2000 μm, such as from 75 μm to 1950 μm, such as from 100 μm to 1900 μm, such as from 125 μm to 1850 μm, such as from 150 μm to 1800 μm, such as from 175 μm to 1750 μm, such as from 200 μm to 1700 μm, such as from 225 μm to 1650 μm, such as from 250 μm to 1600 μm, such as from 275 μm to 1550 μm and including from 300 μm to 1500 μm. Each polymeric microneedle independently may have a width (diameter when the polymeric microneedle has a circular cross-section) of from 50 μm to 1000 μm, such as from 75 μm to 950 μm, such as from 100 μm to 900 μm, such as from 125 μm to 850 μm, such as from 150 μm to 800 μm, such as from 175 μm to 750 μm, such as from 200 μm to 700 μm, such as from 225 μm to 650 μm, such as from 250 μm to 600 μm, such as from 275 μm to 550 μm and including from 300 μm to 500 μm.

The plurality of polymeric microneedles may each have lattice microstructures that are the same shape or patches may include plurality of polymeric microneedles having lattice microstructures with different shapes. In some embodiments, patches include microneedles having different lattice shapes such as where the patch include one or more microneedles with a lattice microstructure having a tetrahedral lattice shape, one or more microneedles with a lattice microstructure having a Kagome lattice shape, one or more microneedles with a lattice microstructure having a rhombic lattice shape, one or more microneedles with a lattice microstructure having an icosahedral lattice shape, one or more microneedles with a lattice microstructure having a Voronoi lattice shape or one or more microneedles with a lattice microstructure having a triangular lattice shape. In some instances, patches have microneedles that have 2 or more different lattice shapes, such as 3 or more different lattice shapes. In certain instances, one or more of the microneedles of the patch have different lengths or different base widths. In certain embodiments, one or more of the microneedles of the patch have different mechanical integrity (e.g., can withstand different load bearings). In certain embodiments, patches of interest include one or more dynamic microneedles, such as one or more microneedles which can alter geometry or shape, one or more microneedles which exhibit motion through elastic deformation or one or more microneedles which deploy a barb structure.

In certain embodiments, patches include one or more polymeric microneedles that include an active agent compound, such as where 1% or more of the polymeric microneedles of the patch include an active agent compound, such as 2% or more, such as 3% or more, such as 4% or more, such as 5% or more, such as 10% or more, such as 15% or more, such as 20% or more, such as 25% or more, such as 50% or more, such as 75% or more, such as 90% or more, such as 95% or more, such as 97% or more and including where 99% or more of the plurality of polymeric microneedles of the patch include an active agent compound. Active agents of interest are described in detail above. In some instances, the active agent compound is a small molecule active agent. In some instances, the active agent compound is an immunogenic active agent, such as a vaccine.

In some instances, the active agent compound is coated onto a surface of one or more of the plurality of microneedles. In some instances, the active agent compound is coated onto a tip section of one or more of the plurality of microneedles. In some instances, the active agent compound is coated onto a body section of one or more of the plurality of microneedles. In some instances, the active agent compound is coated onto a base section of one or more of the plurality of microneedles. In some embodiments, the active agent compound is contained within the lattice microstructure of one or more of the plurality of microneedles. In some embodiments, the active agent compound fills 1% or more of the void volume of the lattice microstructure, such as 2% or more, such as 3% or more, such as 4% or more, such as 5% or more, such as 6% or more, such as 7% or more, such as 8% or more, such as 9% or more, such as 10% or more, such as 15% or more, such as 20% or more, such as 25% or more and including 50% or more of the void volume of the lattice microstructure. In some embodiments, each polymeric microneedle independently contains 0.01 μL or more of the active agent compound, such as 0.05 μL or more, such as 0.1 μL or more, such as 0.2 μL or more, such as 0.3 μL or more, such as 0.4 μL, such as 0.5 μL or more, such as 1 μL or more, such as 2 μL or more, such as 3 μL or more, such as 4 μL or more, such as 5 μL and including 10 μL or more of the active agent compound.

In some embodiments, the polymeric microneedles are configured to release active agent compound from the lattice microstructure over a period of time of 0.01 hours or more, such as over 0.05 hours or more, such as over 0.1 hours or more, such as over 0.5 hours or more, such as over 1 hour or more, such as over 2 hours or more, such as over 6 hours or more, such as over 12 hours or more, such as over 18 hours or more, such as over 24 hours or more, such as over 36 hours or more, such as over 48 hours or more, such as over 72 hours or more, such as over 96 hours or more, such as over 120 hours or more, such as over 144 hours or more and including over 168 hours or more. In certain instances, active agent compound is released from the microneedles upon insertion or over a period of time, such as where the active agent compound is released from the microneedle over a time period of about 1 minute to about 6 months, over a time period of about 1 minute to about 3 months, over a time period of about 1 minute to about 1 month, over a time period of about 1 minute to about 2 weeks, over a time period of about 1 minute to about 1 week, over a time period of about 1 minute to about 3 days, over a time period of about 1 minute to about 1 day, over a time period of about 1 minute to about 12 hours, over a time period of about 1 minute to about 6 hours, over a time period of about 1 minute to about 1 hour, over a time period of about 1 minute to about 30 minutes, over a time period of about 30 minutes to about 6 months, over a time period of about 1 hour to about 6 months, over a time period of about 6 hours to about 6 months, over a time period of about 12 hours to about 6 months, over a time period of about 1 day to about 6 months, over a time period of about 3 days to about 6 months, over a time period of about 1 week to about 6 months, over a time period of about 2 weeks to about 6 months, over a time period of about 1 month to about 6 months, or over a time period of about 3 months to about 6 months. In certain embodiments, the active agent compound is released from the microneedle over a time period of less than about 1 minute, over a time period of about 1 second to about 1 minute, over a time period of about 1 second to about 30 seconds, over a time period of about 1 second to about 10 seconds, over a time period of about 10 seconds to about 1 minute or over a time period of about 30 seconds to about 1 minute.

In some instances, patches include polymeric microneedles that are configured for collecting a biological fluid sample from a subject. In some embodiments, the polymeric microneedle is configured to wick biological fluid into the microneedle such as through capillary action. Depending on the size of the lattice microstructure, the polymeric microneedle may be configured to collect 0.01 μL or more of the biological fluid, such as 0.05 μL or more, such as 0.1 μL or more, such as 0.2 μL or more, such as 0.3 μL or more, such as 0.4 μL, such as 0.5 μL or more, such as 1 μL or more, such as 2 μL or more, such as 3 μL or more, such as 4 μL or more, such as 5 μL and including 10 μL or more of the biological fluid. The biological fluid may be collected into the polymeric microneedle over a period of time of 1 second or more, such as 5 seconds or more, such as 10 seconds or more, such as 15 seconds or more, such as 30 seconds or more, such as 1 minute or more, such as 5 minutes or more, such as 10 minutes or more, such as 15 minutes or more, such as 30 minutes or more, such as 1 hour or more, such as 2 hours or more, such as 3 hours or more, such as 6 hours or more, such as 12 hours or more, such as 18 hours or more and including over a period of time of 24 hours or more.

In certain embodiments, patches as described above further include a backing layer. The backing layer may be flexible, such as so that it can be brought into close contact with the desired application site on the subject. The backing may be fabricated from a material that does not absorb the active agent compound or biological fluid collected from a subject into the microneedles, and does not allow the active agent compound to be leached from the interior of the lattice microstructure of the polymeric microneedles. Backing layers of interest may include, but are not limited to, non-woven fabrics, woven fabrics, films (including sheets), porous bodies, foamed bodies, paper, composite materials obtained by laminating a film on a non-woven fabric or fabric, and combinations thereof.

Non-woven fabric may include polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include cotton, rayon, polyacrylic resins, polyester resins, polyvinyl alcohol, and combinations thereof. Films may include polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Papers may include impregnated paper, coated paper, wood free paper, Kraft paper, Japanese paper, glassine paper, synthetic paper, and combinations thereof.

Depending on the size of the patches, the size of the backing may vary, and in some instances sized to cover the entire application site on the subject. As such, the backing layer may have a length ranging from 2 to 100 cm, such as 4 to 60 cm and a width ranging from 2 to 100 cm, such as 4 to 60 cm. In certain instances, the backing layer may insoluble in water. By insoluble in water is meant that that the backing layer may be immersed in water for a period of 1 day or longer, such as 1 week or longer, including 1 month or longer, and exhibit little if any dissolution, e.g., no observable dissolution.

In certain embodiments, patches of interest include a pressure sensitive adhesive, such as for maintaining the patch in contact with the skin surface of a subject for an extended period of time. Pressure sensitive adhesives may include, but are not limited to, poly-isobutene adhesives, poly-isobutylene adhesives, poly-isobutene/polyisobutylene adhesive mixtures, carboxylated polymers, acrylic or acrylate copolymers, such as carboxylated acrylate copolymers.

Where the pressure sensitive adhesive includes polybutene, the polybutene may be saturated polybutene. Alternatively, the polybutene may be unsaturated polybutene. Still further, the polybutene may be a mixture or combination of saturated polybutene and unsaturated polybutene. In some embodiments, the pressure sensitive adhesive may include a composition that is, or is substantially the same as, the composition of Indopol® L-2, Indopol® L-3, Indopol® L-6, Indopol® L-8, Indopol® L-14, Indopol® H-7, Indopol® H-8, Indopol® H-15, Indopol® H-25, Indopol® H-35, Indopol® H-50, Indopol® H-100, Indopol® H-300, Indopol® H-1200, Indopol® H-1500, Indopol® H-1900, Indopol® H-2100, Indopol® H-6000, Indopol® H-18000, Panalane® L-14E, Panalane® H-300E and combinations thereof. In certain embodiments, the polybutene pressure-sensitive adhesive is Indopol® H-1900. In other embodiments, the polybutene pressure-sensitive adhesive is Panalane® H-300E.

Acrylate copolymers of interest include copolymers of various monomers, such as "soft" monomers, "hard" monomers or "functional" monomers. The acrylate copolymers can be composed of a copolymer including bipolymer (i.e., made with two monomers), a terpolymer (i.e., made with three monomers), or a tetrapolymer (i.e., made with four monomers), or copolymers having greater numbers of monomers. The acrylate copolymers may be crosslinked or non-crosslinked. The polymers can be cross-linked by known methods to provide the desired polymers. The monomers from of the acrylate copolymers may include at least two or more exemplary components selected from the group including acrylic acids, alkyl acrylates, methacrylates, copolymerizable secondary monomers or monomers with functional groups. Monomers ("soft" and "hard" monomers) may be methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989), the disclosure of which is herein incorporated by reference. In some embodiments, the pressure sensitive adhesive is an acrylate-vinyl acetate copolymer. In some embodiments, the pressure sensitive adhesive may include a composition that is, or is substantially the same as, the composition of Duro-Tak® 87-9301, Duro-Tak® 87-200A, Duro-Tak® 87-2353, Duro-Tak® 87-2100, Duro-Tak® 87-2051, Duro-Tak®87-2052, Duro-Tak® 87-2194, Duro-Tak® 87-2677, Duro-Tak® 87-201A, Duro-Tak® 87-2979, Duro-Tak® 87-2510, Duro-Tak® 87-2516, Duro-Tak® 87-387, Duro-Tak® 87-4287, Duro-Tak® 87-2287, and Duro-Tak® 87-2074 and combinations thereof. The term "substantially the same" as used herein refers to a composition that is an acrylate-vinyl acetate copolymer in an organic solvent solution. In certain embodiments, the acrylic pressure-sensitive adhesive is Duro-Tak® 87-2054.

In some embodiments, one or more of the polymeric microneedles of the patches dissolvable. In some instances, the entire microneedle is dissolvable. In other instances, a portion of the microneedle is dissolvable such as, for example, the tip of the microneedle. In some embodiments, the microneedles dissolve at a rate of from about one minute per patch to about two weeks per patch, from about one minute per patch to about one week per patch, from about one minute per patch to about 3 days per patch, from about one minute per patch to about one day per patch, from about one minute per patch to about 12 hours per patch, from about one minute per patch to about 6 hours per patch, from about one minute per patch to about one hour per patch, from about one minute per patch to about 30 minutes per patch, from about 30 minutes per patch to about one month per patch, from about one hour per patch to about one month per patch, from about 6 hours per patch to about one month per patch, from about 12 hours per patch to about one month per patch, from about one day per patch to about one month per patch, from about 3 days per patch to about one month per patch, from about one week per patch to about one month per patch and including from about two weeks per patch to about one month per patch.

In some embodiments, one or more of the polymeric microneedles are breakable. In some instances, the polymeric microneedle is breakable due to the shape of the microneedle (e.g., due to the presence of holes or a thinner structure). In some instances, the polymeric microneedle is breakable due to a difference in the mechanical properties of the support, as compared to the remainder of the microneedle. A breakable microneedle may be broken intentionally to remove the microneedles embedded in the skin from the patch backing on the skin surface. In certain embodiments, removal of the patch backing may allow for verification that the intended payload is delivered to the sample and/or subject by ensuring that none of the active agent compound is present on the breakable support after patch administration.

In certain embodiments, one or more of the polymeric microneedles includes a breakable support. In some instances, the microneedle sidewall includes a breakable support. For example, the support may resist breaking under application of a normal force, but allow separation through torsion, shearing, or other energy inputs. In some instances, the microneedle includes a breakable perforation, such as, for example, a physical perforation or a chemical perforation. In certain instances, the microneedle includes a perforated sidewall. The term "perforation" is used herein in its conventional sense to refer to a specific plane within the microneedle that is chemically or physically distinct from the remainder of the array. In this way, one part of the microneedle (e.g., the tip) may be separated from the rest of the microneedle (e.g., the base). In some instances, a perforation includes a hole or slit.

In some embodiments, polymeric microneedles that can be mechanically or chemically fragmented or removed provide for rapid administration of active agent compounds that have long term drug release without the long term patch application. For example, if the patch releases active agent compound over a period of one week, breakable microneedles could be applied to the skin, fragmented, and the patch backing removed, with the microneedle fragments embedded in the skin to release drug. This could afford patients the benefit of long-term drug delivery without the need to wear a patch for the entire duration of therapy.

Methods for Applying a Patch Having a Plurality of Polymeric Microneedles

Aspects of the present disclosure also include methods for applying a patch having a plurality of polymeric microneedles to a skin surface of a subject. In some embodiments, applying the patches described herein provide for transdermal administration of one or more active agent compounds. In some embodiments, patches may be employed to collect a biological fluid sample by applying the patch to a skin surface of the subject. Transdermal refers to the route of administration where an active agent (i.e., drug) is delivered across the skin (e.g., topical administration) or mucous membrane or where a biological sample such as interstitial fluid is collected from the subject. As such, patches as described herein are configured to deliver an active agent compound or collect a biological sample from the subject through one or more of the subcutis, dermis and epidermis, including the stratum corneum, stratum germinativum, stratum *spinosum* and stratum basale. Accordingly, the patches containing the plurality of polymeric microneedles may be applied at any convenient location, such as for example, the arms, legs, buttocks, abdomen, back, neck, scrotum, vagina, face, behind the ear, buccally as well as sublingually. In describing methods of the present invention, the term "subject" is meant the person or organism to which the patch is applied and maintained in contact. As such, subjects of the invention may include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

In some embodiments, methods include extended delivery of an active agent compound to the subject. By "extended delivery" is meant that the patch is configured to provide for administration of the active agent compound over an extended period of time, such as over the course of hours, days and including weeks, including 1 hour or longer, such as 2 hours or longer, such as 4 hours or longer, such as 8 hours or longer, such as 12 hours or longer, such as 24 hours or longer, such as 48 hours or longer, such as 72 hours or longer, such as 96 hours or longer, such as 120 hours or longer, such as 144 hours or longer and including 168 hours or longer. In some embodiments, the polymeric microneedles are configured for sustained release of the active agent compound and includes multi-day delivery of a therapeutically effective amount of the active agent compound. By multi-day delivery is meant that the polymeric microneedles of the patches are formulated to provide a therapeutically effective amount of the active agent compound to a subject when applied to the skin of a subject for a period of time that is 1 day or longer, such as 2 days or longer, such as 4 days or longer, such as 7 days or longer, such as 14 days and including 30 days or longer. In certain embodiments, patches provide a therapeutically effective amount of the active agent compound to a subject for a period of 10 days or longer. For multi-day administration, an upper limit period of time is, in some instances, 30 days or shorter, such as 28 days or shorter, such as 21 days or shorter, such as 14 days or shorter, such as 7 days or shorter and including 3 days or shorter. In certain embodiments, multi-day delivery ranges such as from 2 days to 30 days, such as from 3 days to 28 days, such as from 4 days to 21 days, such as from 5 days to 14 days and including from 6 days to 10 days.

In certain embodiments, protocols may include multiple dosage intervals. By "multiple dosage intervals" is meant more than one patch is applied and maintained in contact with the subject in a sequential manner. As such, a patch is removed from contact with the subject and a new patch is reapplied to the subject. In practicing methods of the invention, treatment regimens may include two or more dosage intervals, such as three or more dosage intervals, such as four or more dosage intervals, such as five or more dosage intervals, including ten or more dosage intervals.

The duration between dosage intervals in a multiple dosage interval treatment protocol may vary, depending on the physiology of the subject or by the treatment protocol as determined by a health care professional. For example, the duration between dosage intervals in a multiple dosage treatment protocol may be predetermined and follow at regular intervals. As such, the time between dosage intervals may vary and may be 1 day or longer, such as 2 days or longer, such as 3 days or longer, such as 4 days or longer, such as 5 days or longer, such as 6 days or longer, such as 7 days or longer, such as 10 days or longer, including 30 days or longer. An upper limit period of time between dosage intervals is, in some instances, 30 days or shorter, such as 28 days or shorter, such as 21 days or shorter, such as 14 days or shorter, such as 7 days or shorter and including 3 days or shorter. In certain embodiments, the time between dosage intervals ranges such as from 2 days to 30 days, such as from 3 days to 28 days, such as from 4 days to 21 days, such as from 5 days to 14 days and including from 6 days to 10 days.

In certain embodiments, methods further include the step of removing the patch from contact with the subject at the conclusion of a dosage interval. For example, the patch may be removed from contact with the subject after maintaining the patch in contact with the subject for 0.5 hours or more, such as 1 hour or more, such as 2 hours or more, such as 4 hours or more, such as 8 hours or more, such as 12 hours or more, such as 24 hours or more, such as 36 hours or more, such as 48 hours or more, such as 60 hours or more, such as 72 hours or more, such as 96 hours or more, such as 120 hours or more, including 144 hours or more, and including 168 hours or more. An upper limit for the amount of time the patch is maintained in contact with a subject before removal is, in some instances, 168 hours or shorter, such as 144 hours or shorter, such as 120 hours or shorter, such as 96 hours or shorter, such as 72 hours or shorter, such as 48 hours or shorter, such as 24 hours or shorter, such as 12 hours or shorter, such as 8 hours or shorter, such as 4 hours or shorter and including 2 hours or shorter.

The location on the subject for reapplying subsequent patches in multiple dosage treatment regimens may be the same or different from the location on the subject where the previous patch was removed. For example, if a first patch is applied and maintained on the leg of the subject, one or more subsequent patches may be reapplied to the same position on the leg of the subject. On the other hand, if a first patch was applied and maintained on the leg of the subject, one or more subsequent patches may be reapplied to a different position, such as the abdomen or back of the subject. Subsequent dosages applied in multiple dosage interval regimens may have the same or different active agent compound. In certain instances, a subsequent dosage interval in a treatment regimen may contain a higher or lower concentration of active agent compound than the previous dosage interval. For example, the concentration of the active agent compound may be increased in subsequent dosage intervals by 10% or greater, such as 20% or greater, such as 50% or greater, such as 75% or greater, such as 90% or greater and including 100% or greater. An upper limit for the increase in concentration of active agent compound in subsequent dosage intervals is, in some instances, 10-fold or less, such as 5-fold or less, such as 2-fold or less, such as 1-fold or less, such as 0.5-fold or less and including 0.25-fold or less.

On the other hand, the amount of active agent compound may be decreased in subsequent dosage intervals, such as by 10% or greater, such as 20% or greater, such as 50% or greater, such as 75% or greater, such as 90% or greater and including 100% or greater. An upper limit for the decrease in amount of the active agent compound in subsequent dosage intervals is, in some instances, 10-fold or less, such as 5-fold or less, such as 2-fold or less, such as 1-fold or less, such as 0.5-fold or less and including 0.25-fold or less. In other instances, a subsequent dosage interval may contain a different active agent compound than the previous dosage interval.

In some embodiments, methods include applying one or more patches to a skin surface of a subject in a manner to collect a biological fluid sample from the subject. The biological fluid sample may be collected into the polymeric microneedles of the patches by any convenient protocol, such as for example by capillary action. In embodiments, the biological fluid sample is collected from one or more of the subcutis, dermis and epidermis, including the stratum corneum, stratum germinativum, stratum *spinosum* and stratum basale of the subject. In certain instances, the biological fluid sample is interstitial fluid. In certain instances, the biological fluid sample is dermal fluid. In certain instances, the biological fluid sample is blood. In some embodiments, methods include collecting a biological fluid sample from the subject (e.g., interstitial fluid, dermal fluid) for detecting an analyte present in the biological sample, such as for detecting glucose.

In some embodiments, the patch is maintained in contact with the subject for an extended period of time sufficient to collect biological fluid sample from the subject, such as over the course of hours, days and including weeks, including 1 hour or longer, such as 2 hours or longer, such as 4 hours or longer, such as 8 hours or longer, such as 12 hours or longer, such as 24 hours or longer, such as 48 hours or longer, such as 72 hours or longer, such as 96 hours or longer, such as 120 hours or longer, such as 144 hours or longer and including 168 hours or longer. In some embodiments, the polymeric microneedles are configured for multi-day collection of the biological fluid sample. By multi-day collection is meant that the polymeric microneedles of the patches are configured to continuously or in predetermined intervals collect biological sample from a subject when applied to the skin of a subject for a period of time that is 1 day or longer, such as 2 days or longer, such as 4 days or longer, such as 7 days or longer, such as 14 days and including 30 days or longer. In certain embodiments, patches are maintained in contact with the subject for a period of 10 days or longer. For multi-day collection of biological samples, an upper limit period of time is, in some instances, 30 days or shorter, such as 28 days or shorter, such as 21 days or shorter, such as 14 days or shorter, such as 7 days or shorter and including 3 days or shorter. In certain embodiments, multi-day transdermal delivery ranges such as from 2 days to 30 days, such as from 3 days to 28 days, such as from 4 days to 21 days, such as from 5 days to 14 days and including from 6 days to 10 days.

In certain embodiments, protocols may include multiple collection intervals. By "multiple collection intervals" is meant more than one patch is applied and maintained in contact with the subject in a sequential manner. As such, a patch is removed from contact with the subject and a new patch is reapplied to the subject. In practicing methods of the invention, treatment regimens may include two or more collection intervals, such as three or more collection intervals, such as four or more collection intervals, such as five or more collection intervals, including ten or more collection intervals.

The duration between collection intervals in a multiple collection interval treatment protocol may vary, depending on the physiology of the subject or by the treatment protocol as determined by a health care professional. For example, the duration between collection intervals in a multiple collection protocol may be predetermined and follow at regular intervals. As such, the time between collection intervals may vary and may be 1 day or longer, such as 2 days or longer, such as 3 days or longer, such as 4 days or longer, such as 5 days or longer, such as 6 days or longer, such as 7 days or longer, such as 10 days or longer, including 30 days or longer. An upper limit period of time between collection intervals is, in some instances, 30 days or shorter, such as 28 days or shorter, such as 21 days or shorter, such as 14 days or shorter, such as 7 days or shorter and including 3 days or shorter. In certain embodiments, the time between collection intervals ranges such as from 2 days to 30 days, such as from 3 days to 28 days, such as from 4 days to 21 days, such as from 5 days to 14 days and including from 6 days to 10 days.

In certain embodiments, methods further include the step of removing the patch from contact with the subject at the conclusion of a collection interval. For example, the patch may be removed from contact with the subject after maintaining the patch in contact with the subject for 0.5 hours or more, such as 1 hour or more, such as 2 hours or more, such as 4 hours or more, such as 8 hours or more, such as 12 hours or more, such as 24 hours or more, such as 36 hours or more, such as 48 hours or more, such as 60 hours or more, such as 72 hours or more, such as 96 hours or more, such as 120 hours or more, including 144 hours or more, and including 168 hours or more. An upper limit for the amount of time the patch is maintained in contact with a subject before removal is, in some instances, 168 hours or shorter, such as 144 hours or shorter, such as 120 hours or shorter, such as 96 hours or shorter, such as 72 hours or shorter, such as 48 hours or shorter, such as 24 hours or shorter, such as 12 hours or shorter, such as 8 hours or shorter, such as 4 hours or shorter and including 2 hours or shorter.

Patches having a plurality of polymeric microneedles according to embodiments of the invention are non-irritable to the skin of the subject at the site of application. Irritation of the skin is referred to herein in its general sense to refer to adverse effects, discoloration or damage to the skin, such as for example, redness, pain, swelling or dryness. As such, in practicing methods with the subject patches the quality of the skin remains normal and is consistent throughout the entire dosage or collection interval.

In some embodiments, skin irritation is evaluated to determine the quality and color of the skin at the application site and to determine whether any damage, pain, swelling or dryness has resulted from maintaining the patch in contact with the subject. The skin may be evaluated for irritation by any convenient protocol, such as for example using the Draize scale, as disclosed in Draize, J. H., *Appraisal of the Safety of Chemicals in Foods, Drugs and Cosmetics*, pp. 46-49, The Association of Food and Drug Officials of the United States: Austin, Texas, the disclosure of which is herein incorporated by reference. In particular, the skin may be evaluated at the patch application site for erythema or edema. For example, grades for erythema and edema may be assigned based on visual observation or palpation:

Erythema: 0=no visible redness; 1=very slight redness (just perceptible);
- 2=slight but defined redness; 3=moderately intense redness;
- 4=severe erythema (dark red discoloration of the skin)
- 5=eschar formation Edema: 0=no visible reactions or swelling; 1=very mild edema (just perceptible swelling); 2=mild edema (corners of area are well defined due to swelling); 3=moderate edema (up to 1 mm swelling); 4=severe edema (more than 1 mm swelling).

The site of application may be evaluated for skin irritation at any time during the subject methods. In some instances, the skin is evaluated for irritation while maintaining the patch in contact with the subject by observing or palpating the skin at regular intervals, e.g., every 0.25 hours, every 0.5 hours, every 1 hour, every 2 hours, every 4 hours, every 12 hours, every 24 hours, including every 72 hours, or some other interval. For instance, the site of application may be evaluated for skin irritation while maintaining the patch in contact with the subject, such as 15 minutes after applying the patch to the subject, 30 minutes after applying the patch, 1 hour after applying the transdermal delivery device, 2 hours after applying the patch, 4 hours after applying the patch, 8 hours after applying the patch, 12 hours after applying the patch, 24 hours after applying the patch, 48 hours after applying the patch, 72 hours after applying the patch, 76 hours after applying the patch, 80 hours after applying the patch, 84 hours after applying the patch, 96 hours after applying the patch, 120 hours after applying the patch, including 168 hours after applying the patch.

Systems for Making a Polymeric Microneedle

Aspects of the present disclosure also include systems for making a polymeric structure having a lattice microstructure with one or more lattice cell units, such as a polymeric microneedle. Systems according to certain embodiments include a micro-digital light projection system having a light beam generator component and a light projection monitoring component and a liquid interface polymerization module that includes a build elevator and a build surface configured for generating the lattice microstructure from a polymerizable composition positioned therebetween.

In some embodiments, the light beam generator component includes a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, a multi-LED integrated white light source, among other broadband light sources or any combination thereof.

In some embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof. The subject systems may include one or more light sources, as desired, such as two or more light sources, such as three or more light sources, such as four or more light sources, such as five or more light sources and including ten or more light sources. The light source may include a combination of types of light sources, for example, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., a narrow band visible light or near-IR LED). In yet other instances, the light source is an plurality of narrow band light sources each emitting specific wavelengths, such as an array of two or more LEDs, such as an array of three or more LEDs, such as an array of five or more LEDs, including an array of ten or more LEDs.

In certain embodiments, the light source is a stroboscopic light source where the polymerizable composition is illuminated with periodic flashes of light. Depending on the light source (e.g., flash lamp, pulsed laser) the frequency of light strobe may vary, and may be 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater. In these embodiments, the strobe light may be operably coupled to a processor having a frequency generator which regulates strobe frequency. In some instances, the frequency generator of the strobe light is operably coupled to the projection monitoring component of the micro-digital light projection system such that the frequency of the strobe light is synchronized with the frequency of image capture on the build surface of the light interface polymerization module. In certain instances, suitable strobe light sources and frequency controllers include, but are not limited to those described in U.S. Pat. Nos. 5,700,692 and 6,372,506, the disclosures of which are herein incorporated by reference.

In some embodiments, the light beam generator includes one or more lasers. Lasers of interest may include pulsed lasers or continuous wave lasers. The type and number of lasers used in the subject methods may vary and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the light beam generator includes a dye laser, such as a stilbene, coumarin or rhodamine laser. In yet other instances, the light beam generator includes a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the light beam generator includes a solid-state laser, such as a ruby laser, an Nd: YAG laser, NdCrYAG laser, Er: YAG laser, Nd: YLF laser, Nd: $YVO_4$ laser, Nd: $YCa_4O(BO_3)_3$ laser, Nd: YCOB laser, titanium sapphire laser, thulium YAG laser, ytterbium YAG laser, ytterbium$_2O_3$ laser or cerium doped lasers and combinations thereof. In still other instances, the light beam generator includes a semiconductor diode laser, optically pumped semiconductor laser (OPSL), or a frequency doubled- or frequency tripled implementation of any of the above mentioned lasers.

In some embodiments, the light beam generator includes one or more tube lenses that are configured with adjustable focal lengths. In some instances, the tube lens is a telecentric lens. In certain instances, the tube lens is configured for widefield imaging. In some instances, the tube lens has an adjustable focal length which ranges from 10 mm to 1000 mm, such as from 20 mm to 900 mm, such as from 30 mm to 800 mm, such as from 40 mm to 700 mm, such as from 50 mm to 600 mm, such as from 60 mm to 500 mm, such as from 70 mm to 400 mm, such as from 80 mm to 300 mm and including an adjustable focal length of from 100 mm to 200 mm.

In some embodiments, the light beam generator includes one or more projection lenses, such as 2 or more projection lenses, such as 3 or more projection lenses, such as 4 or more projection lenses and including 5 or more projection lenses. In some instances, the projection lenses provide for magnification of 2-fold or more, such as 3-fold or more, such as 4-fold or more, such as 5-fold or more, such as 6-fold or more, such as 7-fold or more, such as 8-fold or more, such as 9-fold or more and including 10-fold or more magnification. In some instances, the projection lenses provide for de-magnification having a magnification ratio ranging from 0.1 to 0.95, such as a magnification ratio of from 0.2 to 0.9, such as a magnification ratio of from 0.3 to 0.85, such as a magnification ratio of from 0.35 to 0.8, such as a magnification ratio of from 0.5 to 0.75 and including a magnification ratio of from 0.55 to 0.7, for example a magnification ratio of 0.6.

In some embodiments, the light beam generator component includes one or more beamsplitters. The beamsplitter may be any an optical component that is configured to propagate a beam of light along two or more different and spatially separated optical paths, such that a predetermined portion of the light is propagated along each optical path. The beamsplitter may be any convenient beamsplitting protocol such as with triangular prism, slivered mirror prisms, dichroic mirror prisms, among other types of beamsplitters. The beamsplitter may be formed from any suitable material so long as the beamsplitter is capable of propagating the desired amount and wavelengths of light along each optical path. For example, beamsplitters of interest may be formed from glass (e.g., N-SF10, N-SF11, N-SF57, N-BK7, N-LAK21 or N-LAF35 glass), silica (e.g., fused silica), quartz, crystal (e.g., $CaF_2$ crystal), zinc selenide (ZnSe), $F_2$, germanium (Ge) titanate (e.g., S-TIH11), borosilicate (e.g., BK7). In certain embodiments, the beamsplitter is formed from a polymeric material, such as, but not limited to, polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the beamsplitter is formed from a polyester, where polyesters of interest may include, but are not limited to, poly(alkylene terephthalates) such as poly (ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(β-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly (trans-1,4-cyclohexanediyl ethylene dicarboxylate); poly(1, 4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as(S)-polylactide, (R,S)-polylactide, poly (tetramethylglycolide), and poly(lactide-co-glycolide); and polycarbonates of bisphenol A, 3,3'-dimethylbisphenol A, 3,3', 5,5'-tetrachlorobisphenol A, 3,3', 5,5'-tetramethylbisphenol A; polyamides such as poly(p-phenylene terephthalamide); polyethylene Terephthalate (e.g., Mylar™ Polyethylene Terephthalate), combinations thereof, and the like.

In embodiments, the micro-digital light projection system includes a light projection monitoring component having a photodetector. Photodetectors may be any convenient light detecting protocol, including but not limited to photosensors or photodetectors, such as active-pixel sensors (APSs), avalanche photodiodes (APDs), quadrant photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the photodetector is a photomultiplier tube, such as a photomultiplier tube having an active detecting surface area of each region that ranges from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

In certain embodiments, the light projection monitoring component includes one or more photodetectors that are optically coupled to a slit. Depending on the size of the active detecting surface of the photodetector, slits according to certain instances have a rectangular (or other polygonal shape) opening having a width of from 0.01 mm to 2 mm, such as from 0.1 mm to 1.9 mm, such as from 0.2 mm to 1.8 mm, such as from 0.3 mm to 1.7 mm, such as from 0.4 mm to 1.6 mm, and including a width of from 0.5 mm to 1.5 mm and a length of from 0.01 mm to 2 mm, such as from 0.1 mm to 1.9 mm, such as from 0.2 mm to 1.8 mm, such as from 0.3 mm to 1.7 mm, such as from 0.4 mm to 1.6 mm, and including a length of from 0.5 mm to 1.5 mm. In certain instances, the width of the slit is 1 mm or less, such as 0.9 mm or less, such as 0.8 mm or less, such as 0.7 mm or less, such as 0.6 mm or less, such as 0.5 mm or less and including a width that is 0.4 mm or less. In certain instances, the light detection system includes a photodetector that is optically coupled to a slit having a plurality of openings, such as a slit having 2 or more openings, such as 3 or more openings, such as 4 or more openings, such as 5 or more openings, such as 6 or more openings, such as 7 or more openings, such as 8 or more openings, such as 9 or more openings and including a slit having 10 or more openings.

Light may be measured by the photodetector at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light at 400 or more different wavelengths. Light may be measured continuously or in discrete intervals. In some instances, detectors of interest are configured to take measurements of the light continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

In certain embodiments, the micro-digital light projection system is a digital light processing (DLP) system having a digital micromirror device such as that described in U.S. Patent Publication Nos. 2017/0095972; 2022/0250313; 2022/0048242 and U.S. Pat. Nos. 11,358,342; 11,141,910, the disclosures of which are herein incorporated by reference.

In some embodiments, systems also include a processor having memory operably coupled to the processor where the memory includes instructions stored thereon, which when executed by the processor, cause the processor to irradiate a polymerizable composition positioned between a build elevator and a build surface to generate a polymerizable composition having a first polymerized region of the polymerizable composition in contact with the build elevator and a first non-polymerized region of the polymerizable composition in contact with the build surface; displace the build elevator away from the build surface; irradiate the first non-polymerized region of the polymerizable composition to generate a second polymerized region of the polymerizable composition in contact with the first polymerized region and a second non-polymerized region in contact with the build surface. These steps are repeated in a manner sufficient to generate the polymeric microneedle having a lattice microstructure. For example, the steps may be repeated 2 or more times, such as 3 or more times, such as 4 or more times, such as 5 or more times, such as 10 or more times, such as 20 or more times, such as 30 or more times, such as 40 or more times, such as 50 or more times, such as 100 or more times, such as 250 or more times, such as 500 or more times and including 1000 or more times.

In some embodiments, the memory includes instructions to irradiate the polymerizable composition for a duration sufficient to bond the first polymerized region of the polymerizable composition to the build elevator. In some instances, the memory includes instructions to irradiate the polymerizable composition for 1 second or longer to bond the first polymerized region of the polymerizable composition to the build elevator, such as from 5 seconds longer, such as for 10 seconds or longer, such as for 20 seconds or longer, such as for 30 seconds or longer, such as for 1 minute or longer, such as for 5 minutes or longer and including for 10 minutes or longer.

In some embodiments, the memory includes instructions to displace the build elevator in predetermined increments which builds the lattice microstructure of the polymeric microneedles. In some instances, the memory includes instructions to displace the build elevator in increments of 0.001 μm or more, such as 0.005 μm or more, such as 0.01 μm or more, such as 0.05 μm or more, such as 0.1 μm or more, such as 0.5 μm or more, such as 1 μm or more, such as 2 μm or more, such as 3 μm or more, such as 4 μm or more, such as 5 μm or more and including in increments of 10 μm or more. In certain instances, the memory includes instructions to displace the build elevator in increments of from 0.001 μm to 20 μm, such as from 0.005 μm to 19 μm, such as from 0.01 μm to 18 μm, such as from 0.05 μm to 17 μm, such as from 0.1 μm to 16 μm, such as from 0.2 μm to 17 μm, such as from 0.3 μm to 16 μm, such as from 0.4 μm to 15 μm, such as from 0.5 μm to 14 μm, such as from 0.6 μm to 13 μm, such as from 0.7 μm to 12 μm, such as from 0.8 μm to 11 μm and including from 0.9 μm to 10 μm.

In some embodiments, systems also include a source of the polymerizable composition. In some instances, the source is configured to continuously deliver polymerizable composition to the build surface. In some instances, the system is configured to add polymerizable composition to the build surface after each displacement of the build elevator away from the build surface. In some embodiments, the polymerizable composition is selected from polycaprolactone, polyalycolic acid, polylactic acid, polylactic-co-glycolic acid, polyethylene glycol, thiol-enes, anhydrides, polyacrylic acid, poly methylmethacrylate, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof. In certain embodiments, polymeric microneedles are formed from polyethylene glycol dimethacrylate (PEGDMA).

In some embodiments, the light source is configured to irradiate through the build surface. In some instances, at least a part of the build surface is permeable to a polymerization inhibitor, such as where the polymerization inhibitor is oxygen.

In certain embodiments, the liquid interface polymerization module is a continuous liquid interface production (CLIP) system such as that described in International Patent Publication No. WO 2014/126837; U.S. Patent Publication Nos. 2018/0064920; 2017/0095972; 2021/0246252 and U.S. Patent Publication Nos. 10,155,882; 10,792,857, the disclosures of which are herein incorporated by reference.

In certain embodiments, the memory includes instructions for determining a focal plane on the build surface with the micro-digital light projection system. In some instances, the memory includes instructions to determine the focal plane by irradiating the build surface with a stroboscopic light source through the tube lens and displacing the build surface until the light is focused on the build surface through the tube lens. In certain embodiments, the memory includes instructions for determining the focal plane on the build surface by irradiating build surface with the stroboscopic light source with periodic flashes of light. For example, the frequency of each light pulse may be 0.0001 kHz or greater, such as 0.0005 kHz or greater, such as 0.001 kHz or greater, such as 0.005 kHz or greater, such as 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater. In certain instances, the frequency of pulsed irradiation by the light source ranges from 0.00001 KHz to 1000 kHz, such as from 0.00005 kHz to 900 kHz, such as from 0.0001 kHz to 800 kHz, such as from 0.0005 kHz to 700 kHz, such as from 0.001 kHz to 600 kHz, such as from 0.005 kHz to 500 kHz, such as from 0.01 kHz to 400 kHz, such as from 0.05 kHz to 300 kHz, such as from 0.1 kHz to 200 kHz and including from 1 kHz to 100 KHz. The duration of light irradiation for each light pulse (i.e., pulse width) may vary and may be 0.000001 ms or more, such as 0.000005 ms or more, such as 0.00001 ms or more, such as 0.00005 ms or more, such as 0.0001 ms or more, such as 0.0005 ms or more, such as 0.001 ms or more, such as 0.005 ms or more, such as 0.01 ms or more, such as 0.05 ms or more, such as 0.1 ms or more, such as 0.5 ms or more, such as 1 ms or more, such as 2 ms or more, such as 3 ms or more, such as 4 ms or more, such as 5 ms or more, such as 10 ms or more, such as 25 ms or more, such as 50 ms or more, such as 100 ms or more and including 500 ms or more. For example, the duration of light irradiation may range from 0.000001 ms to 1000 ms, such as from 0.000005 ms to 950 ms, such as from 0.00001 ms to 900 ms, such as from 0.00005 ms to 850 ms, such as from 0.0001 ms to 800 ms, such as from 0.0005 ms to 750 ms, such as from 0.001 ms to 700 ms, such as from 0.005 ms to 650 ms, such as from 0.01 ms to 600 ms, such as from 0.05 ms to 550 ms, such as from 0.1 ms to 500 ms, such as from 0.5 ms to 450 ms, such as from 1 ms to 400 ms, such as from 5 ms to 350 ms and including from 10 ms to 300 ms. In some instances, the memory includes instructions to irradiate the build surface with a plane of light having a projected image pattern with the stroboscopic light source.

In some instances, determining the focal plane on the build surface includes adjusting the focus of the tube lens. In some instances, the focal point of the tube lens is increased to adjust the focus onto the build surface. For example, the focal point may be increased by 1 μm or more, such as by 5 μm or more, such as by 10 μm or more, such as by 50 μm or more, such as by 100 μm or more, such as by 500 μm or more, such as by 1 mm or more, such as by 5 mm or more, such as by 10 mm or more, such as by 50 mm or more and including by 100 mm or more. In some instances, the focal point of the tube lens is decreased to adjust the focus onto the build surface. For example, the focal point may be decreased by 1 μm or more, such as by 5 μm or more, such as by 10 μm or more, such as by 50 μm or more, such as by 100 μm or more, such as by 500 μm or more, such as by 1 mm or more, such as by 5 mm or more, such as by 10 mm or more, such as by 50 mm or more and including by 100 mm or more.

In some embodiments, the memory includes instructions to displace the build surface until the projected image pattern is in focus with the build surface. The build surface and build elevator may be displaced using any convenient displacement protocol, such as manually (i.e., movement of the build surface or build elevator directly by hand), with assistance by a mechanical device or by a motor actuated displacement device. For example, in some embodiments the build surface or build elevator is moved in the subject systems with a mechanically actuated translation stage, mechanical leadscrew assembly, mechanical slide device, mechanical lateral motion device, mechanically operated geared translation device. In other embodiments, the build surface or build elevator is moved with a motor actuated translation stage, leadscrew translation assembly, geared translation device, such as those employing a stepper motor, servo motor, brushless electric motor, brushed DC motor, micro-step drive motor, high resolution stepper motor, among other types of motors. In some instances, the build surface is displaced by 1 μm or more, such as by 5 μm or more, such as by 10 μm or more, such as by 50 μm or more, such as by 100 μm or more and including by 500 μm or more. In certain embodiments, the build surface is displaced by 400 μm or less, such as 350 μm or less, such as by 300 μm or less, such as by 250 μm or less, such as by 200 μm or less, such as by 150 μm or less, such as by 100 μm or less and including by 50 μm or less.

In some instances, the memory includes instructions to generate an image stack having a plurality of the projected image patterns. The image stack may include 2 or more projected image patterns, such as 3 or more, such as 4 or more, such as 5 or more, such as 10 or more and including 25 or more projected image patterns. In certain instances, the memory includes instructions to determine the focal plane of the build surface based on the generated image stack.

Aspects of the present disclosure further include computer-controlled systems, where the systems further include one or more computers for complete automation or partial automation of the methods described herein. In embodiments, the system includes an input module, a processing module and an output module. The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques. The processor may be any suitable analog or digital system.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid-state storage devices (including magnetic or optical disks or tape or RAM, or any other suitable device, either fixed or portable). The processor may include a general-purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Methods for Making a Polymeric Microneedle

Aspects of the disclosure also include methods for making a polymeric microneedle having a lattice microstructure with one or more lattice cell units. Methods according to certain embodiments is a high resolution continuous additive processing method that includes irradiating a polymerizable composition positioned between a build elevator and a build surface to generate a polymerizable composition having a first polymerized region of the polymerizable composition in contact with the build elevator and a first non-polymerized region of the polymerizable composition in contact with the build surface; displacing the build elevator away from the build surface; irradiating the first non-polymerized region of the polymerizable composition to generate a second polymerized region of the polymerizable composition in contact with the first polymerized region and a second non-polymerized region in contact with the build surface and repeating in a manner sufficient to generate a microneedle having a lattice microstructure. These steps are repeated in a manner sufficient to generate a polymeric microneedle having a lattice microstructure. For example, the steps may be repeated 2 or more times, such as 3 or more times, such as 4 or more times, such as 5 or more times, such as 10 or more times, such as 20 or more times, such as 30 or more times, such as 40 or more times, such as 50 or more times, such as 100 or more times, such as 250 or more times, such as 500 or more times and including 1000 or more times.

In some embodiments, the polymerizable composition is irradiated with a light beam generator component of a micro-digital light projection system. In some instances, the light source is a broadband light source that emits light having wavelengths from 400 nm to 1000 nm. In some instances, the broadband light source is a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, a multi-LED integrated white light source, among other broadband light sources or any combination thereof. In some instances, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light. In some instances, the polymerizable composition is irradiated with a narrow band light source such as a narrow wavelength LED, laser diode or a broadband light source coupled to one or more optical bandpass filters, diffraction gratings, monochromators or any combination thereof.

In certain embodiments, the light source is a stroboscopic light source and the polymerizable composition is illuminated with periodic flashes of light, such as where the polymerizable composition is irradiated at a frequency of 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater. In certain instances, the polymerizable composition is irradiated with a laser, such as pulsed laser or a continuous wave laser.

In some embodiments, the polymerizable composition is in contact with the build elevator and the build surface. In some instances, methods include irradiating the polymerizable composition for 1 second or longer to bond the first polymerized region of the polymerizable composition to the build elevator, such as from 5 seconds longer, such as for 10 seconds or longer, such as for 20 seconds or longer, such as for 30 seconds or longer, such as for 1 minute or longer, such as for 5 minutes or longer and including for 10 minutes or longer.

In some embodiments, the build elevator is displaced away from the build surface after the first polymerized region of the polymerizable composition is bonded to the build elevator. In some instances, the build elevator is displaced in increments of 0.001 μm or more, such as 0.005 μm or more, such as 0.01 μm or more, such as 0.05 μm or more, such as 0.1 μm or more, such as 0.5 μm or more, such as 1 μm or more, such as 2 μm or more, such as 3 μm or more, such as 4 μm or more, such as 5 μm or more and including in increments of 10 μm or more. In certain instances, the build elevator is displaced in increments of from 0.001 μm to 20 μm, such as from 0.005 μm to 19 μm, such as from 0.01 μm to 18 μm, such as from 0.05 μm to 17 μm, such as from 0.1 μm to 16 μm, such as from 0.2 μm to 17 μm, such as from 0.3 μm to 16 μm, such as from 0.4 μm to 15 μm, such as from 0.5 μm to 14 μm, such as from 0.6 μm to 13 μm, such as from 0.7 μm to 12 μm, such as from 0.8 μm to 11 μm and including from 0.9 μm to 10 μm.

In certain instances, polymerizable composition is added to the build surface after each displacement of the build elevator away from the build surface. In some instances, the polymerizable composition is continuously added to the build surface. In other instances, the polymerizable composition is added to the build surface in discreet intervals each having a predetermined amount. In some embodiments, the polymerizable composition is selected from polycaprolactone, polyalycolic acid, polylactic acid, polylactic-co-glycolic acid, polyethylene glycol, thiol-enes, anhydrides, polyacrylic acid, poly methylmethacrylate, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof. In certain embodiments, polymeric microneedles are formed from polyethylene glycol dimethacrylate (PEGDMA).

In some embodiments, the polymerizable composition is irradiated through build surface. In some instances, the polymerizable composition is irradiated in the presence of a polymerization inhibitor. In certain embodiments, the polymerizable composition is continuously polymerized while displacing the build elevator away from the build surface. In certain cases, the polymerization inhibitor is oxygen and the build surface is permeable to oxygen. In certain instances, polymerizing the polymerizable composition in the presence of a polymerization inhibitor such as oxygen enables continuous (i.e., not layer-by-layer) generation the lattice microstructure with a liquid "dead zone" at the interface between the build surface and the building polymeric microneedle. In some instances, the dead zone is generated because oxygen acts as a polymerization inhibitor, passing through the oxygen-permeable build surface. Photopolymerization cannot occur in the oxygen containing "dead zone" region such that this region remains fluid, and the polymerized component in contact with the build surface so that the building lattice microstructure does not physically attach to the build surface. Displacement of the build elevator therefore generates a continuous polymeric lattice microstructure which exhibits sufficient mechanical integrity and surface isotropicity for use as a polymeric microneedle.

In certain embodiments, the polymerizable composition is polymerized using a liquid interface polymerization module that is a continuous liquid interface production (CLIP) system such as that described in International Patent Publication No. WO 2014/126837; U.S. Patent Publication Nos. 2018/0064920; 2017/0095972; 2021/0246252 and U.S. Patent Publication Nos. 10,155,882; 10,792,857, the disclosures of which are herein incorporated by reference.

In some embodiments, methods include irradiating the polymerizable composition with a micro-digital light projection system as described in detail above. In some instances, methods include determining a focal plane on the build surface using the micro-digital light projection system. In some embodiments, determining the focal plane on the build surface includes irradiating the build surface with a stroboscopic light source through the tube lens and displacing the build surface until the light is focused on the build surface through the tube lens. In certain embodiments, methods for determining the focal plane on the build surface includes irradiating build surface with the stroboscopic light source with periodic flashes of light. For example, the frequency of each light pulse may be 0.0001 kHz or greater, such as 0.0005 kHz or greater, such as 0.001 kHz or greater, such as 0.005 kHz or greater, such as 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 KHz or greater, such as 25 kHz or greater, such as 50 kHz or greater and including 100 KHz or greater. In certain instances, the frequency of pulsed irradiation by the light source ranges from 0.00001 kHz to 1000 kHz, such as from 0.00005 kHz to 900 kHz, such as from 0.0001 kHz to 800 kHz, such as from 0.0005 kHz to 700 kHz, such as from 0.001 kHz to 600 kHz, such as from 0.005 kHz to 500 kHz, such as from 0.01 kHz to 400 kHz, such as from 0.05 KHz to 300 kHz, such as from 0.1 KHz to 200 kHz and including from 1 kHz to 100 kHz. The duration of light irradiation for each light pulse (i.e., pulse width) may vary and may be 0.000001 ms or more, such as 0.000005 ms or more, such as 0.00001 ms or more, such as 0.00005 ms or more, such as 0.0001 ms or more, such as 0.0005 ms or more, such as 0.001 ms or more, such as 0.005 ms or more, such as 0.01 ms or more, such as 0.05 ms or more, such as 0.1 ms or more, such as 0.5 ms or more, such as 1 ms or more, such as 2 ms or more, such as 3 ms or more, such as 4 ms or more, such as 5 ms or more, such as 10 ms or more, such as 25 ms or more, such as 50 ms or more, such as 100 ms or more and including 500 ms or more. For example, the duration of light irradiation may range from 0.000001 ms to 1000 ms, such as from 0.000005 ms to 950 ms, such as from 0.00001 ms to 900 ms, such as from 0.00005 ms to 850 ms, such as from 0.0001 ms to 800 ms, such as from 0.0005 ms to 750 ms, such as from 0.001 ms to 700 ms, such as from 0.005 ms to 650 ms, such as from 0.01 ms to 600 ms, such as from 0.05 ms to 550 ms, such as from 0.1 ms to 500 ms, such as from 0.5 ms to 450 ms, such as from 1 ms to 400 ms, such as from 5 ms to 350 ms and including from 10 ms to 300 ms. In some instances, methods include irradiating the build surface with a plane of light having a projected image pattern with the stroboscopic light source.

In some instances, determining the focal plane on the build surface includes adjusting the focus of the tube lens. In some instances, the focal point of the tube lens is increased to adjust the focus onto the build surface. For example, the focal point may be increased by 1 μm or more, such as by 5 μm or more, such as by 10 μm or more, such as by 50 μm or more, such as by 100 μm or more, such as by 500 μm or more, such as by 1 mm or more, such as by 5 mm or more, such as by 10 mm or more, such as by 50 mm or more and including by 100 mm or more. In some instances, the focal point of the tube lens is decreased to adjust the focus onto the build surface. For example, the focal point may be decreased by 1 μm or more, such as by 5 μm or more, such as by 10 μm or more, such as by 50 μm or more, such as by 100 μm or more, such as by 500 μm or more, such as by 1 mm or more, such as by 5 mm or more, such as by 10 mm or more, such as by 50 mm or more and including by 100 mm or more.

In some embodiments, methods include displacing the build surface until the projected image pattern is in focus with the build surface. The build surface and build elevator may be displaced using any convenient displacement protocol, such as manually (i.e., movement of the build surface or build elevator directly by hand), with assistance by a mechanical device or by a motor actuated displacement device. For example, in some embodiments the build surface or build elevator is moved with a mechanically actuated translation stage, mechanical leadscrew assembly, mechanical slide device, mechanical lateral motion device, mechanically operated geared translation device. In other embodiments, the build surface or build elevator is moved with a motor actuated translation stage, leadscrew translation assembly, geared translation device, such as those employing a stepper motor, servo motor, brushless electric motor, brushed DC motor, micro-step drive motor, high resolution stepper motor, among other types of motors. In some instances, the build surface is displaced by 1 μm or more, such as by 5 μm or more, such as by 10 μm or more, such as by 50 μm or more, such as by 100 μm or more and including by 500 μm or more. In certain embodiments, the build surface is displaced by 400 μm or less, such as 350 μm or less, such as by 300 μm or less, such as by 250 μm or less, such as by 200 μm or less, such as by 150 μm or less, such as by 100 μm or less and including by 50 μm or less.

In some instances, methods include generating an image stack having a plurality of the projected image patterns. The image stack may include 2 or more projected image patterns, such as 3 or more, such as 4 or more, such as 5 or more, such as 10 or more and including 25 or more projected image patterns. In certain instances, methods include determining the focal plane of the build surface based on the generated image stack. In embodiments, methods as described here for generating polymeric microstructures (e.g., polymeric microneedles) having a lattice microstructure provide for a resolution of 10 μm or less, such as 5 μm or less. In certain embodiments, the subject methods provide for a resolution of from 1.0 μm to 4 μm, such as from 1.5 μm to 3.8 μm.

As described above, in some instances polymeric microneedles include an active agent compound. Methods according to certain embodiments include preparing a polymeric microneedle having an active agent compound. Methods in some instances include coating the active agent compound onto a surface of the polymeric microneedle. In some instances, the active agent compound is coated onto a surface of the polymeric microneedle as a fluidic composition. In these embodiments, the fluidic composition may be applied to the surface of the polymeric microneedle by for example, dip-coating or spray coating the active agent composition. In some embodiments, methods include coating a surface of the polymeric microneedle with a solid active agent compound such as by dry-casting a powder containing the active agent compound.

In some instances, methods include coating 5% or more of the surface of the polymeric microneedle with the active agent compound, such as 10% or more, such as 15% or more, such as 20% or more, such as 25% or more, such as 50% or more, such as 75% or more, such as 90% or more and including coating 95% or more of the surface of the polymeric microneedle. In certain instances, the entire surface of the polymeric microneedle is coated with the active agent compound. In some instances, methods include coating the active agent compound onto a tip section of the polymeric microneedle. In some instances, methods include coating the active agent onto a surface of the body section of the polymeric microneedle. In some instances, methods include coating the active agent onto a surface of a base section of the polymeric microneedle. In certain instances, the lattice microstructure component of the polymeric microneedle is coated with the active agent compound.

Depending on the dosage amount of the active agent compound desired, the amount of active agent compound coated onto the surface may vary, such as coating 0.001 μg or more onto a surface of the polymeric microneedle, such as 0.005 μg or more, such as 0.01 μg or more, such as 0.05 μg or more, such as 0.1 μg or more, such as 0.5 μg or more, such as 1 μg or more, such as 5 μg or more, such as 25 μg or more, such as 50 μg or more, such as 100 μg or more and including coating 500 μg or more of the active agent compound onto the surface of the polymeric microneedle.

In some embodiments, the active agent compound is incorporated into an interior space of the lattice microstructure of the polymeric microneedle. In some instances, methods include microfluidic injection filling of the active agent compound into the lattice microstructure of the polymeric microneedles. In other instances, methods include contacting the lattice microstructure with a composition containing the active agent compound and incorporating the active agent by capillary action. In some embodiments, the polymeric microneedles are dipped into a composition containing the active agent compound and an amount of the active agent is incorporated into the void space of the lattice microstructure by capillary action. Depending on the density of the lattice cell units in the lattice microstructure, the polymeric microneedle may be contacted with (submerged within) the active agent composition for 0.01 minutes or more, such as for 0.05 minutes or more, such as for 0.1 minutes or more, such as for 0.5 minutes or more, such as from 1 minute or more, such as for 5 minutes or more, such as for 10 minutes or more, such as for 30 minutes or more, such as for 60 minutes or more and including for 6 hours or more to take up the active agent composition into the lattice microstructure.

In some embodiments, methods include preparing polymeric microneedles where the lattice microstructure contains regions of increased concentration of the active agent compound, such as where the concentration of active agent compound in these regions increases by 1% or more across the longitudinal axis of the lattice microstructure, such as by 2% or more, such as by 3% or more, such as by 4% or more, such as by 5% or more, such as by 10% or more, such as by 20% or more, such as by 30% or more, such as by 40% or more and including by 50% or more. In some instances, the regions of increased concentrations of active agent are present at various increments across the longitudinal axis of the lattice microstructure. For example, the regions of increased active agent concentration may be present at increments of every 10 μm or more across the longitudinal axis of the lattice microstructure, such as every 20 μm or more, such as every 30 μm or more, such as every 40 μm or more and including every 50 μm or more.

In some embodiments, methods for preparing a polymeric microneedle containing an active agent compound include incorporating the active agent compound into the polymerizable composition, such that when the polymeric microneedle is formed from the polymerizable composition (e.g., by high resolution digital light projection-continuous liquid interface processing as described above) the active agent compound is present within the void space of the lattice microstructure. For example, the active agent composition may be present in the polymerizable composition at a concentration of 0.005 μg/μL or more, such as 0.01 μg/μL or more, such as 0.05 μg/μL or more, such as 0.1 μg/μL or more, such as 0.5 μg/μL or more, such as 1 μg/μL or more, such as 5 μg/μL or more, such as 25 μg/μL or more, such as 50 μg/μL or more, such as 100 μg/μL or more and including coating 500 μg/μL or more. In some instances, where the lattice microstructure has regions of increased concentration of active agent compound, methods include increasing the amount of active agent composition present in the source of the polymerizable composition while preparing the polymeric microneedle, such as by increasing the amount of active agent in the polymerizable composition by 1% or more, such as by 2% or more, such as by 5% or more, such as by 10% or more, such as by 25% or more, such as by 50% or more and including by 75% or more.

Kits

Kits for use in practicing certain methods described herein are also provided. In certain embodiments, the kits include one or more patches containing a plurality of polymeric microneedles having a lattice microstructure as described above. In certain embodiments, the kits include an adhesive overlay. In a given kit that includes two or more of the subject patches, the patches may be individually packaged or present within a common container.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. Yet another form of these instructions is a computer readable medium, e.g., diskette, compact disk (CD), portable flash drive, USB storage, DVD, Blu-ray disk, etc.), and the like, on which the information has been recorded. Yet another form of these instructions that may be present is a website address which may be used via the internet to access the information at a removed site.

Notwithstanding the appended claims, the disclosure is also defined by the following clauses:

1. A polymeric microneedle comprising a lattice microstructure having one or more lattice cell units.
2. The microneedle according to 1, wherein the microneedle comprises 2 or more repeating lattice cell units.
3. The microneedle according to 2, wherein the microneedle comprises 5 or more repeating lattice cell units.
4. The microneedle according to any one of 1-3, wherein the microneedle comprises a gradient in the lattice cell units such that the density of lattice cell units increases across a longitudinal axis of the microneedle.
5. The microneedle according to any one of 1-4, wherein the lattice cell unit comprises a lattice shape selected from the group consisting of tetrahedral, Kagome, rhombic, icosahedral, Voronoi and triangular.
6. The microneedle according to any one of 1-5, wherein the microneedle comprises lattice cell units having a size of from 100 μm to 1000 μm.
7. The microneedle according to 6, wherein the microneedle comprises lattice cell units having a size of from 200 μm to 500 μm.
8. The microneedle according to any one of 1-7, wherein the lattice microstructure comprises a plurality of struts.
9. The microneedle according to 8, wherein the lattice microstructure comprises struts having a thickness of from 25 μm to 150 μm.
10. The microneedle according to 8, wherein the lattice microstructure comprises struts having a thickness of from 50 μm to 100 μm.
11. The microneedle according to 8, wherein the lattice microstructure comprises struts having a thickness of from 70 μm to 90 μm.
12. The microneedle according to any one of 1-11, wherein the microneedle comprises a square pyramidal or conical projection shape.
13. The microneedle according to any one of 1-11, wherein the microneedle comprises an obelisk projection shape.
14. The microneedle according to any one of 1-13, wherein the microneedle has a length of from 500 μm to 2000 μm.
15. The microneedle according to 14, wherein the microneedle has a length of from 700 μm to 1200 μm.
16. The microneedle according to any one of 1-15, wherein the microneedle has a base width of from 100 μm to 700 μm.

17. The microneedle according to 16, wherein the microneedle has a base with of from 200 μm to 400 μm.
18. The microneedle according to any one of 1-17, wherein lattice microstructure has a volume of from 0.01 μL to 2 μL.
19. The microneedle according to 18, wherein the lattice microstructure has a volume of 0.1 μL.
20. The microneedle according to any one of 1-19, wherein the microneedle comprises:
 a tip section comprising a solid structure;
 a body section comprising a lattice structure; and
 a base section comprising a solid structure.
21. The microneedle according to 20, wherein the tip section comprises a length of from 25 μm to 500 μm.
22. The microneedle according to any one of 20-21, wherein the tip section comprises a base width of 50 μm to 300 μm.
23. The microneedle according to any one of 20-21, wherein the microneedle has a tip diameter of from 0.1 μm to 10 μm.
24. The microneedle according to any one of 20-23, wherein the body section comprises a length of from 50 μm to 1000 μm.
25. The microneedle according to any one of 20-23, wherein the body section comprises a width of 50 μm to 300 μm.
26. The microneedle according to any one of 20-25, wherein the base section comprises a length of from 25 μm to 500 μm.
27. The microneedle according to any one of 20-25, wherein the base section comprises a base width of 50 μm to 300 μm.
28. The microneedle according to any one of 1-27, wherein the lattice structure is formed from a polymerizable material selected from the group consisting of polycaprolactone, polyalycolic acid, polylactic acid, polylactic-co-glycolic acid, polyethylene glycol, thiolenes, anhydrides, polyacrylic acid, poly methylmethacrylate, trimethylolpropane triacrylate (TMPTA) monomer, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof.
29. The microneedle according to any one of 1-28, wherein the lattice structure is formed from polyethylene glycol dimethacrylate (PEGDMA).
30. The microneedle according to any one of 1-29, wherein the microneedle is formed from a biodegradable polymerizable material.
31. The microneedle according to any one of 1-30, wherein the microneedle is dissolvable in an aqueous medium.
32. A patch comprising:
 a backing layer; and
 a plurality of polymeric microneedles in contact with the backing layer, wherein each microneedle comprises a lattice microstructure having one or more lattice cell units.
33. The patch according to 32, wherein the plurality of microneedles form an array of microneedles on the backing layer.
34. The patch according to any one of 32-33, wherein the microneedles are separated from each other on the backing layer by an average distance of from 5 μm to 1000 μm.
35. The patch according to 34, wherein the microneedles are separated from each other on the backing layer by an average distance of from 100 μm to 500 μm.
36. The patch according to any one of 32-35, wherein the microneedles further comprise an active agent compound.
37. The patch according to 36, wherein the active agent comprises a small molecule active agent compound.
38. The patch according to 36, wherein the active agent comprises an immunogenic active agent compound.
39. The patch according to 38, wherein the active agent compound comprises a vaccine.
40. The patch according to any one of 32-39, wherein the backing layer further comprises a pressure sensitive adhesive.
41. The patch according to any one of 32-40, wherein each microneedle comprises 2 or more repeating lattice cell units.
42. The patch according to any one of 32-40, wherein each microneedle comprises 5 or more repeating lattice cell units.
43. The patch according to any one of 32-42, wherein one or more microneedles comprises a gradient in the lattice cell units such that the density of lattice cell units increases across a longitudinal axis of the microneedle.
44. The patch according to any one of 32-43, wherein the lattice cell unit comprises a lattice shape selected from the group consisting of tetrahedral, Kagome, rhombic, icosahedral, Voronoi and triangular.
45. The patch according to any one of 32-44, wherein each microneedle comprises lattice cell units having a size of from 100 μm to 1000 μm.
46. The patch according to 45, wherein each microneedle comprises lattice cell units having a size of from 200 μm to 500 μm.
47. The patch according to any one of 32-46, wherein the lattice microstructure comprises a plurality of struts.
48. The patch according to 47, wherein the lattice microstructure comprises struts having a thickness of from 25 μm to 150 μm.
49. The patch according to 47, wherein the lattice microstructure comprises struts having a thickness of from 50 μm to 100 μm.
50. The patch according to 47, wherein the lattice microstructure comprises struts having a thickness of from 70 μm to 90 μm.
51. The patch according to any one of 32-50, wherein each microneedle comprises a square pyramidal or conical projection shape.
52. The patch according to any one of 32-50, wherein each microneedle comprises an obelisk projection shape.
53. The patch according to any one of 32-52, wherein each microneedle has a length of from 500 μm to 2000 μm.
54. The patch according to 53, wherein each microneedle has a length of from 700 μm to 1200 μm.
55. The patch according to any one of 32-54, wherein each microneedle has a base width of from 100 μm to 700 μm.
56. The patch according to 55, wherein each microneedle has a base with of from 200 μm to 400 μm.
57. The patch according to any one of 32-56, wherein lattice structure has a volume of from 0.01 μL to 2 μL.
58. The patch according to 57, wherein the lattice microstructure has a volume of 0.1 μL.

59. The patch according to any one of 32-58, wherein each microneedle comprises:
a tip section comprising a solid structure;
a body section comprising a lattice structure; and
a base section comprising a solid structure.
60. The patch according to 59, wherein the tip section comprises a length of from 25 μm to 500 μm.
61. The patch according to any one of 59-60, wherein the tip section comprises a base width of 50 μm to 300 μm.
62. The patch according to any one of 59-61, wherein the microneedle has a tip diameter of from 0.1 μm to 10 μm.
63. The patch according to any one of 59-62, wherein the body section comprises a length of from 50 μm to 1000 μm.
64. The patch according to any one of 59-62, wherein the body section comprises a width of 50 μm to 300 μm.
65. The patch according to any one of 59-64, wherein the base section comprises a length of from 25 μm to 500 μm.
66. The patch according to any one of 59-65, wherein the base section comprises a base width of 50 μm to 300 μm.
67. The patch according to any one of 32-66, wherein the each microneedle is formed from a polymerizable material selected from the group consisting of polycaprolactone, polyalycolic acid, polylactic acid, polylactic-co-glycolic acid, polyethylene glycol, thiol-enes, anhydrides, polyacrylic acid, poly methylmethacrylate, trimethylolpropane triacrylate (TMPTA) monomer, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof.
68. The patch according to any one of 32-67, wherein the lattice microstructure of one or more microneedles is formed from polyethylene glycol dimethacrylate (PEGDMA).
69. The patch according to any one of 32-68, wherein one or more microneedles is formed from a biodegradable polymerizable material.
70. The patch according to any one of 32-69, wherein one or more microneedles is dissolvable in an aqueous medium.
71. A method of making a polymeric microneedle comprising a lattice microstructure having one or more lattice cell units, the method comprising:
a) irradiating a polymerizable composition positioned between a build elevator and a build surface to generate a polymerizable composition comprising a first polymerized region of the polymerizable composition in contact with the build elevator and a first non-polymerized region of the polymerizable composition in contact with the build surface;
b) displacing the build elevator away from the build surface;
c) irradiating the first non-polymerized region of the polymerizable composition to generate a second polymerized region of the polymerizable composition in contact with the first polymerized region and a second non-polymerized region in contact with the build surface; and
d) repeating steps a)-c) in a manner sufficient to generate a microneedle comprising a lattice microstructure.
72. The method according to 71, wherein the polymerizable composition is in contact with the build elevator and the build surface.
73. The method according to 72, wherein the method comprises irradiating the polymerizable composition for a duration sufficient to bond the first polymerized region of the polymerizable composition to the build elevator.
74. The method according to any one of 71-73, wherein the build elevator is displaced in predetermined increments of from 0.5 μm to 1.0 μm.
75. The method according to 74, wherein the method further comprises adding polymerizable composition to the build surface after each displacement of the build elevator away from the build surface.
76. The method according to any one of 71-75, wherein the polymerizable composition is irradiated through build surface.
77. The method according to any one of 71-76, wherein the polymerizable composition is irradiated in the presence of a polymerization inhibitor.
78. The method according to any one of 71-77, wherein the polymerizable composition is continuously polymerized while displacing the build elevator away from the build surface.
79. The method according to any one of 77-78, wherein the build surface is permeable to the polymerization inhibitor.
80. The method according to 76, wherein the polymerization inhibitor is oxygen.
81. The method according to any one of 71-80, wherein the polymerizable composition is irradiated with light.
82. The method according to 81, wherein the polymerizable composition is irradiated with a micro-digital light projection system.
83. The method according to 82, wherein the micro-digital light projection system comprises:
a light beam generator component; and
a light projection monitoring component.
84. The method according to 83, wherein the light beam generator component comprises:
a light source;
a tube lens; and
one or more projection lenses.
85. The method according to 84, wherein the light beam generator component comprises two projection lenses.
86. The method according to 85, wherein the projection lenses are magnification lenses.
87. The method according to 86, wherein the projection lenses provide for 2-fold to 10-fold magnification.
88. The method according to any one of 84-87, wherein the light projection monitoring component comprises a photodetector.
89. The method according to 88, wherein the photodetector comprises a charge-coupled device (CCD).
90. The method according to any one of 82-89, wherein the method comprises determining a focal plane on the build surface from the micro-digital light projection system.
91. The method according to 90, wherein determining the focal plane on the build surface from the micro-digital light projection system comprises:
irradiating the build surface with a stroboscopic light source through the tube lens;
displacing the build surface until the light is focused on the build surface through the tube lens.

92. The method according to 91, wherein the build surface is irradiated with a plane of light having a projected image pattern with the stroboscopic light source.
93. The method according to any one of 91-92, wherein the build surface is displaced until the projected image pattern is in focus with the build surface.
94. The method according to any one of 91-93, wherein the focal plane on the build surface is determined with the photodetector.
95. The method according to any one of 91-93, wherein the method comprises generating an image stack comprising a plurality of the projected image patterns.
96. The method according to 95, wherein the focal plane of the build surface is determined from the generated image stack.
97. The method according to any one of 91-96, wherein the focal plane is determined through a displacement depth of the build surface of 400 μm or less.
98. The method according to any one of 82-97, wherein the micro-digital light projection system provides for a lattice microstructure resolution of from 1.0 μm to 4 μm.
99. The method according to 98, wherein the micro-digital light projection system provides for a lattice microstructure resolution of from 1.5 μm to 3.8 μm.
100. The method according to any one of 71-99, wherein the polymerizable composition comprises a polymerizable material selected from the group consisting of polycaprolactone, polyalycolic acid, polylactic acid, polylactic-co-glycolic acid, polyethylene glycol, thiol-enes, anhydrides, polyacrylic acid, poly methylmethacrylate, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof.
101. The method according to 100, wherein the polymerizable composition comprises polyethylene glycol dimethacrylate (PEGDMA).
102. The method according to any one of 71-101, wherein the microneedle comprises 2 or more repeating lattice cell units.
103. The method according to any one of 71-101, wherein the microneedle comprises 5 or more repeating lattice cell units.
104. The method according to any one of 71-103, wherein the microneedle comprises a gradient in the lattice cell units such that the density of lattice cell units increases across a longitudinal axis of the microneedle.
105. The method according to any one of 71-104, wherein the lattice cell unit comprises a lattice shape selected from the group consisting of tetrahedral, Kagome, rhombic, icosahedral, Voronoi and triangular.
106. The method according to any one of 71-105, wherein the microneedle comprises lattice cell units having a size of from 100 μm to 1000 μm.
107. The method according to 106, wherein the microneedle comprises lattice cell units having a size of from 200 μm to 500 μm.
108. The method according to any one of 71-107, wherein the lattice microstructure comprises a plurality of struts.
109. The method according to 108, wherein the lattice microstructure comprises struts having a thickness of from 25 μm to 150 μm.
110. The method according to 108, wherein the lattice microstructure comprises struts having a thickness of from 50 μm to 100 μm.
111. The method according to 108, wherein the lattice microstructure comprises struts having a thickness of from 70 μm to 90 μm.
112. The method according to any one of 71-111, wherein the microneedle comprises a square pyramidal or conical projection shape.
113. The method according to any one of 71-111, wherein the microneedle comprises an obelisk projection shape.
114. The method according to any one of 71-113, wherein the microneedle has a length of from 500 μm to 2000 μm.
115. The method according to 114, wherein the microneedle has a length of from 700 μm to 1200 μm.
116. The method according to any one of 71-115, wherein the microneedle has a base width of from 100 μm to 700 μm.
117. The method according to 116, wherein the microneedle has a base with of from 200 μm to 400 μm.
118. The method according to any one of 71-117, wherein lattice microstructure has a volume of from 0.01 μL to 2 μL.
119. The method according to 118, wherein the lattice microstructure has a volume of 0.1 μL.
120. The method according to any one of 71-119, wherein the microneedle comprises:

a tip section comprising a solid structure;

a body section comprising a lattice structure; and a base section comprising a solid structure.

121. The method according to 120, wherein the tip section comprises a length of from 25 μm to 500 μm.
122. The method according to any one of 120-121, wherein the tip section comprises a base width of 50 μm to 300 μm.
123. The method according to any one of 120-121, wherein the microneedle has a tip diameter of from 0.1 μm to 10 μm.
124. The method according to any one of 120-123, wherein the body section comprises a length of from 50 μm to 1000 μm.
125. The method according to any one of 120-123, wherein the body section comprises a width of 50 μm to 300 μm.
126. The method according to any one of 120-125, wherein the base section comprises a length of from 25 μm to 500 μm.
127. The method according to any one of 120-125, wherein the base section comprises a base width of 50 μm to 300 μm.
128. The method according to any one of 71-127, wherein the microneedle is dissolvable in an aqueous medium.
129. A method comprising applying to a skin surface of a subject a patch comprising:

a backing layer; and a plurality of polymeric microneedles in contact with the backing layer, wherein each microneedle comprises a lattice microstructure having one or more lattice cell units.

130. The method according to 129, wherein the microneedles comprise an active agent compound and applying the patch to the skin surface of the subject is sufficient to deliver a therapeutically effective amount of the active agent compound to the subject.
131. The method according to 130, wherein the active agent comprises a small molecule active agent compound.

132. The method according to 130, wherein the active agent comprises an immunogenic active agent compound.
133. The method according to 132, wherein the active agent compound comprises a vaccine.
134. The method according to 129, wherein the method comprises applying the patch to the skin surface of the subject in a manner sufficient to collect a biological fluid sample from the subject into the microneedles.
135. The method according to 134, wherein the biological fluid sample comprises interstitial fluid.
136. The method according to 134, wherein the biological fluid sample comprises dermal fluid.
137. The method according to any one of 134-136, wherein the method comprises collecting from 0.01 μL to 250 μL of the biological fluid from the subject.
138. The method according to any one of 134-136, wherein the method comprises collecting from 0.01 μL to 2 μL of the biological fluid from the subject with each of the plurality of microneedles.
139. The method according to any one of 129-138, wherein the method comprises maintaining the patch on the skin surface of the subject for an extended period of time.
140. The method according to 139, wherein the method comprises maintaining the patch on the skin surface of the subject for 6 hours or longer.
141. The method according to 139, wherein the method comprises maintaining the patch on the skin surface of the subject for 12 hours or longer.
142. The method according to 139, wherein the method comprises maintaining the patch on the skin surface of the subject for 24 hours or longer.
143. The method according to any one of 129-138, wherein the method comprises removing the patch in 15 minutes or less after applying the patch to the skin surface of the subject.
144. The method according to 143, wherein the method comprises removing the patch in 5 minutes or less after applying the patch to the skin surface of the subject.
145. The method according to 143, wherein the method comprises removing the patch in 1 minute or less after applying the patch to the skin surface of the subject.
146. The method according to any one of 129-145, wherein the plurality of microneedles form an array of microneedles on the backing layer.
147. The method according to any one of 129-146, wherein the microneedles are separated from each other on the backing layer by an average distance of from 5 μm to 1000 μm.
148. The method according to 147, wherein the microneedles are separated from each other on the backing layer by an average distance of from 100 μm to 500 μm.
149. The method according to any one of 129-148, wherein the backing layer further comprises a pressure sensitive adhesive.
150. The method according to any one of 129-149, wherein each microneedle comprises 2 or more repeating lattice cell units.
151. The method according to any one of 129-149, wherein each microneedle comprises 5 or more repeating lattice cell units.
152. The method according to any one of 129-151, wherein the microneedle comprises a gradient in the lattice cell units such that the density of lattice cell units increases across a longitudinal axis of the microneedle.
153. The method according to any one of 129-152, wherein the lattice cell unit comprises a lattice shape selected from the group consisting of tetrahedral, Kagome, rhombic, icosahedral, Voronoi and triangular.
154. The method according to any one of 129-153, wherein each microneedle comprises lattice cell units having a size of from 100 μm to 1000 μm.
155. The method according to 154, wherein each microneedle comprises lattice cell units having a size of from 200 μm to 500 μm.
156. The method according to any one of 129-155, wherein the lattice microstructure comprises a plurality of struts.
157. The method according to 156, wherein the lattice microstructure comprises struts having a thickness of from 25 μm to 150 μm.
158. The method according to 156, wherein the lattice microstructure comprises struts having a thickness of from 50 μm to 100 μm.
159. The method according to 156, wherein the lattice microstructure comprises struts having a thickness of from 70 μm to 90 μm.
160. The method according to any one of 129-159, wherein each microneedle comprises a square pyramidal or conical projection shape.
161. The method according to any one of 129-159, wherein each microneedle comprises an obelisk projection shape.
162. The method according to any one of 129-161, wherein each microneedle has a length of from 500 μm to 2000 μm.
163. The method according to 162, wherein each microneedle has a length of from 700 μm to 1200 μm.
164. The method according to any one of 129-163, wherein each microneedle has a base width of from 100 μm to 700 μm.
165. The method according to 164, wherein each microneedle has a base with of from 200 μm to 400 μm.
166. The method according to any one of 129-165, wherein lattice structure has a volume of from 0.01 μL to 2 μL.
167. The method according to 166, wherein the lattice microstructure has a volume of 0.1 μL.
168. The method according to any one of 129-167, wherein each microneedle comprises:
a tip section comprising a solid structure;
a body section comprising a lattice structure; and
a base section comprising a solid structure.
169. The method according to 168, wherein the tip section comprises a length of from 25 μm to 500 μm.
170. The method according to any one of 168-169, wherein the tip section comprises a base width of 50 μm to 300 μm.
171. The method according to any one of 168-170, wherein the microneedle has a tip diameter of from 0.1 μm to 10 μm.
172. The method according to any one of 168-171, wherein the body section comprises a length of from 50 μm to 1000 μm.
173. The method according to any one of 168-172, wherein the body section comprises a width of 50 μm to 300 μm.
174. The method according to any one of 168-172, wherein the base section comprises a length of from 25 μm to 500 μm.

175. The method according to any one of 168-172, wherein the base section comprises a base width of 50 μm to 300 μm.
176. The method according to any one of 129-175, wherein the each microneedle is formed from a polymerizable material selected from the group consisting of polycaprolactone, polyalycolic acid, polylactic acid, polylactic-co-glycolic acid, polyethylene glycol, thiolenes, anhydrides, polyacrylic acid, poly methylmethacrylate, trimethylolpropane triacrylate (TMPTA) monomer, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof.
177. The method according to any one of 129-175, wherein the lattice microstructure of one or more microneedles is formed from polyethylene glycol dimethacrylate (PEGDMA).
178. The method according to any one of 129-177, wherein one or more microneedles is formed from a biodegradable polymerizable material.
179. The method according to any one of 129-177, wherein one or more microneedles is dissolvable in an aqueous medium.
180. A system for making a polymeric microneedle comprising a lattice microstructure having one or more lattice cell units, the system comprising:
   a micro-digital light projection system comprising:
      a light beam generator component; and
      a light projection monitoring component;
   a liquid interface polymerization module comprising a build elevator and a build surface configured for generating the microneedle from a polymerizable composition positioned therebetween.
181. The system according to 180, wherein the light beam generator component comprises:
   a light source;
   a tube lens; and
   one or more projection lenses.
182. The system according to any one of 180-181, wherein the light beam generator component comprises two projection lenses.
183. The system according to 182, wherein the projection lenses are magnification lenses.
184. The system according to 183, wherein the projection lenses provide for 2-fold to 10-fold magnification.
185. The system according to any one of 180-184, wherein the light projection monitoring component comprises a photodetector.
186. The system according to 185, wherein the photodetector comprises a charge-coupled device (CCD).
187. The system according to any one of 180-186, wherein the system further comprises a processor comprising memory operably coupled to the processor wherein the memory comprises instructions stored thereon, which when executed by the processor, cause the processor to:
   a) irradiate a polymerizable composition positioned between a build elevator and a build surface to generate a polymerizable composition comprising a first polymerized region of the polymerizable composition in contact with the build elevator and a first non-polymerized region of the polymerizable composition in contact with the build surface;
   b) displace the build elevator away from the build surface;
   c) irradiate the first non-polymerized region of the polymerizable composition to generate a second polymerized region of the polymerizable composition in contact with the first polymerized region and a second non-polymerized region in contact with the build surface; and
   d) repeat steps a)-c) in a manner sufficient to generate the polymer microneedle comprising a lattice microstructure.
188. The system according to 187, wherein memory comprises instructions stored thereon, which when executed by the processor cause the processor to irradiate the polymerizable composition for a duration sufficient to bond the first polymerized region of the polymerizable composition to the build elevator.
189. The system according to any one of 187-188, wherein the memory comprises instructions stored thereon, which when executed by the processor cause the processor to displace the build elevator in predetermined increments of from 0.5 μm to 1.0 μm.
190. The system according to any one of 180-189, further comprising a source of the polymerizable composition.
191. The system according to 190, wherein the system is configured to add polymerizable composition to the build surface after each displacement of the build elevator away from the build surface.
192. The system according to any one of 181-191, wherein the light source is configured to irradiate through the build surface.
193. The system according to any one of 180-192, wherein at least part of the build surface is permeable to a polymerization inhibitor.
194. The system according to 193, wherein the polymerization inhibitor is oxygen.
195. The system according to any one of 180-194, wherein the memory comprises instructions stored thereon, which when executed by the processor cause the processor to determine a focal plane on the build surface from the micro-digital light projection system.
196. The system according to 195, wherein the memory comprises instructions stored thereon, which when executed by the processor cause the processor to determine the focal plane by:
   irradiating the build surface with a stroboscopic light source through the tube lens;
   displacing the build surface until the light is focused on the build surface through the tube lens.
197. The system according to 196, wherein the memory comprises instructions stored thereon, which when executed by the processor cause the processor to irradiate the build surface with a plane of light having a projected image pattern with the stroboscopic light source.
198. The system according to any one of 196-197, wherein the memory comprises instructions stored thereon, which when executed by the processor cause the processor to irradiate the build surface with a plane of light having a projected image pattern with the stroboscopic light source.
199. The system according to any one of 196-198, wherein the memory comprises instructions stored thereon, which when executed by the processor cause the processor to displace the build surface until the projected image pattern is in focus with the build surface.
200. The system according to any one of 196-199, wherein the memory comprises instructions stored thereon, which when executed by the processor cause the processor to generate an image stack comprising a plurality of the projected image patterns.

201. The system according to 200, wherein the memory comprises instructions stored thereon, which when executed by the processor cause the processor to determine the focal plane of the build surface based on the generated image stack.

202. The system according to any one of 196-201, wherein the memory comprises instructions stored thereon, which when executed by the processor cause the processor to determine the focal plane through a displacement depth of the build surface of 400 μm or less.

203. The system according to any one of 180-202, wherein the system provides for generating a lattice microstructure resolution of from 1.0 μm to 4 μm.

204. The system according to any one of 180-202, wherein the system provides for generating a lattice microstructure resolution of from 1.5 μm to 3.8 μm.

205. The system according to any one of 180-204, wherein the polymerizable composition comprises a polymerizable material selected from the group consisting of polycaprolactone, polyalycolic acid, polylactic acid, polylactic-co-glycolic acid, polyethylene glycol, thiol-enes, anhydrides, polyacrylic acid, poly methylmethacrylate, trimethylolpropane triacrylate (TMPTA) monomer, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof.

206. The system according to 205, wherein the polymerizable composition comprises polyethylene glycol dimethacrylate (PEGDMA).

207. The system according to any one of 180-206, wherein the microneedle comprises 2 or more repeating lattice cell units.

208. The system according to any one of 180-206, wherein the microneedle comprises 5 or more repeating lattice cell units.

209. The system according to any one of 180-208, wherein the microneedle comprises a gradient in the lattice cell units such that the density of lattice cell units increases across a longitudinal axis of the microneedle.

210. The system according to any one of 180-209, wherein the lattice cell unit comprises a lattice shape selected from the group consisting of tetrahedral, Kagome, rhombic, icosahedral, Voronoi and triangular.

211. The system according to any one of 180-210, wherein the microneedle comprises lattice cell units having a size of from 100 μm to 1000 μm.

212. The system according to 211, wherein the microneedle comprises lattice cell units having a size of from 200 μm to 500 μm.

213. The system according to any one of 180-212, wherein the lattice microstructure comprises a plurality of struts.

214. The system according to 213, wherein the lattice microstructure comprises struts having a thickness of from 25 μm to 150 μm.

215. The system according to 213, wherein the lattice microstructure comprises struts having a thickness of from 50 μm to 100 μm.

216. The system according to 213, wherein the lattice microstructure comprises struts having a thickness of from 70 μm to 90 μm.

217. The system according to any one of 180-216, wherein the microneedle comprises a square pyramidal or conical projection shape.

218. The system according to any one of 180-216, wherein the microneedle comprises an obelisk projection shape.

219. The system according to any one of 180-218, wherein the microneedle has a length of from 500 μm to 2000 μm.

220. The system according to 219, wherein the microneedle has a length of from 700 μm to 1200 μm.

221. The system according to any one of 180-220, wherein the microneedle has a base width of from 100 μm to 700 μm.

222. The system according to 221, wherein the microneedle has a base with of from 200 μm to 400 μm.

223. The system according to any one of 180-222, wherein lattice microstructure has a volume of from 0.01 μL to 2 μL.

224. The system according to 223, wherein the lattice microstructure has a volume of 0.1 μL.

225. The system according to any one of 180-224, wherein the microneedle comprises:

a tip section comprising a solid structure;

a body section comprising a lattice structure; and a base section comprising a solid structure.

226. The system according to 225, wherein the tip section comprises a length of from 25 μm to 500 μm.

227. The system according to any one of 225-226, wherein the tip section comprises a base width of 50 μm to 300 μm.

228. The system according to any one of 225-227, wherein the microneedle has a tip diameter of from 0.1 μm to 10 μm.

229. The system according to any one of 225-228, wherein the body section comprises a length of from 50 μm to 1000 μm.

230. The system according to any one of 225-228, wherein the body section comprises a width of 50 μm to 300 μm.

231. The system according to any one of 225-230, wherein the base section comprises a length of from 25 μm to 500 μm.

232. The system according to any one of 225-230, wherein the base section comprises a base width of 50 μm to 300 μm.

233. The system according to any one of 180-232, wherein the microneedle is dissolvable in an aqueous medium.

234. A method of making a polymeric structure comprising a lattice microstructure having one or more lattice cell units, the method comprising:

a) irradiating a polymerizable composition positioned between a build elevator and a build surface to generate a polymerizable composition comprising a first polymerized region of the polymerizable composition in contact with the build elevator and a first non-polymerized region of the polymerizable composition in contact with the build surface;

b) displacing the build elevator away from the build surface;

c) irradiating the first non-polymerized region of the polymerizable composition to generate a second polymerized region of the polymerizable composition in contact with the first polymerized region and a second non-polymerized region in contact with the build surface; and d) repeating steps a)-c) in a manner sufficient to generate a polymeric structure comprising a lattice microstructure.

235. The method according to 234, wherein the polymerizable composition is in contact with the build elevator and the build surface.

236. The method according to 235, wherein the method comprises irradiating the polymerizable composition for a duration sufficient to bond the first polymerized region of the polymerizable composition to the build elevator.

237. The method according to any one of 234-236, wherein the build elevator is displaced in predetermined increments of from 0.5 μm to 1.0 μm.

238. The method according to 237, wherein the method further comprises adding polymerizable composition to the build surface after each displacement of the build elevator away from the build surface.

239. The method according to any one of 234-238, wherein the polymerizable composition is irradiated through build surface.

240. The method according to any one of 234-239, wherein the polymerizable composition is irradiated in the presence of a polymerization inhibitor.

241. The method according to any one of 234-240, wherein the polymerizable composition is continuously polymerized while displacing the build elevator away from the build surface.

242. The method according to any one of 240-241, wherein the build surface is permeable to the polymerization inhibitor.

243. The method according to 242, wherein the polymerization inhibitor is oxygen.

244. The method according to any one of 234-243, wherein the polymerizable composition is irradiated with light.

245. The method according to 244, wherein the polymerizable composition is irradiated with a micro-digital light projection system.

246. The method according to 245, wherein the micro-digital light projection system comprises:

a light beam generator component; and a light projection monitoring component.

247. The method according to 246, wherein the light beam generator component comprises:

a light source;

a tube lens; and one or more projection lenses.

248. The method according to 247, wherein the light beam generator component comprises two projection lenses.

249. The method according to 248, wherein the projection lenses are magnification lenses.

250. The method according to 249, wherein the projection lenses provide for 2-fold to 10-fold magnification.

251. The method according to any one of 246-250, wherein the light projection monitoring component comprises a photodetector.

252. The method according to 251, wherein the photodetector comprises a charge-coupled device (CCD).

253. The method according to any one of 246-252, wherein the method comprises determining a focal plane on the build surface from the micro-digital light projection system.

254. The method according to 253, wherein determining the focal plane on the build surface from the micro-digital light projection system comprises:

irradiating the build surface with a stroboscopic light source through the tube lens;

displacing the build surface until the light is focused on the build surface through the tube lens.

255. The method according to 254, wherein the build surface is irradiated with a plane of light having a projected image pattern with the stroboscopic light source.

256. The method according to any one of 254-256, wherein the build surface is displaced until the projected image pattern is in focus with the build surface.

257. The method according to any one of 254-256, wherein the focal plane on the build surface is determined with the photodetector.

258. The method according to any one of 254-257, wherein the method comprises generating an image stack comprising a plurality of the projected image patterns.

259. The method according to 258, wherein the focal plane of the build surface is determined from the generated image stack.

260. The method according to any one of 254-259, wherein the focal plane is determined through a displacement depth of the build surface of 400 μm or less.

261. The method according to any one of 245-260, wherein the micro-digital light projection system provides for a lattice microstructure resolution of from 1.0 μm to 4 μm.

262. The method according to 261, wherein the micro-digital light projection system provides for a lattice microstructure resolution of from 1.5 μm to 3.8 μm.

263. The method according to any one of 234-262, wherein the polymerizable composition comprises a polymerizable material selected from the group consisting of polycaprolactone, polyalycolic acid, polylactic acid, polylactic-co-glycolic acid, polyethylene glycol, thiol-enes, anhydrides, polyacrylic acid, poly methylmethacrylate, trimethylolpropane triacrylate (TMPTA) monomer, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof.

264. The method according to 263, wherein the polymerizable composition comprises polyethylene glycol dimethacrylate (PEGDMA).

265. The method according to any one of 234-264, wherein the polymeric structure is formed from a biodegradable polymerizable material.

266. The method according to any one of 234-264, wherein the polymeric structure is dissolvable in an aqueous medium.

267. The method according to any one of 234-266, wherein the polymeric structure comprises 2 or more repeating lattice cell units.

268. The method according to 267, wherein the polymeric structure comprises 5 or more repeating lattice cell units.

269. The method according to any one of 234-268, wherein the polymeric structure comprises a gradient in the lattice cell units such that the density of lattice cell units increases across a longitudinal axis of the polymeric structure.

270. The method according to any one of 234-269, wherein the lattice cell unit comprises a lattice shape selected from the group consisting of tetrahedral, Kagome, rhombic, icosahedral, Voronoi and triangular.

271. The method according to any one of 234-270, wherein the polymeric structure comprises lattice cell units having a size of from 100 μm to 1000 μm.

272. The method according to 271, wherein the polymeric structure comprises lattice cell units having a size of from 200 μm to 500 μm.

273. The method according to any one of 234-272, wherein the lattice microstructure comprises a plurality of struts.

274. The method according to 273, wherein the lattice microstructure comprises struts having a thickness of from 25 μm to 150 μm.

275. The method according to 273, wherein the lattice microstructure comprises struts having a thickness of from 50 μm to 100 μm.

276. The method according to 273, wherein the lattice microstructure comprises struts having a thickness of from 70 μm to 90 μm.

277. The method according to any one of 234-276, wherein the polymeric structure has a length of from 500 μm to 2000 μm.

278. The method according to 277, wherein the polymeric structure has a length of from 700 μm to 1200 μm.

279. The method according to any one of 234-278, wherein the polymeric structure has a base width of from 100 μm to 700 μm.

280. The method according to 279, wherein the polymeric structure has a base with of from 200 μm to 400 μm.

281. The method according to any one of 234-280, wherein lattice microstructure has a volume of from 0.01 μL to 2 μL.

282. The method according to 281, wherein the lattice microstructure has a volume of 0.1 μL.

283. A system for making a polymeric structure comprising a lattice microstructure having one or more lattice cell units, the system comprising:

a micro-digital light projection system comprising:

a light beam generator component; and a light projection monitoring component;

a liquid interface polymerization module comprising a build elevator and a build surface configured for generating the polymeric structure from a polymerizable composition positioned therebetween.

284. The system according to 283, wherein the light beam generator component comprises:

a light source;

a tube lens; and one or more projection lenses.

285. The system according to any one of 283-284, wherein the light beam generator component comprises two projection lenses.

286. The system according to 285, wherein the projection lenses are magnification lenses.

287. The system according to 286, wherein the projection lenses provide for 2-fold to 10-fold magnification.

288. The system according to any one of 283-287, wherein the light projection monitoring component comprises a photodetector.

289. The system according to 288, wherein the photodetector comprises a charge-coupled device (CCD).

290. The system according to any one of 283-289, wherein the system further comprises a processor comprising memory operably coupled to the processor wherein the memory comprises instructions stored thereon, which when executed by the processor, cause the processor to:

a) irradiate a polymerizable composition positioned between a build elevator and a build surface to generate a polymerizable composition comprising a first polymerized region of the polymerizable composition in contact with the build elevator and a first non-polymerized region of the polymerizable composition in contact with the build surface;

b) displace the build elevator away from the build surface;

c) irradiate the first non-polymerized region of the polymerizable composition to generate a second polymerized region of the polymerizable composition in contact with the first polymerized region and a second non-polymerized region in contact with the build surface; and d) repeat steps a)-c) in a manner sufficient to generate the polymeric microstructure comprising a lattice microstructure.

291. The system according to 290, wherein memory comprises instructions stored thereon, which when executed by the processor cause the processor to irradiate the polymerizable composition for a duration sufficient to bond the first polymerized region of the polymerizable composition to the build elevator.

292. The system according to any one of 290-291, wherein the memory comprises instructions stored thereon, which when executed by the processor cause the processor to displace the build elevator in predetermined increments of from 0.5 μm to 1.0 μm.

293. The system according to any one of 291-292, further comprising a source of the polymerizable composition.

294. The system according to 293, wherein the system is configured to add polymerizable composition to the build surface after each displacement of the build elevator away from the build surface.

295. The system according to any one of 283-294, wherein the light source is configured to irradiate through the build surface.

296. The system according to any one of 283-295, wherein at least part of the build surface is permeable to a polymerization inhibitor.

297. The system according to 296, wherein the polymerization inhibitor is oxygen.

298. The system according to any one of 283-297, wherein the memory comprises instructions stored thereon, which when executed by the processor cause the processor to determine a focal plane on the build surface from the micro-digital light projection system.

299. The system according to 298, wherein the memory comprises instructions stored thereon, which when executed by the processor cause the processor to determine the focal plane by:

irradiating the build surface with a stroboscopic light source through the tube lens;

displacing the build surface until the light is focused on the build surface through the tube lens.

300. The system according to 299, wherein the memory comprises instructions stored thereon, which when executed by the processor cause the processor to irradiate the build surface with a plane of light having a projected image pattern with the stroboscopic light source.

301. The system according to any one of 299-300, wherein the memory comprises instructions stored thereon, which when executed by the processor cause the processor to irradiate the build surface with a plane of light having a projected image pattern with the stroboscopic light source.

302. The system according to any one of 299-301, wherein the memory comprises instructions stored thereon, which when executed by the processor cause the processor to displace the build surface until the projected image pattern is in focus with the build surface.

303. The system according to any one of 299-302, wherein the memory comprises instructions stored thereon, which when executed by the processor cause the processor to generate an image stack comprising a plurality of the projected image patterns.

304. The system according to 303, wherein the memory comprises instructions stored thereon, which when executed by the processor cause the processor to determine the focal plane of the build surface based on the generated image stack.

305. The system according to any one of 299-304, wherein the memory comprises instructions stored thereon, which when executed by the processor cause the processor to determine the focal plane through a displacement depth of the build surface of 400 μm or less.

306. The system according to any one of 283-305, wherein the system provides for generating a lattice microstructure resolution of from 1.0 μm to 4 μm.

307. The system according to any one of 283-305, wherein the system provides for generating a lattice microstructure resolution of from 1.5 μm to 3.8 μm.

308. The system according to any one of 283-307, wherein the polymerizable composition comprises a polymerizable material selected from the group consisting of polycaprolactone, polyalycolic acid, polylactic acid, polylactic-co-glycolic acid, polyethylene glycol, thiol-enes, anhydrides, polyacrylic acid, poly methylmethacrylate, trimethylolpropane triacrylate (TMPTA) monomer, polyvinyl alcohol, polyvinylpyrrolidone, vinyl carbonates, vinyl esters, acrylamides, hyaluronic acid, chitosan, collagen, gelatin, carboxymethylcellulose, and blends or copolymers thereof.

309. The system according to 308, wherein the polymerizable composition comprises polyethylene glycol dimethacrylate (PEGDMA).

EXPERIMENTAL

The following examples are offered by way of illustration and not by way of limitation. Specifically, the following examples are of specific embodiments for carrying out the present disclosure. The examples are for illustrative purposes only and are not intended to limit the scope of the present disclosure in any way. Efforts have been made to ensure accuracy with respect to numbers used (e.g., amounts, temperatures, etc.), but some experimental error and deviation should, of course, be allowed for.

Example 1

By combining a reduction lens optics system for single-digit-micron-resolution, an in-line camera system for contrast-based sharpness optimization, and Continuous Liquid Interface Production (CLIP) technology for high scalability, a single-digit-micron-resolution CLIP-based 3D printer that can create millimeter-scale 3D prints with single-digit-micron resolution features in just a few minutes. A simulation model is developed in parallel to probe the fundamental governing principles in optics, chemical kinetics, and mass transport in the 3D printing process. A print strategy with tunable parameters informed by the simulation model is adopted to achieve both the optimal resolution and the maximum print speed. Taken together, high-resolution 3D CLIP printer demonstrated herein provides for applications including but not limited to biomedical, MEMS, and microelectronics.

In this example, a high-resolution CLIP technology that allows the fabrication of 3D structures containing single-digit-micron features at a print speed that is 105 faster than commercially available high-resolution 3D printers (e.g., NanoScribe). This is accomplished by combining the CLIP technology with a custom-designed projection optical lens and an in-line contrast-based focusing system. To maneuver the shallow depth of focus for a high magnification objective lens, a robust calibration platform is developed to locate the optimal focal plane thus resolving the fine details of the projected patterns with reproducibility. To achieve an understanding of photopolymerization kinetics on print resolution and the impact of resin transport on print speed with this system, a numerical model is introduced that considers all fundamental elements in the high-resolution 3D CLIP printing system, including optical projection, photopolymerization reaction kinetics, and resin mass transport. This model provides for a printing strategy that utilizes the understanding of fundamental transport phenomena and determine print parameters for the printer software control system. In addition, the model described herein provides fundamental insights into 3D CLIP printing in general, with accurate predictions of the surface finish of a printed part, dead-zone thickness and resin curing during the 3D printing process. A new single-digit-micron-resolution 3D CLIP-100 based printer is demonstrated with a custom designed projection optics lens system, in-line focusing system, and a software-controlled printing process informed by parameters from first principles-based model.

Materials and Methods

High-Resolution CLIP Hardware Design

The single-digit-micron-resolution CLIP-based 3D printer hardware components can be divided into four components:

(1) Projection optics components: Light engine (3DLP9000, Digital Light Innovations, TX), tube lens (SM1L10, Thorlabs, NJ; 54-774 Edmund Optics, NJ), projection lens (5× Mitutoyo Plan Apo Infinity Corrected Long WD Objective for 1.5 μm resolution; 2× Mitutoyo Plan Apo Infinity Corrected Long WD Objective for 3.8 μm resolution, Edmund optics, NJ).

(2) Oxygen permeable resin vat: a custom designed 3D-printed resin vat with an oxygen permeable window (Teflon AF2400 film, Random Technology, CA) is the main component for achieving the CLIP technology; it allows the UV to penetrate through for photopolymerization and allows oxygen to permeate through for inhibiting photopolymerization directly above the window within the ~50-80 μm thickness of the dead-zone.

(3) Build platform: a high-precision vertical translation stage (GTS70V, Newport, CA) is used to finely adjust the vertical position and an SEM mount (TedPella Inc, Reddings, CA) was used as a build platform onto where the printed parts attach.

(4) Real-time projection monitoring sub-system for focusing: The focusing sub-system consists of a beamsplitter cube (CCM1-4ER, Thorlabs, NJ) mounted with UVFS plate beam splitter 30:70 (R: T) (BSS10R, Thorlabs, NJ), a strobe light illumination system (RL3536-WHIIC, Advanced Illumination, Rochester, VT) and a UV camera (CS126MU, Thorlabs, NJ) detector attached to the adjustable tube lens (SM1V10, Thorlabs, NJ) for focusing and monitoring the UV projection.

High-Resolution CLIP Software Design

Control of the single-digit-micron-resolution CLIP-based 3D printer is handled by CLIP3DGUI, a custom software application developed in the Qt framework (Qt Creator, Finland) using C++. CLIP3DGUI controls the operation of the light engine, translation stage, and print process through a set of user-controlled parameters that are optimized for each print.

Light engine: 2560×1600 1-bit binary image slices generated from the 3D CAD design are imported and then processed with an image encoding pipeline where 1-bit binary images are encoded into 24-bit RGB images, resulting in 24 1-bit images being in stored in a single frame. The image encoding results in high image throughput while simultaneously allowing for a low framerate of streamed images to the light engine, thus avoiding common pitfalls including dropped frames and inconsistent framerates. Encoded images are streamed to the light engine through an HDMI cable and the exposure time, dark time, and LED intensity are all programmatically controlled through lookup tables uploaded to the light engine flash memory.

Stage: Translation stage parameters including velocity, acceleration, and jerk must be optimized 736 to allow for swift and precise motion between layers. However, increasing the velocity, acceleration, and jerk parameters also results in larger forces on the part and increased mechanical wear of the translation stage internals.

Print process: A series of print process parameters are used to further optimize the print including layer thickness, initial exposure time for adhesion to the build platform, system re-sync rates, translation stage limits, and starting position.

Print Script: Exposure time, dark time, LED intensity, stage velocity, and stage acceleration can all be controlled on a layer-by-layer basis to optimize for the exact feature being printed at that time. This allows for the potential of printing vastly different geometries requiring vastly different parameters within the same print.

High-Resolution CLIP Materials Preparation and Resin Formulation

The resins used in the experiments were formulated with trimethylolpropane triacrylate (TMPTA) monomer, diphenyl(2,4,6-trimethylbenzoyl) phosphine oxide (TPO) photoinitiator, and phenol, 2-750 (5-chloro-2H-benzotriazol-2-yl)-6-(1,1-dimethylethyl)-4-methyl (BLS1326) benzotriazole-type ultraviolet (UV) light absorber, which were all purchased from Sigma-Aldrich (MO, USA). A variety of resins with different mixing ratios were used: 2.5 wt % TPO photoinitiator, 0.3 wt % BLS1326 with TMPTA. A cup of mixed solutions was placed in a THINKY ARE-310 centrifugal mixer (THINKY, CA, USA) and centrifuged for 30 minutes at 2000 revolutions per minute (rpm) while simultaneously rotating the cup in the opposite direction at 2200 rpm. EPU-40 elastomeric resin was purchased from Carbon 3D (CA, USA). Isopropyl alcohol (IPA, 99%) was used as a rinsing solvent for all printed samples and was obtained from Fisher Scientific (MA, USA).

High-Resolution CLIP Materials Rheological Measurements

The rheological measurements were done on a TA Instrument (ARES-G2) Rheometer (TA Instruments, New Castle, DE). Rheology characterization on TMPTA+2.5 wt % TPO photoinitiator, 0.3 wt % BLS1326 and EPU-40 were measured. A parallel plate with 25 mm diameter was used and approximately 250 μL of solution was used for each experiment. Characterizations include: (1) flow sweep of the TMPTA resin was done at temperature 20° C. for soak time 120 s, with shear rate sweeping from 0.01 to 100 1/s. (2) flow sweep of the EPU-40 resin is done at temperature 20° C. for soak time 120 s, with shear rate sweeping from 0.01 to 1000 1/s. (3) Stress relaxation characterization of the TMPTA resin is done at temperature 20° C. for a soak time of 60 s, with stress relaxation duration 100s under strain % 500%. (4) Stress relaxation characterization of the EPU 40 resin is done at temperature 20° C. for a soak time of 60 s, with stress relaxation duration 100s under strain % 500%.

High-Resolution CLIP Stefan Force Measurements

Measurements of the Stefan forces experienced by the build-platform is conducted using a load-cell (Futek, Irvine, CA) with a 1 lb maximum force load. The load-cell is installed securely in between the build platform and force readout was conducted at frequency of 0.005 Hz. The Stefan force is extracted at the regime where the force has reached steady state. The force experienced for each print radius is obtained from calculating the force amplitude read-out from each step movement and averaged over 100s.

High-Resolution CLIP Data Collection on NanoScribe

NanoScribe's TPP technology was used as a reference to compare the print speed of a high-resolution 3D printer. The 3D structure was printed on a DiLL substrate on the IPO coated side. The IPO side was identified and confirmed using a multimeter, with a resistance readout of 200 Ohms. The objective used to pattern the design is the 25× objective with the adjustable ring placed at the mark Glyc and the resin used in this work is IP-S. When printing was completed, the printed part was cleaned by dipping in the PGMEA developer for 20 minutes followed by a quick rinse with IPA and air dried with a compressed air gun.

High-Resolution Contrast-Based Focal Plane Optimization

Figure 9A:
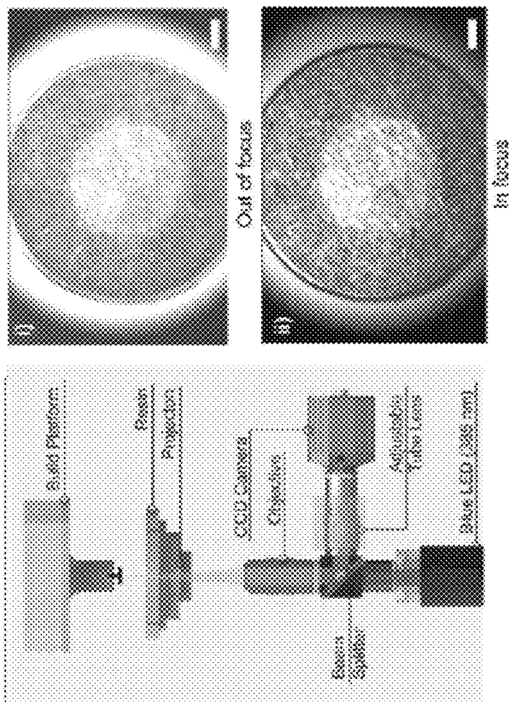
FIGS. 9A-9E depict a contrast-based focus algorithm for optimization of the projection focal plane.

The contrast-based focal plane optimization contains the following steps. We first perform a coarse adjustment to focus the CCD camera on the build platform. The coarse tuning is performed by fixing the build platform at a specific location while rotating the adjustable tube lens. While we manually flash a strobe light onto the build platform, we focus on the build platform (SEM mount) by tuning the tube lens (FIG. 9A). FIG. 9A(i) and FIG. 9A(ii) illustrate the difference between in- and out-of-focus.

Figure 9B:
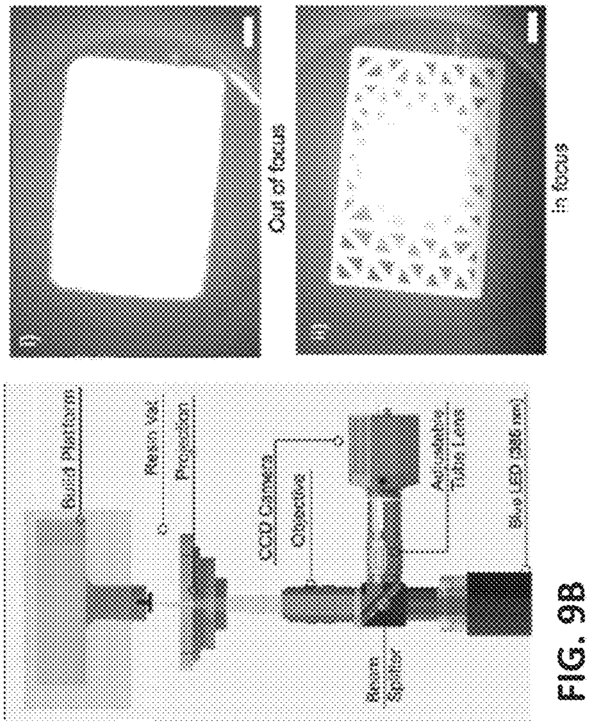

Next, we project a mesh pattern from the UV light engine with the minimum feature width of 45 pixels (67.5 μm in 5× magnification objective and 168 μm in 2× magnification objective) pattern to an empty vat and drive the build platform in the z-axis until the projected pattern is roughly in focus (FIG. 9B).

Figure 9C:
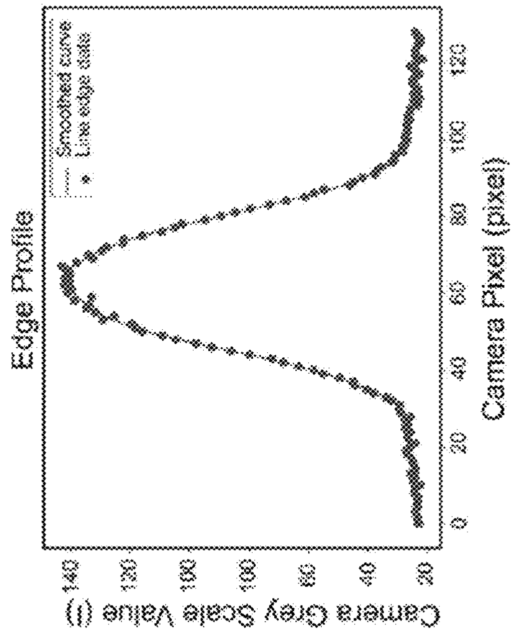

Finally, we perform a fine tuning with a resin material with photoinitiator excluded and analyze the through-focus image stacks with a sharpness analysis algorithm (FIG. 9C).

High-Resolution CLIP Image Slices and 3D Printing Procedure

The 3D CAD designs were either (1) Custom-designed using SolidWorks or Fusion360 in-house or (2) Acquired from online repositories (GRABCAD and cgtrader). nTopology (nTopology, NY) was used to generate certain lattice designs. Once the designs were generated Netfabb (Autodesk, CA) was used to slice them into certain layer thickness. All prints in this study were sliced at 0.5 μm layer thickness; as Netfabb could not slice at 0.5 μm, each design was scaled by two in the vertical direction and then sliced at 1 μm layer thickness. No modification to the slices was applied. The slices were, then, applied to our custom software for 3D printing.

Results

Projection Optics System for Achieving Single-Digit-Micron-Resolution

Figure 10A:
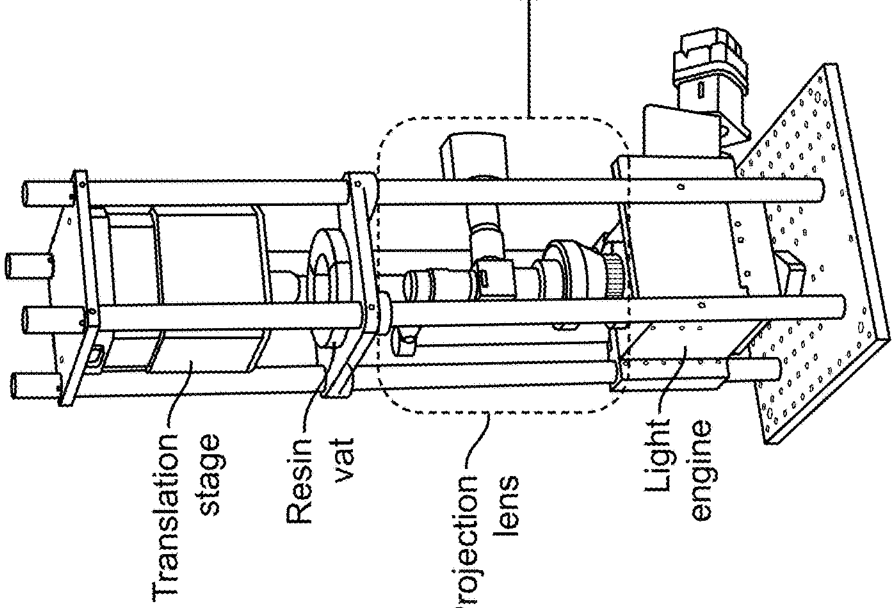
FIGS. 10A-10C depict single-digit-micron-resolution continuous liquid interface production (CLIP)-based 3D printer setup schematic and printing process according to certain embodiments.
Figure 10A:
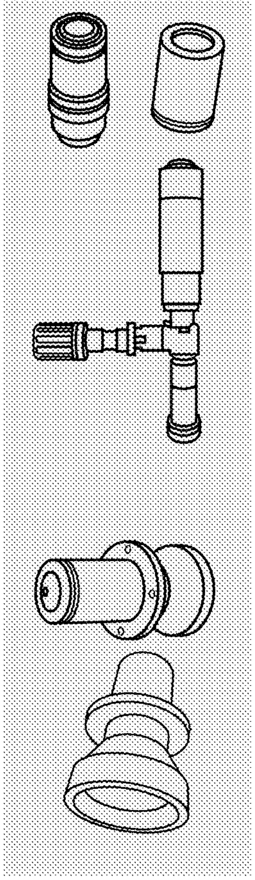
Figure 10B:
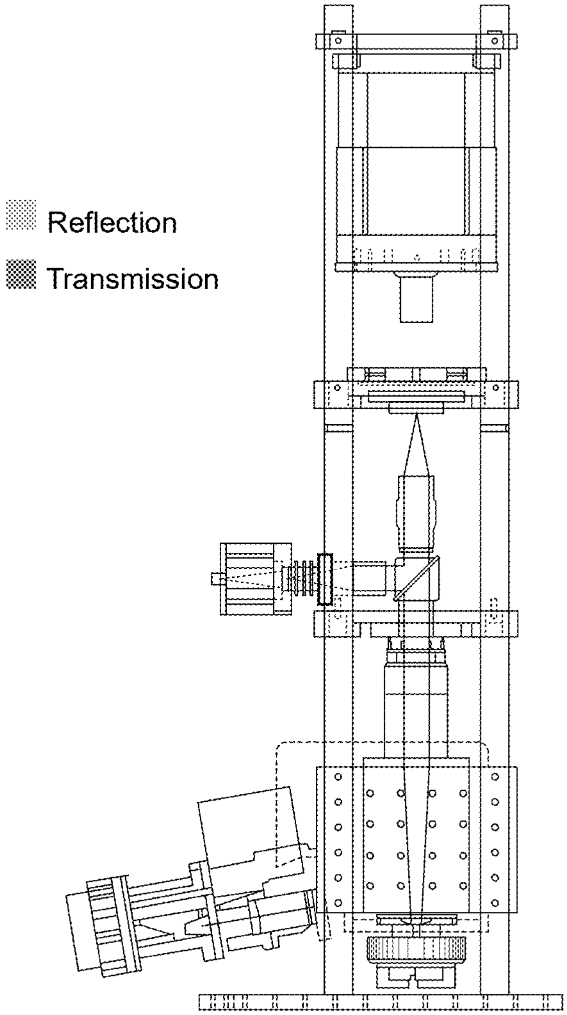

The single-digit-micron-resolution CLIP-based 3D printer system has been designed and implemented in our lab. The system is based on a combination of the CLIP printing technology and a reduction optics system to achieve fast print speed, smooth surface, and high-resolution print (FIG. 10A). The projection optics system consists of a tube lens and microscope objective with built-in magnifications of 2× and 5× to shrink the 7.6 μm native pixel size of the digital micromirror device (DMD) to 3.8 μm or 1.5 μm, respectively. A real-time projection pattern monitoring and focal plane adjustment system that contains a beam-splitter and a charge-coupled device (CCD) camera is designed in the projection light path (FIG. 10B) (As described above in the Materials and Methods section).

Figure 10C:
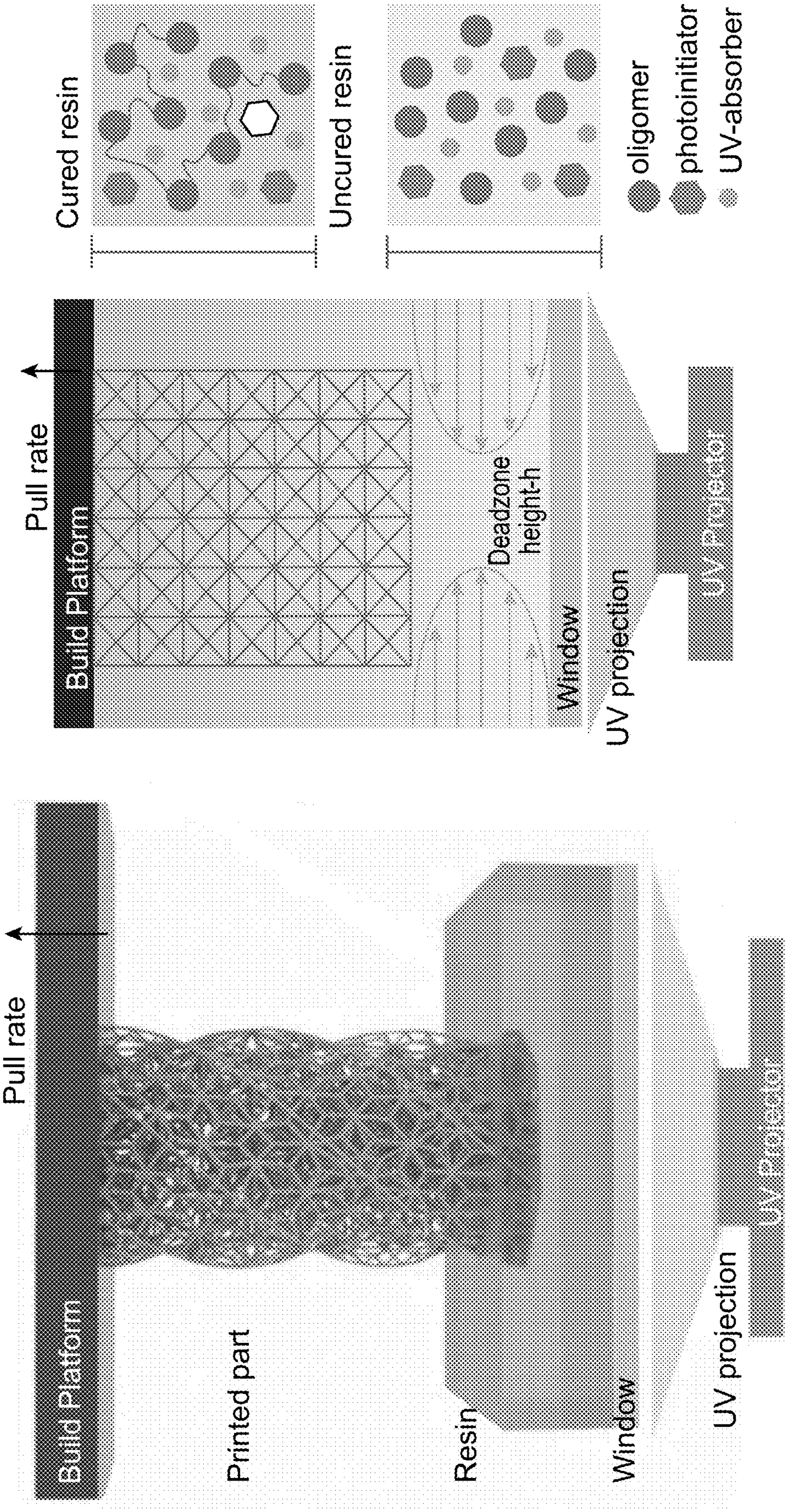

The CLIP printing process is achieved through an oxygen permeable window that creates a thin dead-zone which inhibits photopolymerization for continuous fabrication of printed parts (FIG. 10C). This dead-zone allows a continuous flow of resin replenishment, thus eliminating the delamination of the printed part from the window, which is known to be the rate limiting step in SLA, DLP and PμSL.

Contrast-Based Focusing Mechanism to Optimize the Focal Plane and Print Resolution Due to the shallow depth of focus (14 μm) of high-magnification objectives, a precise contrast-based focusing mechanism to the 3D printer system is implemented to achieve the single-digit-micron-resolution and optimize the overall projection optics setup. The in-line focusing sub-system consists of a beam splitter, a tube lens, a couple of microscope objective candidates, and a CCD camera (FIGS. 9A and 9B). This sub-system obtains the through-focus sharpness of the projected pattern, and we verified the performance by comparing the sharpness Modulation Transfer Function (MTF) and the printed pattern side-by-side. The contrast-based focusing approach demonstrated that the projection optics can rapidly and reproducibly achieve the best focal plane for multiple setups containing different microscope objectives (2× and 5×).

Figure 9D:
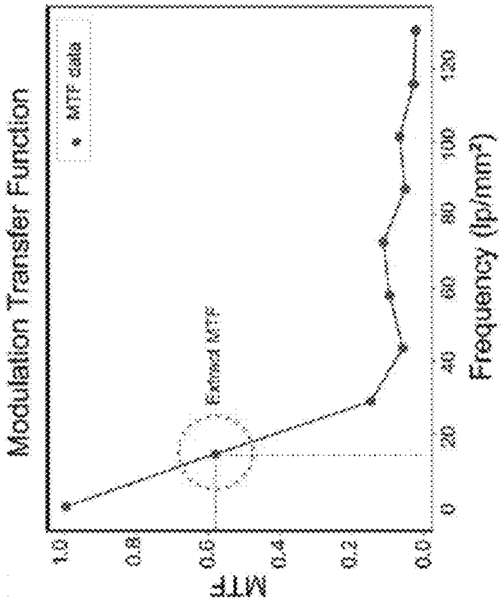
Figure 9E:
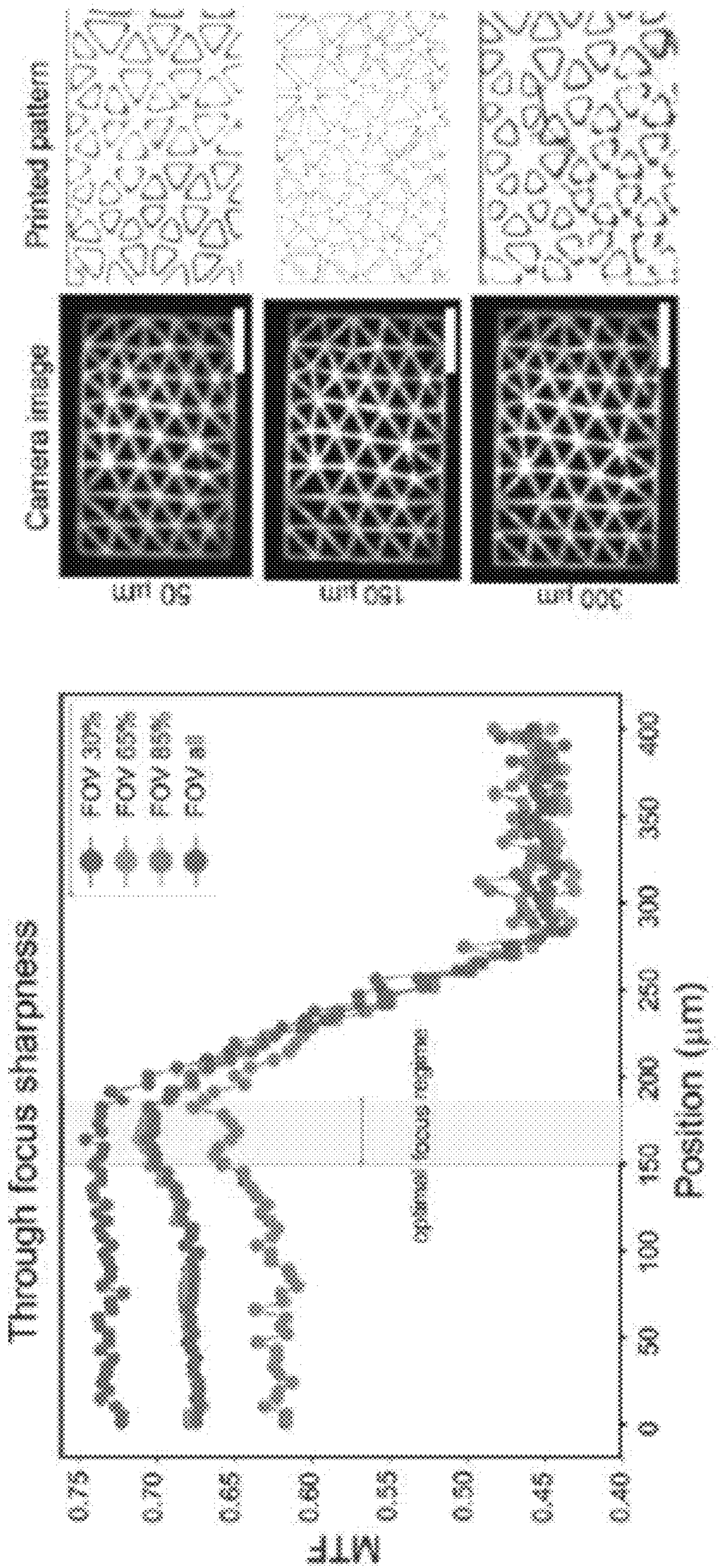

The contrast-based focal plane optimization method contains three separate steps: (1) Coarse Tuning I: Roughly tune the adjustable tube lens with strobe light illumination to bring the build platform in focus (FIG. 9A). (2) Coarse Tuning II: Roughly adjust the build platform translational z-stage to bring the projected pattern in focus (FIG. 9B) and repeat (1) and (2) until both the build-platform surface and the projected image are both in focus. (3) Fine Tuning: Finely scan through the z-direction (400 μm) with the translational z-stage and obtain a through-focus projected image z-stack (FIGS. 9C-9E). More details on implementation of contrast-based focusing algorithm can be found in the Materials and Methods section. The analysis scheme that extracts the sharpness information from the projected image is shown.

The MTF calculation is similar to the traditional optical transfer function (OTF) obtained from slanted edge images. The line edge profile for the projected mesh image is extracted from the center of the strut and the line spread function (LSF) is calculated with the first order derivative of the line edge profile. After obtaining the LSF, a Fast Fourier Transform (FFT) is applied to the LSF to obtain the MTF in units of line-pair (lp)/mm2. The full field-of-view MTF is extracted at a frequency of 12.6 lp/mm$^2$ and compared the through-focus MTF to obtain the optimal focal plane. Details on the algorithm are described in detail below.

Finally, a series of through-focus print results were obtained and compared with the projected image sharpness analysis. The through-focus sharpness results obtained from this analysis corroborates our experimental results (FIG. 9E). From the full scanning distance of 400 μm, we have observed the optimal focus position 150 μm away from the initial scanning position. Due to the shallow depth of focus (14 μm) of high-magnification objectives, it is observed that both the print performance and the sharpness degrade rapidly moving away from the optimal focal plane. Through this contrast-based z-directional focusing method, the optimal focus position for high-resolution 3D printing is identified.

High-Resolution CLIP Modeling of Optics, Momentum, and Mass Transport Compared to commercial CLIP 3D printers that have projection optics resolutions of 75-160 μm, the newly developed single-digit-micron-resolution CLIP-based 3D printer has a target resolution of 1.5-3.8 μm. With a 50× improvement of the resolution, the physics of the CLIP printing process is described and assign the optimal printing parameters to resolve the smallest possible features. To fully understand the high-resolution CLIP printing process, the three key physical models involved are described; (1) Optical model: the estimation of a single pixel projection width from the projection lens optics, (2) Fluidic model: the uncured resin flow profile during the vertical translation stage movement, and (3) Chemical model: the photopolymerization (curing) including the gradient of oxygen concentration.

Figure 11A:
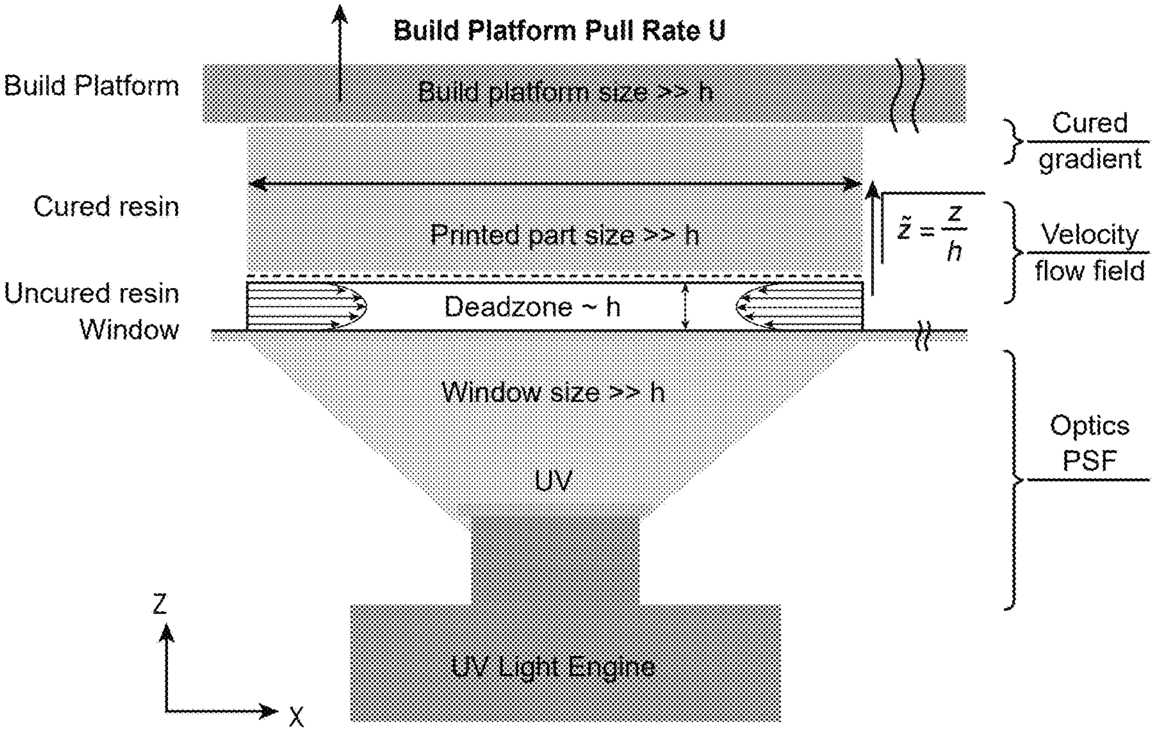
FIGS. 11A-11B depict a schematic of CLIP setup and printing process according to certain embodiments.
Figure 11B:
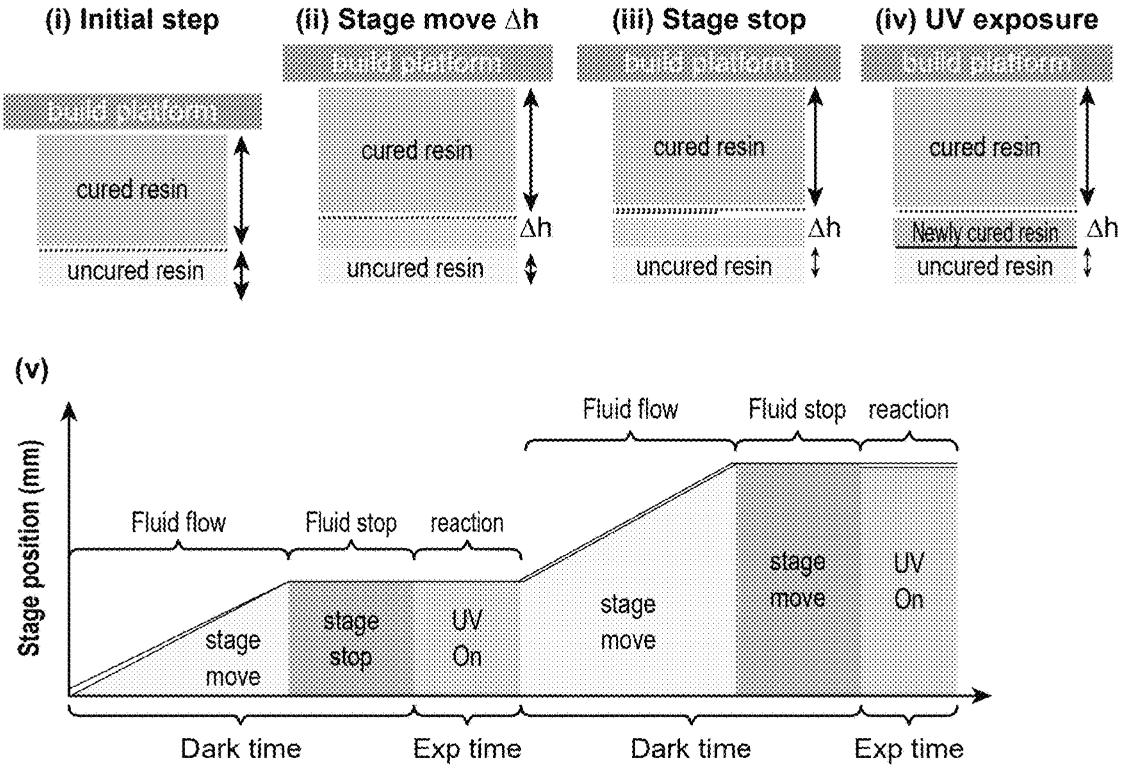

Components that are involved in a high-resolution CLIP printing process are shown in FIG. 11A. These include (from bottom to top) a UV light engine that illuminates UV projection at a wavelength of 385 nm, an oxygen permeable window, a dead-zone (height H) where uncured resin flows through, the cured resin part, and a build platform that travels at a step size Ah, at a pulling rate U. A general model is developed that covers a wide range of CLIP printers with various print resolution capabilities of 30-μm-resolution and 1.5-μm-resolution. After developing a numerical model to fully understand the CLIP process, the model to an actual 3D printing scenario is adopted where the process repeats through three basic steps (stage move, stage stop, and UV exposure) (FIG. 11B). Taken together, the multiphysics simulation tool enables the estimation of many crucial factors required for achieving a successful 3D print, such as, the spatial resolution of a 3D printed part, the maximum delamination force experienced for a given projection area, and the dead-zone thickness that is dependent on the printing parameters including dark time, exposure time, and UV intensity.

High-resolution 3D CLIP printing strategy

With the knowledge of the high-resolution 3D CLIP printing process, a general description of the printing strategy is developed as follows. For the first layer of the print, the photocurable resin undergoes a longer initial exposure step that overcomes the gap in between the uncured resin and build platform to allow the resin to successfully bond and attach to the build platform. The remaining layers are repeated through the following processes (FIG. 11B (i)). For the $n^{th}$ layer of the print, the stage moves upward (z direction) by an increment of Δh (layer thickness; typically, between 0.5 and 1 μm). This upward stage movement transiently creates a negative pressure within the dead-zone, resulting in resin replenishment from both left and right ends of the cured part (FIG. 11B (ii)) until resin flow into the gap is completed and the uniform pressure is restored. There is a minimum amount of time required for resin to travel to the center of the build part. Therefore, there is pause after the vertical stage movement to allow for the uncured resin to fully replenish the gap which has thickened by an increment of Ah (FIG. 11B (iii)). After the fluid has reached the deepest pixel region (center of the cured resin) and the resin flow is essentially at a quiescent state, we then expose the resin with the UV pattern for the $(n+1)^{th}$ layer, which cures an additional Ah of resin (FIG. 11B (iv)). These three steps of printing that involve stage movement, stage stoppage, and UV exposure, are repeated until the full 3D print is completed. The overall timeline and the print process are depicted in FIG. 11B (v). The estimation of the required stage traveling time and pausing time are grouped together as the “dark-time” and the duration of this “dark-time” is informed by this model.

High-Resolution CLIP Optics Modeling: Projection Optics Simulation

Figure 12A:
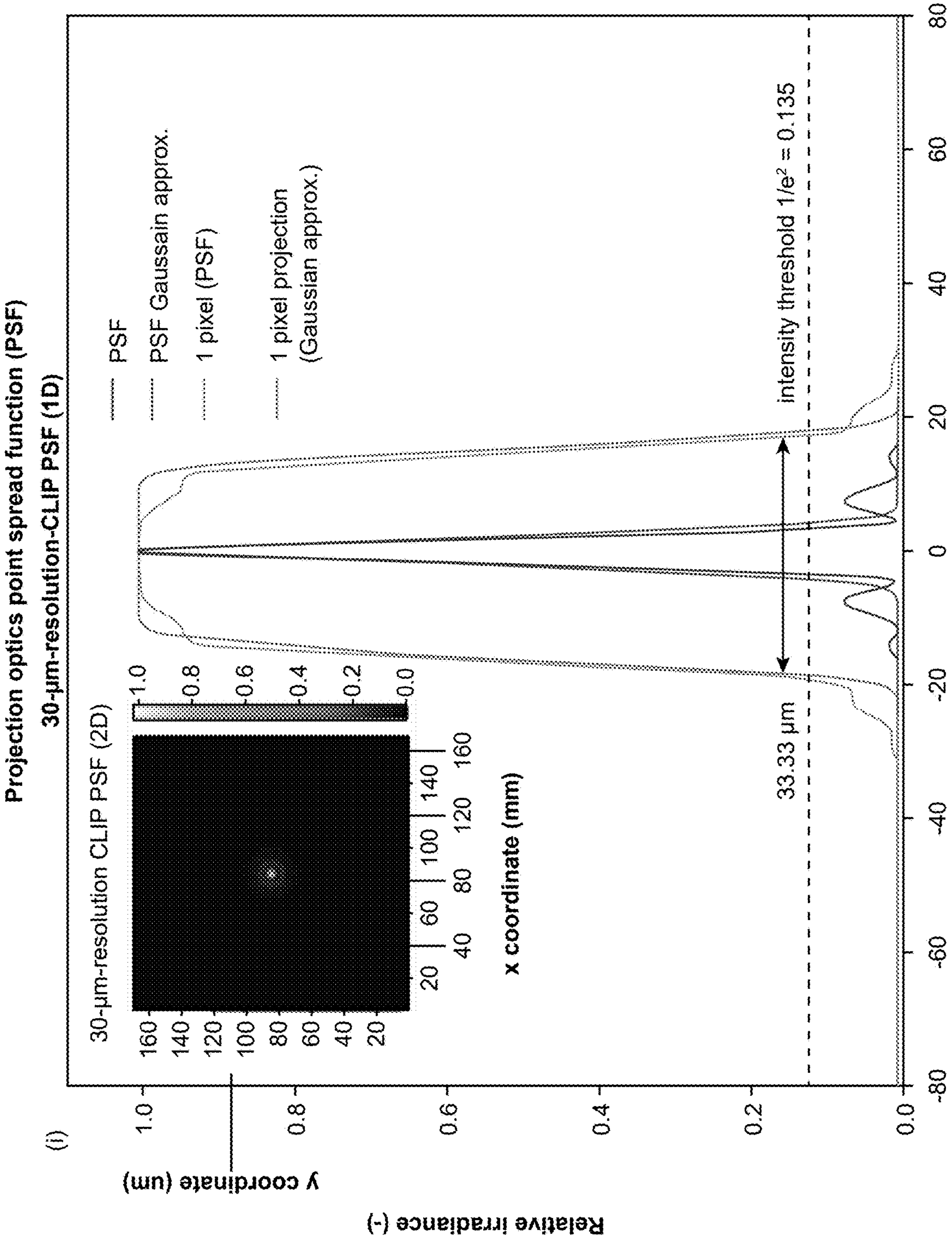
FIGS. 12A-12B depict a CLIP printing process model includes projection optics, velocity flow field, polymerization gradient, and final 3D printed structure according to certain embodiments.

Factors that govern the print resolution include the spatial distribution of the projection optics, exposure energy per unit area, and the physical-chemical characteristics of the photopolymer resin and printing parameters. We begin with our focus on the projection optics simulation. The incoherency of the UV reflected pattern from the DMD of the light engine allows us to model the final energy spread at the projection plane as the superposition of point spread functions (PSFs) of all pixels on the DMD surface via the spatial convolution equation:

$$f(x, y) * PSF(x, y) = \int_{\tau 1=-\infty}^{\infty} \int_{\tau 2=-\infty}^{\infty} f(\tau_1 \tau_2) \cdot PSF(x-\tau_1, y-\tau_2) d\tau_1 d\tau_2 \quad (1)$$

where ƒ(xx,yy) is the spatial intensity pattern projected through the DMD. A single pixel ƒ(xx,yy) is therefore:

$$f(x, y) = \begin{cases} \frac{\text{greyscale}}{255} & -m\frac{d_x}{2} < x < m\frac{d_x}{2},\ -m\frac{d_x}{2} < y < \frac{d_y}{2} \\ 0 & x < -m\frac{d_x}{2},\ m\frac{d_x}{2} < x,\ y < -m\frac{d_y}{2},\ m\frac{d_y}{2} < y \end{cases} \quad (2)$$

where $d_x$ and $d_y$ are the lengths of the micro-mirror along the x and y axis, m is the magnification of the projection optics, and grey scale is the intensity of a single DMD pixel. The spatial convolution equation (Eq. (1)) determines the equivalent Gaussian distribution function (wo) in the focal plane of the projection optics. In FIG. 12A, the 2D cross-section of the fitted Gaussian curve and the effect of the spatial convolution of a pixel are shown for both the 30-μm-pixel and the 1.5-μm-pixel projection optics. Under the assumption that the width of the spot diameter is $1/e^2$ of maximum intensity, the single pixel projection width is simulated as 33.3 μm and 1.42 μm for 30-μm-pixel and 1.5-μm-pixel projection systems, respectively. Finally, the spot diameter at the focal plane can be expressed as the Gaussian distribution, where the UV intensity of an ideal point source on the projection plane at the given position of x and y is defined by:

$$I(x, y) = \frac{2P}{\pi\omega_0^2} e^{\left(\frac{-2(x^2+y^2)}{\omega_0^2}\right)} \quad (3)$$

where I(J/cm$^2$s) is the intensity distribution of the UV light, P (J/s) is the total power of the UV 228 light, and wo (Gaussian radius) is the half-width at the 1/e2 of Gaussian maximum intensity (I max). The x-y plane is the focal plane of the projection optics and is located just above the dead-zone surface in our experimental setup.

High-Resolution CLIP Kinetics Modeling: Photopolymerization Gradient Study

To develop our process model, we first adopt a basic reaction set commonly used to describe free radical polymerization similar to that presented by Dendukuri et al. In the first step, UV light incident on the sample photolyzes the photo-initiator to produce a pair of radicals. The UV light intensity varies through the sample height according to Beer's law.

$$r_a = \varphi\varepsilon[PI]I_0\exp(-\varepsilon[PI]z) \quad (4)$$

where φ is the quantum yield formation of initiating radicals, E is the molar extinction coefficient of the photoinitiator at 385 nm, $I_0$ is the UV intensity at the surface of the window, and [P]] is the concentration of the photoinitiator. Once the oxygen concentration is below a certain threshold, the photo-initiator radicals react with an unreacted monomer to initiate the chain polymerization. In the chain propagation step, the concentration of the growing radicals (R, $RM_n$) are lumped into term [X] and their formation propagates through a chain of reactions with other monomer molecules to form a larger radical with rate constant $k_p$. Then, radicals are consumed and terminated through two separate reactions: (1) chain termination (which is biomolecular in polymer radical) with rate constant $k_t$ and (2) oxygen inhibition reaction with rate constant $k_o$. In this model, only bimolecular termination is considered, while other modes of loss of radical such as trapping of radical species in the resulting polymeric gel are neglected, but likely are playing a role to some extent in diminishing the rate of termination relative to propagation.

$$r_c = k_t[\dot{X}]^2 + k_o[\dot{X}][O_2] \quad (5)$$

By making the quasi-steady approximation (radical concentration remains constant, that is the rate of initiation equals the rate of termination, $r_a=r_c$.) to describe the concentration of radicals we obtain:

$$\frac{-k_o[O_2] + \sqrt{(k_o[O_2])^2 + 4r_a k_t}}{2k_t} \quad (6)$$

By constructing the mass transport equations for oxygen and the unconverted oligomer [M], we can solve for their spatial-temporal concentration. The oxygen and oligomer transport and consumption inside the system are described by:

$$\frac{\partial[O_2]}{\partial t}=D_o\frac{\partial^2[O^2]}{\partial z^2}-k_o[O_2][\dot{X}] \quad (7)$$

$$-\frac{\partial[M]}{\partial t}=k_p[M][\dot{X}] \quad (8)$$

No flow is assumed so transport is by diffusion only, and the diffusion of the oligomer is assumed small, so it is neglected.

Nondimensionalizing (Eq. (7) using: $\tau=tD_o/H^2$, $\theta=[O_2]/[O_{2,eqb}]$, $\eta=z/H$ where $D_o$ is the diffusivity of oxygen in the oligomer, H is the height of the dead-zone thickness, and $[O_{2,eqb}]$ is the equilibrium concentration of oxygen at the surface of the oxygen permeable window, we obtain:

$$\frac{\partial\theta}{\partial\tau}=\frac{\partial^2\theta}{\partial\eta^2}-Da_1\theta\left(-\theta+\sqrt{\theta^2+\alpha\exp(-\beta\eta)}\right) \quad (9)$$

$$Da_1=\frac{k_o^2H^2[O_{2,eqb}]}{2k_tD_o},\ a=\frac{4\varphi\varepsilon[PI]I_0k_t}{k_o^2[O_{2,eqb}]^2},\ \beta=\varepsilon[PI]H$$

In the above, $Da_1$ is the dimensionless Damköhler number that quantifies the ratio of oxygen inhibition versus oxygen diffusion into the resin. The boundary conditions and initial condition in our system are:

$$\theta(0,\tau)=1$$

$$\frac{d\theta(1,\tau)}{d\eta}=0$$

$$\theta(\eta,0)=1$$

Where we assume the initial resin region is oxygenated and the flux of oxygen through the build platform is zero. Since the diffusivity of oxygen in the Teflon AF 2400 window is greater than the diffusivity of oxygen in the resin TMPTA, we assume oxygen can flow freely through the window and oxygen concentration is equal to $[O_{2,eqb}]$ at the window surface.

By nondimensionalizing $$(Eq.\ (8))\text{ with }\xi=[M]/[M_0],\ Da_2=\frac{k_pk_o[O_{2,eqb}]H^2}{2k_tD_o}$$

and setting $[M_o]$ to be the initial monomer concentration, we obtain:

$$-\frac{\partial\xi}{\partial t}=Da_2\xi(-\theta+\sqrt{\theta^2+\alpha\exp(-\beta\eta)} \quad (10)$$

The initial condition is set to be:

$$\xi(\eta,0)=0$$

and $Da_2$ is a second dimensionless Damköhler number.

Figure 13A:
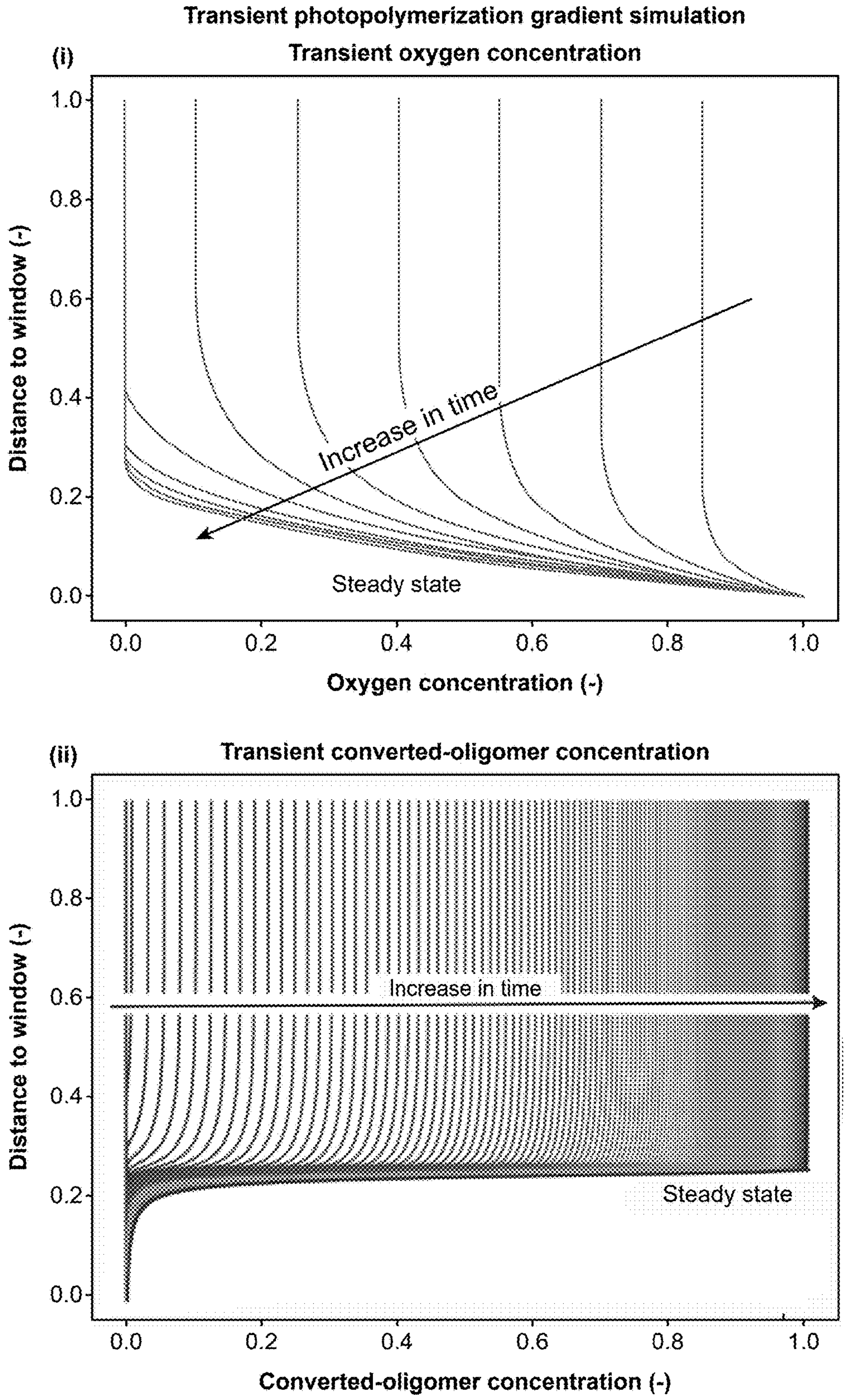
FIGS. 13A-13D depict kinetics modeling of a CLIP printing process according to certain embodiments.
Figure 13A:
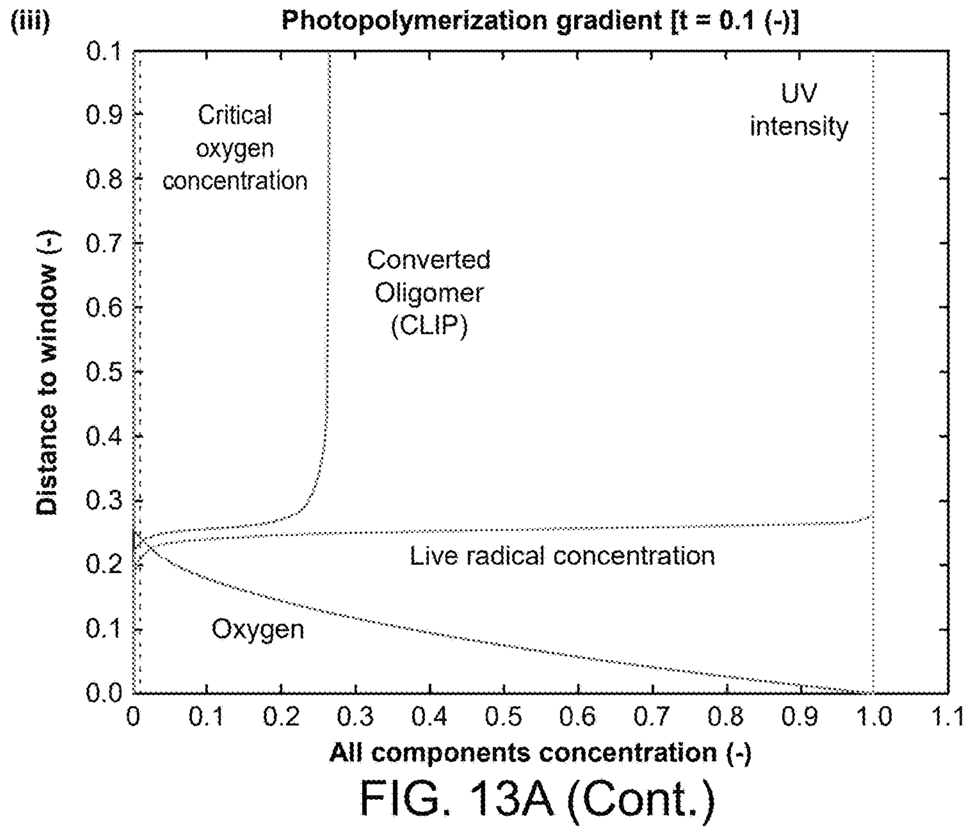
Figure 13B:
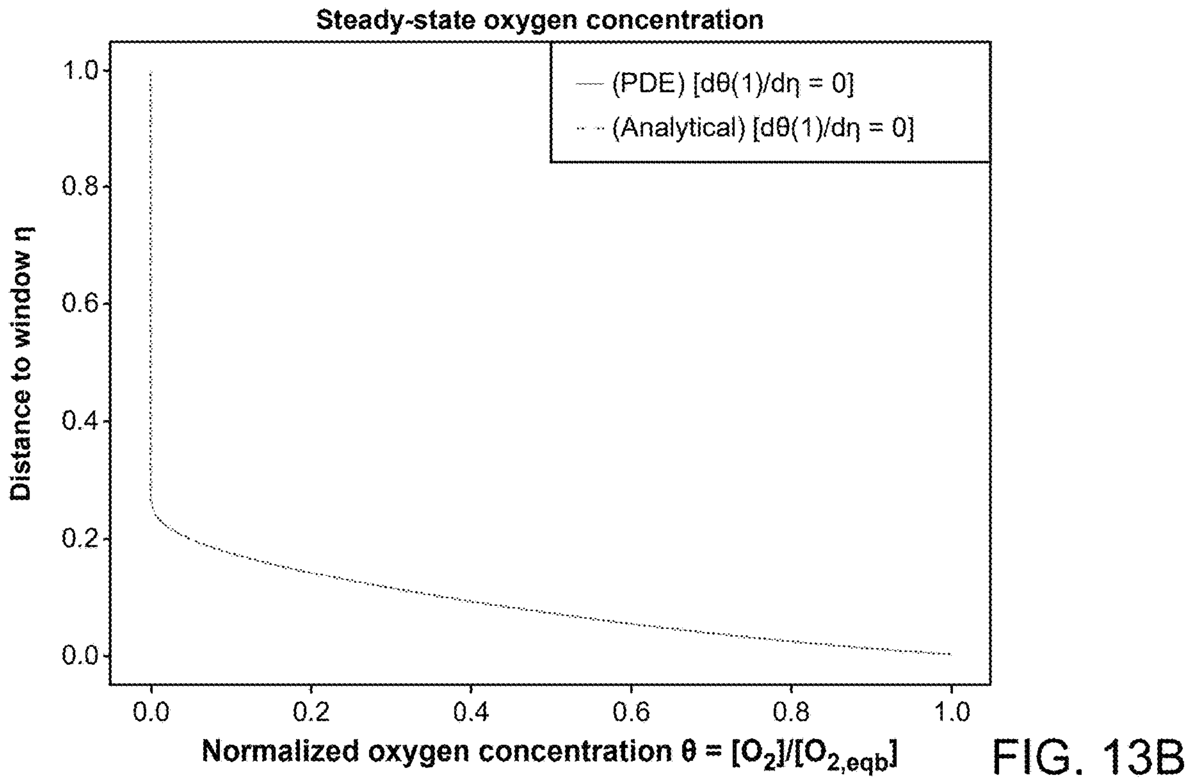
Figures 13C, 13D:
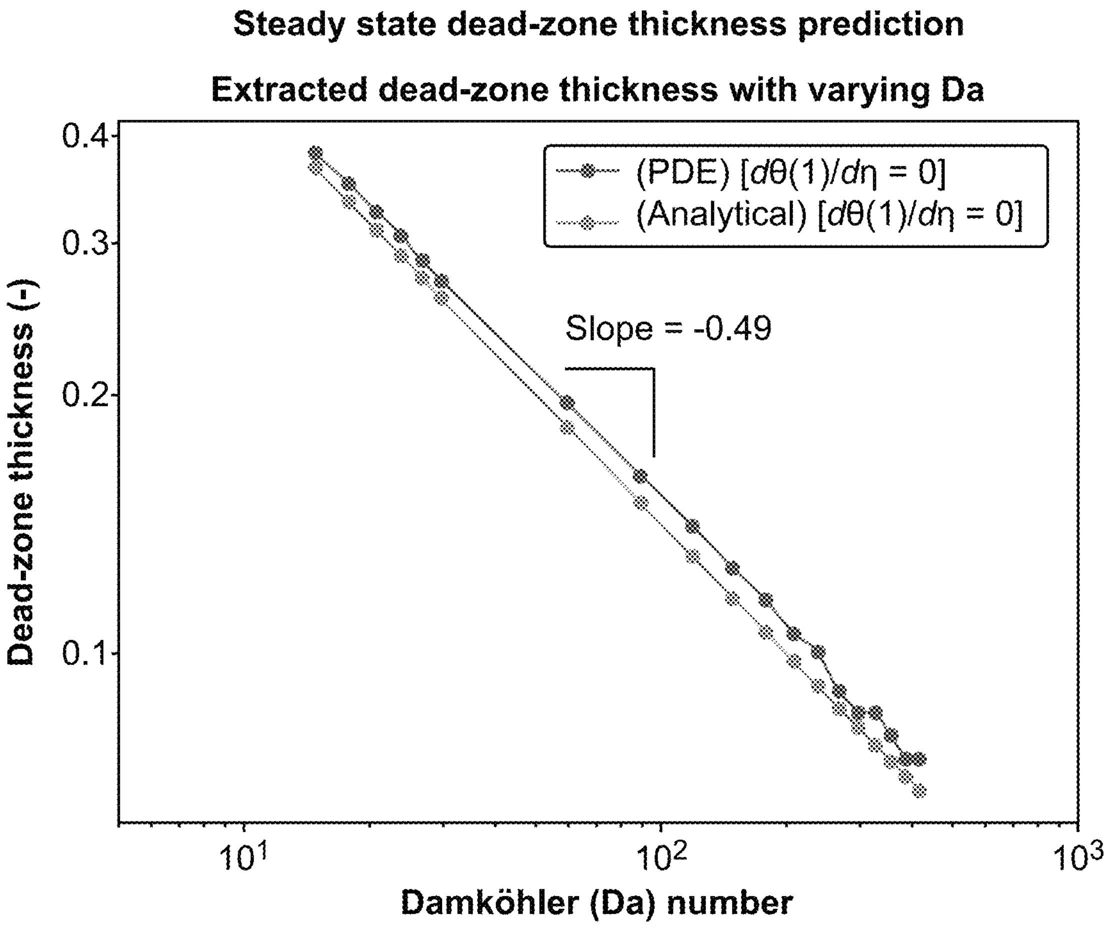

Solving both PDEs (Eqs. (9,10)) simultaneously using the parameters in (FIG. 13D), the numerical PDE solution of the transient oxygen concentration and unconverted oligomer concentration can be found in FIG. 13A(i-ii), and a snapshot of all active components within the dead-zone regime at t=0.1 (–) can be found in FIG. 13A(iii). Under the assumption that $\alpha$=290 $8.09\times10^{-7}$ is small (FIG. 13D), we can obtain the steady state solution, and an analytical expression for steady state oxygen concentration is derived and compared with the numerical solution (FIG. 13D). It is found the numerical steady state solution matches with the analytical solution, indicating that the steady state oxygen concentration profile is independent of the boundary conditions at the build platform. (FIG. 13).Assuming that the oxygen-concentration threshold for the dead-zone (or oxygen-inhibition zone) formation is 105, we can vary the parameter Dar involved in a CLIP printing process and estimate the corresponding dead-298 zone thickness under different values of $Da_1$. It is observed that the dead-zone thickness is approximately 3-5 μm from our model prediction and its thickness scales with the –0.5th power of the appropriate Damköhler number $$\left(Da=Da_1\frac{\alpha}{2}\right)$$

(FIG. 13C).

$$\text{Dead-zone thickness }(h)\propto\left(\frac{H^2\varphi\varepsilon[PI]I_0}{D_o[O_{2,eqb}]}\right)^{-0.5} \quad (11)$$

The Damköhler number is a measure of ratio of the rate of oxygen diffusion and the rate of kinetics (photopolymerization and oxygen depletion rate). We provide a justification for this scaling by calculating the steady value of the oxygen concentration (and hence the dead-zone thickness) below.

Analytical Solution for Oxygen Concentration Profile

To provide a deeper understanding of the oxygen concentration profile at steady state, we proceed to solve for an approximate steady state analytical solution. The dimensionless governing equation for steady state oxygen concentration is (from Eq. (9)):

$$\frac{d^2\theta}{d\eta^2}=Da_1\theta[-\theta+\sqrt{\theta^2+\alpha\exp(-\beta\eta)}, \quad (12)$$

But we note that both $\beta$ and $\alpha$ are small parameters. Due to the fact that $\beta$ is small, we can approximate (Eq. (12)) as:

$$\frac{d^2\theta}{d\eta^2}=Da_1\theta[-\theta+\sqrt{\theta^2+\alpha} \quad (13)$$

Now for small values of aa we can expand the term under the radical assuming a Taylor expansion and retain only the leading order term to obtain:

$$\frac{d^2\theta}{d\eta^2}\approx Da_1\frac{\alpha}{2} \quad (14)$$

This is accurate as long as $\theta>>(\sqrt{\alpha})$. However, if $\theta\sim O(\sqrt{\alpha})$ the right-hand side of Eq. 13 still represents a positive reaction sink of oxygen. Thus, we conclude that when Eq. 14 is no longer accurate, we enter a regime of approximately zero oxygen concentration. To define that region and connect it to the region of finite oxygen concentration, we apply the boundary conditions:

$$\theta(0)=1$$

$$\frac{d\theta(h)}{d\eta}=0$$

$$\theta(h)=10^{-5}\sim 0$$

where h denotes the end of the region of finite oxygen concentration. Note that the last two conditions are continuity of oxygen concentration and oxygen flux across the two regions. For values of $\eta>h$ (actually values of $\theta\sim O(\sqrt{\alpha})$) we thus assume that the value of $\theta$ is essentially zero.

Denoting $Da=Da_1\frac{\alpha}{2}$, we can then apply the above boundary conditions to solve for $\theta$ in the region of finite oxygen concentration, viz:

$$\theta=\frac{Da}{2}\eta^2+(-Dah\eta)+1, \tag{15}$$

and we can also solve for the value of (h) (which is the steady dead-zone thickness) by using the last condition:

$$\frac{Dah^2}{2}-Dah^2+1\sim 0 \tag{16}$$

Solving, we obtain:

$$h=\sqrt{\left(\frac{2}{Da}\right)} \tag{17}$$

This completes the solution, and we demonstrate in FIG. 13C that it is in excellent agreement with the numerical solution for the parameters appropriate to the printing conditions. Based on this analysis, an estimation of exposure time for resin to reach steady-state cure height in dead-zone thickness HH follows the expression:

$$t_{cure}=\frac{H^2}{D_o}\frac{2\alpha}{Da_1} \tag{18}$$

Overall, this study provides fundamental insights to CLIP printing process, including how the dead-zone thickness depends on the oxygen permeability of the window, the oxygen concentration at the window surface, the applied light intensity, and the photo-initiator concentration.

High-Resolution CLIP Optics and Kinetics Modeling: 3D Print Part Prediction

We combine our understanding of the photopolymerization model (Eqs. (4-17)) with the projection optics model (Eqs. (1-3)) to predict the final 3D printed structure. The photopolymerization model served as a prediction of the cured-height and the 2D projection optics model provided a prediction of the minimum lateral resolution achievable through optical design. To validate the performance of the model, we have designed a square pyramid microstructure and compared the height and surface finish between the 3D printed part from the single-digit-micro-resolution CLIP-based 3D printer and the simulated 3D printed object using the simulation model. The simulated results and the corresponding SEM images of the 3D printed structures 30 µm (FIG. 12B (i)) and 1.5 µm (FIG. 12B (ii)) CLIP printers are compared to provide a better understanding of how optical resolution can impact the surface finish. The same parameters were used for both the simulation and actual 3D print. The simulation was able to capture the final print height and the surface finish for both high-resolution CLIP printers. Importantly, the increase in lateral resolution from a 30-µm-resolution to a 1.5-µm-resolution CLIP resulted in a significantly improved surface finish.

High-Resolution CLIP Modeling: Mass Transport and Print Speed

The development of a predicted flow field during stage movement and an estimation of the force experienced between each print layer. We have modeled the inward flow field of the uncured resin into the gap between the build platform and the window using lubrication theory. While the "squeeze flow lubrication" for a power law fluid has been studied previously, for completeness we provide a derivation of the full velocity profile. Note that we have considered both Newtonian and non-Newtonian (power-law) fluids in determining the velocity flow profile and Stefan force in the dead-zone regime. It is worth mentioning that both of our resins show shear-thinning behavior (Rheometer data in FIG. 19) and are more accurately modeled as power-law fluids. Solving for the analytical velocity flow profile of the Newtonian fluid in the dead-zone regime, we obtain the following equations:

$$\tilde{V}_r=-\frac{U}{\varepsilon}r(z(h-z)) \tag{19}$$

$$\tilde{V}_z=-U(3z^2-2z^3) \tag{20}$$

where $\tilde{V}_r$ and $\tilde{V}_z$ are the dimensionless velocity fields in r and z directions, U is the dimensionless build platform travel velocity, r and z are the dimensionless coordinates in rand z, h is the dead-380 zone height, and $\varepsilon$ is the ratio of the dead-zone height to the radius of the print part (or build 381 platform) (L). Solving for the non-Newtonian (power law fluid) velocity flow profile in the dead-zone regime, we obtain the following for the fields:

$$\tilde{V}_r=\begin{cases}\left(\frac{1}{\varepsilon}\right)\left(\frac{Ur}{2\alpha}\right)\left(\frac{1-n}{2-n}\right)\left[\left(Z-\frac{h}{2}\right)^{\frac{2-n}{1-n}}-\left(\frac{h}{2}\right)^{\frac{2-n}{1-n}}\right] & z>\frac{h}{2}\\ \left(\frac{1}{\varepsilon}\right)\left(\frac{Ur}{2\alpha}\right)\left(\frac{1-n}{2-n}\right)\left[\left(\frac{h}{2}-Z\right)^{\frac{2-n}{1-n}}-\left(\frac{h}{2}\right)^{\frac{2-n}{1-n}}\right] & z<\frac{h}{2}\end{cases} \tag{21}$$

Figure 14A:
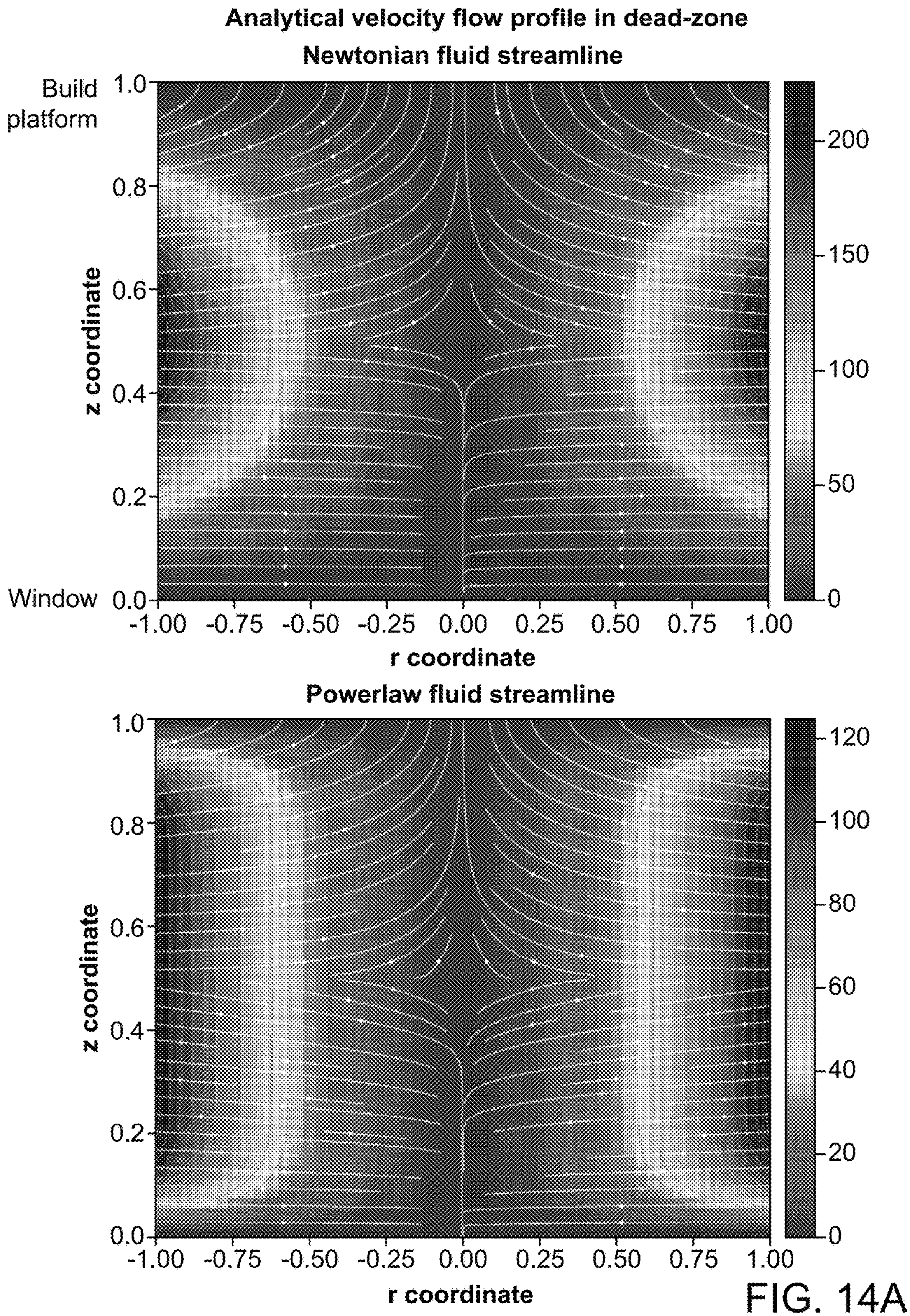
FIGS. 14A-14B depict mass transport modeling using lubrication theory for a CLIP printing process according to certain embodiments.

-continued $$\tilde{V}_z = \begin{cases} M(r)\left[\left(\frac{1-n}{3-2n}\right)\left(z-\frac{h}{2}\right)^{\frac{2-n}{1-n}} - \left(\frac{h}{2}\right)^{\frac{2-n}{1-n}}\left(z-\frac{h}{2}\right)\right. & z > \frac{h}{2} \\ \left. + \frac{U}{M(r)} - \left(\frac{n-2}{3-2n}\right)\left(\frac{h}{2}\right)^{\frac{3-2n}{1-n}}\right] & \\ M(r)\left[\left(\frac{1-n}{3-2n}\right)\left(z-\frac{h}{2}\right)^{\frac{3-2n}{1-n}} - \left(\frac{h}{2}\right)^{\frac{2-n}{1-n}}\left(\frac{h}{2}-z\right)\right. & z < \frac{h}{2} \\ \left. - \left(\frac{n-2}{3-2n}\right)\left(\frac{h}{2}\right)^{\frac{3-2n}{1-n}}\right] & \end{cases} \tag{22}$$

Where n is the shear-thinning power law exponent obtained from the flow sweep rheology, $$M(r) = -\left(\frac{1-n}{2-n}\right)\left(\left(\frac{1}{1-n}\right)\left(\frac{Ur}{2\alpha}\right)^n + \frac{Ur}{2\alpha}\right),\ \alpha = 2\left(\frac{1-n}{3-2n}\right)\left(\frac{h}{2}\right)^{\frac{3-2n}{1-n}},$$

and all the remaining parameters are the same as listed in the Newtonian section. The velocity profile in high-resolution CLIP for Newtonian fluid based on (Eqs. (19-20)) is shown in FIG. 14A(i) and non-Newtonian power-law fluid based on (Eqs. (21-22)) in FIG. 14A(ii).

As discussed in the section High Resolution 3D CLIP Printing Strategy, we have adopted a stepped printing process (move-stop-expose) to allow for resin replenishment and followed by a quiescent state prior to curing. It is therefore critical to understand the vertical force experienced during the moving step of each printing process. Based on lubrication theory, we calculated the Stefan force involved in each print steps. At present, we focus on the analytical expression and the experimental verification of the Stefan force.

Figure 14B:
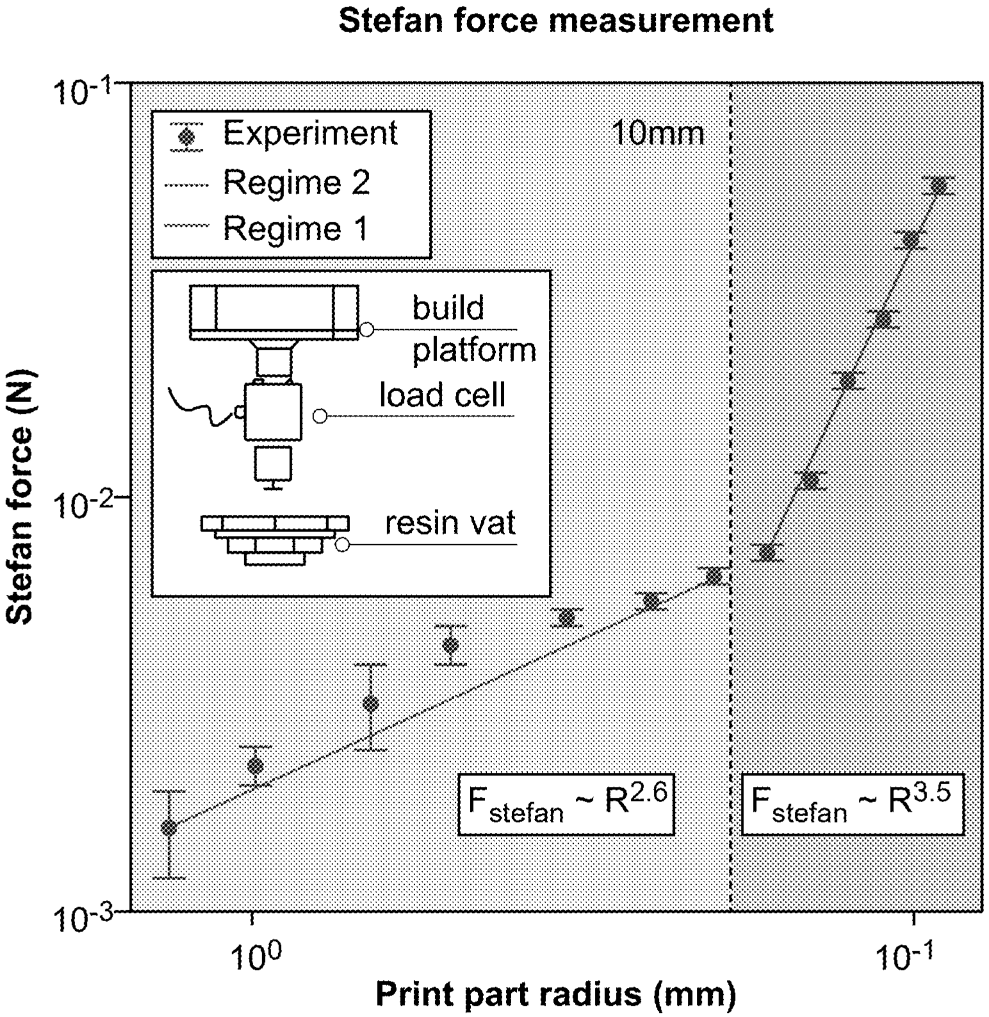

The dimensional Stefan force for both Newtonian and power law fluids are:

$$F_{Stefan} = \begin{cases} -\frac{3\pi\mu U}{2h^3}R^4 & \text{Newtonian} \\ -\frac{\mu_0}{4-n}\left(\frac{U}{2\alpha}\right)R^{4-n} & \text{non-Newtonian} \end{cases} \tag{23 and 24}$$

where $\mu$ is the viscosity for the Newtonian fluid and $\mu_0$ is the zero-shear viscosity coefficient for the non-Newtonian fluid (Cf. (Eq. (16))). We verify the applicability of lubrication theory on the high-resolution 3D CLIP printer system through directly measuring the force experienced FIG. 14B. The power-law dependency of the Stefan force with 405 print part radius is observed to be 3.5 when the print part radius is greater than 1.2 cm. When the print part radius drops below 1 cm, the power law dependencies of 4-n predicted by lubrication theory ceases to hold, and we observe a power scaling of <1. This indicates the inapplicability of simple lubrication theory when print part radius below 1 cm even though this is still many times the dead-zone thickness (Estimation of dead-zone thickness is approximately 3-5 μm in High-resolution CLIP modeling: Photopolymerization gradient study section).

Figure 19A:
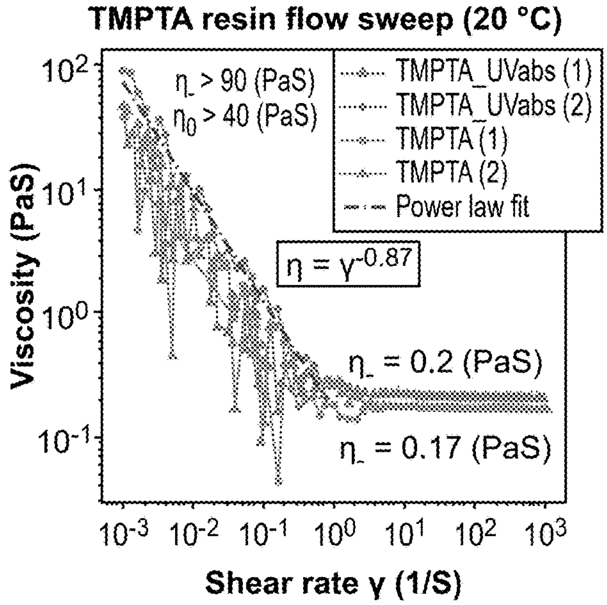
FIGS. 19A-19C depict flow sweep and stress relaxation characterization done on two resins: EPU 40 and TMPTA resin according to certain embodiments.
Figure 19B:
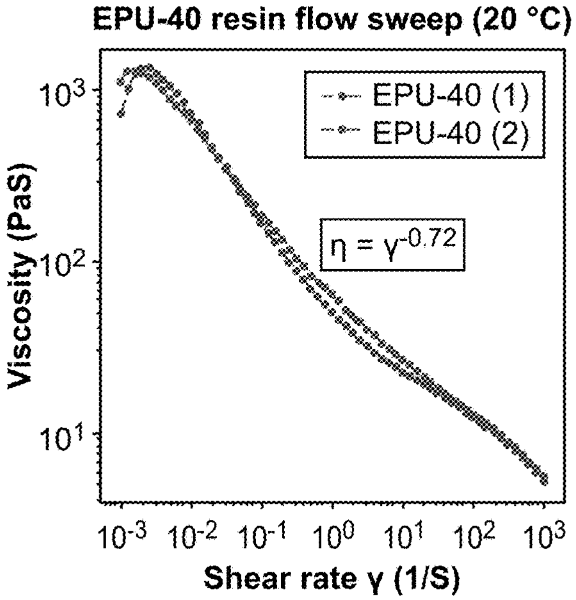
Figure 19C:
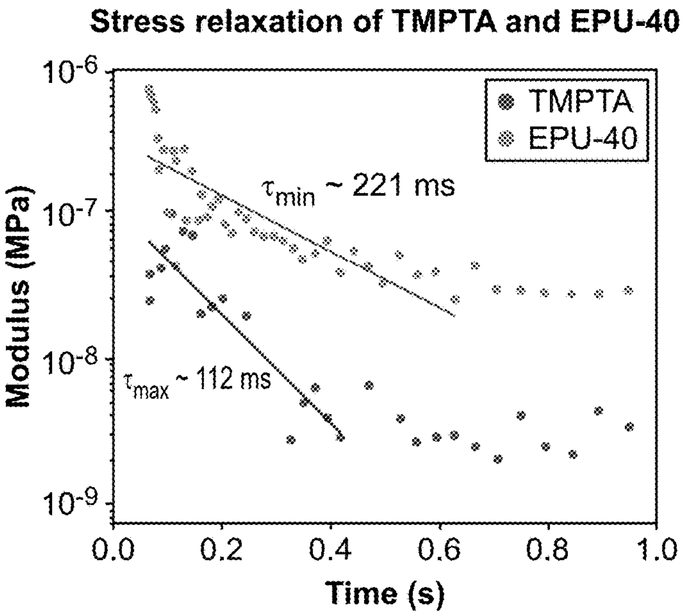
Figure 20A:
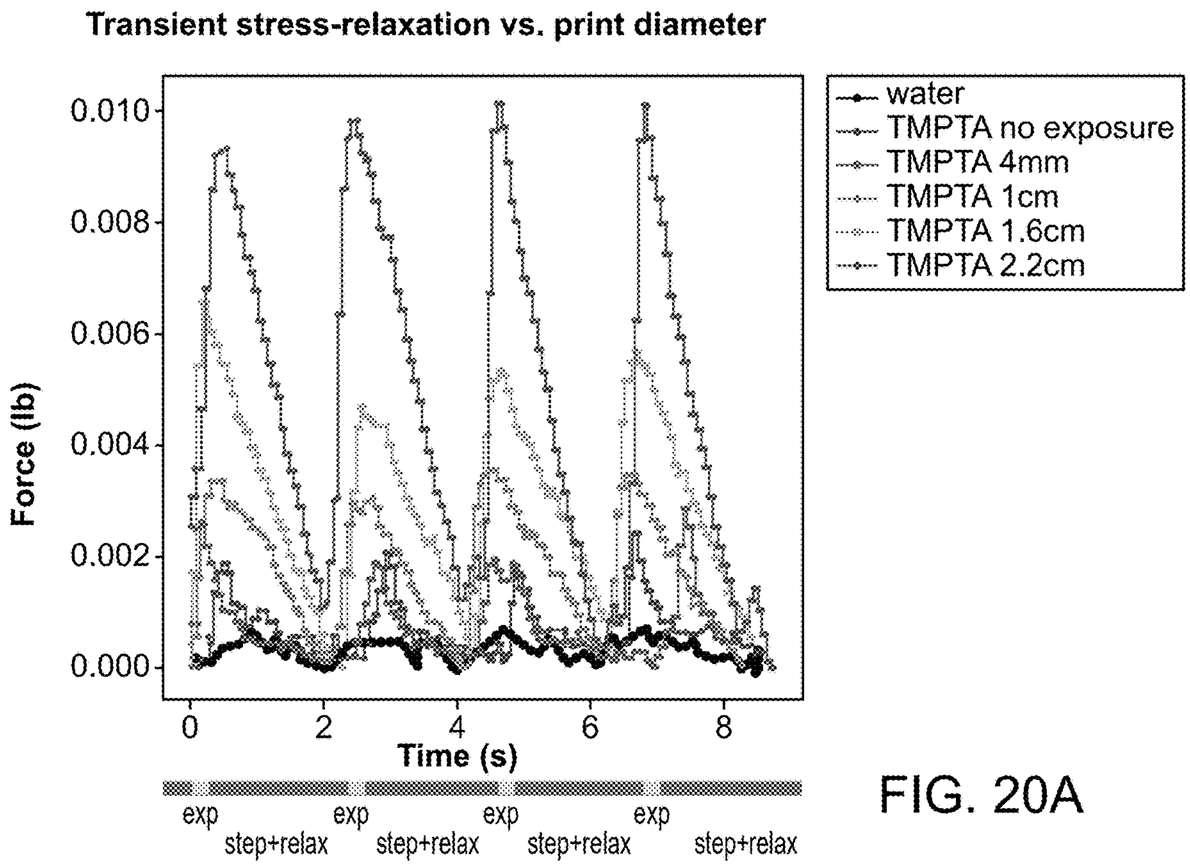
FIGS. 20A-20B depict the stress-relaxation time for different print diameter according to certain embodiments.
Figure 20B:
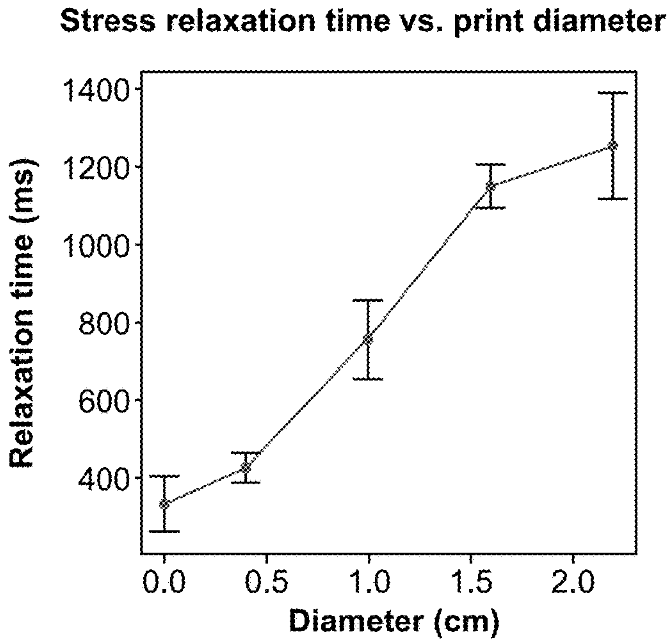

It has been noticed that if the interlayer time is insufficient for the resin reflow, several print artifacts are expected, such as, shorter print height, deformation of print pattern due to liquid flow during incomplete photopolymerization, and surface roughness. For Newtonian fluid, the critical time scale for resin to replenish the vacuum region at the deepest pixel location follows $$\frac{h^2}{v}$$

and is nearly instantaneous ~10-6 ms, where h is the dead-zone thickness and vis the kinematic viscosity. For non-Newtonian resin however, the critical time scale is determined by the stress-relaxation time that is related to the % strain the resin experienced, the evolution of material properties during photopolymerization, and print diameter. Characterizations on resin stress-relaxation time before (FIG. 19) and during printing processes (FIG. 20). It is observed that to print a structure of 4-5 mm diameter, the relaxation time measured by force sensor measurements is found to be around ~300-400 ms, and insufficient stress-relaxation time (<200 ms) for resin relaxation and reflow will lead to decrease in print resolution (FIG. 21).

High-Resolution CLIP Print Demonstration

Figure 15:
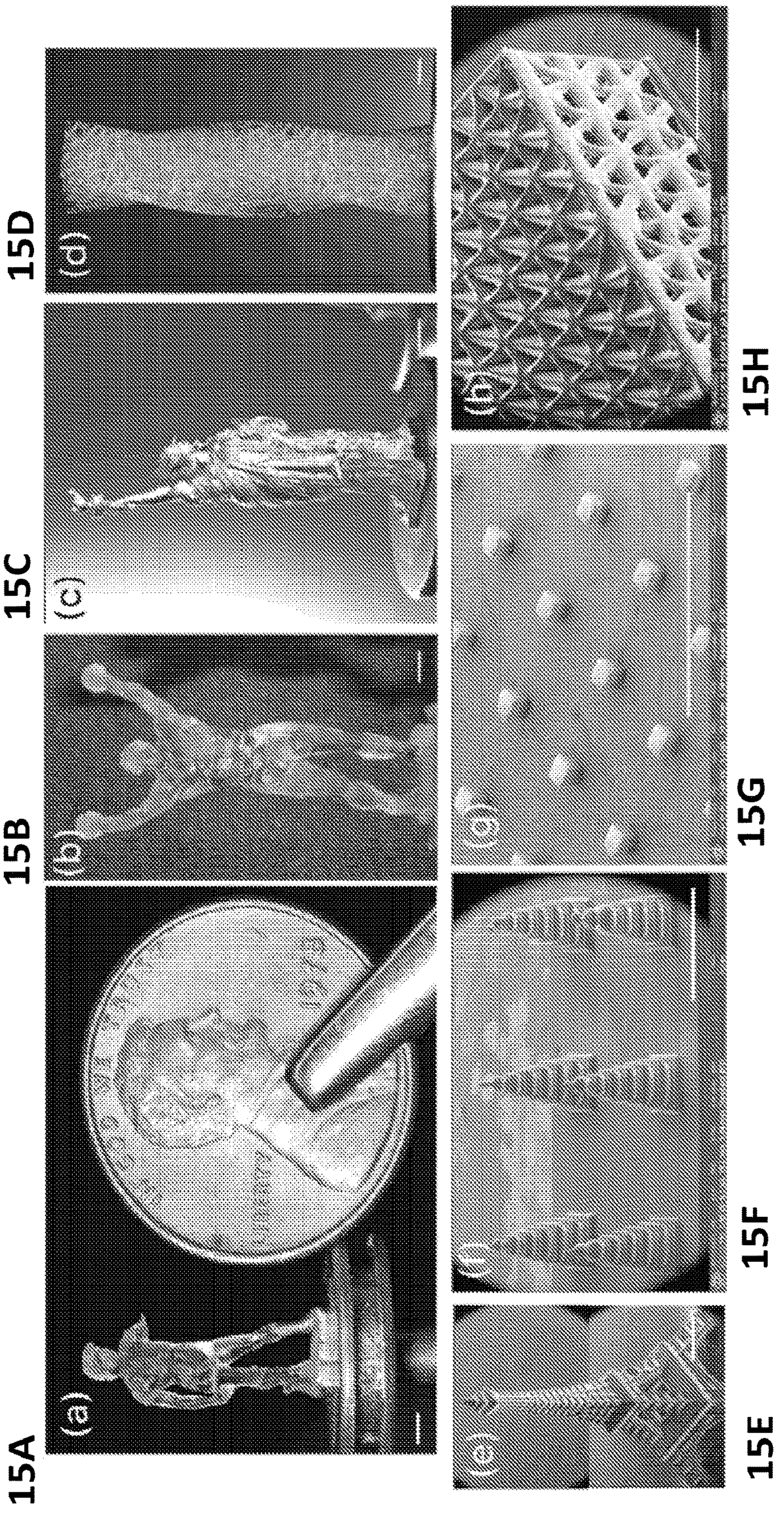
FIGS. 15A-15H depict Demonstration prints from the single-digit-micron-resolution CLIP-based 3D printer.

To demonstrate the capability of our single-digit-micron-resolution CLIP-based 3D printer to print intricate, miniature 3D models with a fast speed and high surface smoothness, we explored multiple CAD designs and printed them with various materials. We have explored making 3D structures having a minimum feature size of micrometer length scale (FIG. 15A-15C)), a twisted lattice structure of 1.25 cm height with 100 μm strut thickness (FIG. 15D), and α micro-Eiffel tower structure 3 mm in height with minimum strut thickness at 50 μm (FIG. 15C). We have also explored structures with engineering and biomedical utility, such as a terraced microneedle design (FIG. 15F), and α square block array (FIG. 15G). All parts in FIGS. 15A-15G were printed using a resin formulation of TMPTA+0.3 wt % BLS1326+2.5 wt % TPO and have a viscosity of 0.2 Pa·S. We have also printed a lattice block with a viscous elastomeric material (EPU-40), with a viscosity 20 Pa·S (FIG. 15H). As discussed in High-resolution CLIP modeling: mass transport and print speed section, it is important to note that the corresponding printing parameters, specifically the interlayer time, is quite different for materials with different viscoelastic properties. The total printing time depends on the height (in z) of the design and the viscoelastic properties of the material selected. For example, parts that were printed with a low viscosity resin, such as microneedle designs or micro square blocks (FIGS. 15F and 15G), took 3 minutes to complete. Moreover, the tallest print (2 cm) of a lattice twisted bar design printed with a low viscosity resin (FIG. 15D) took 90 minutes. In comparison, a short (2 mm) lattice block printed with a viscous elastomeric resin (FIG. 15H) also took 90 minutes to complete the print. The increased viscosity of EPU 40 resin and stronger non-Newtonian fluid property indicate that it experiences stronger Stefan adhesion force and requires longer interlayer stress-relaxation time during print process. This experimentally validates the simulation model regarding the significant role of the resin viscosity (Eq. (23-24)), and the corresponding Stefan force and resin relaxation time in determining the print speed. (Detailed discussion can be found in Print speed and its role in scalability of high-resolution 3D printing technology in the Discussion section).

Figure 16A:
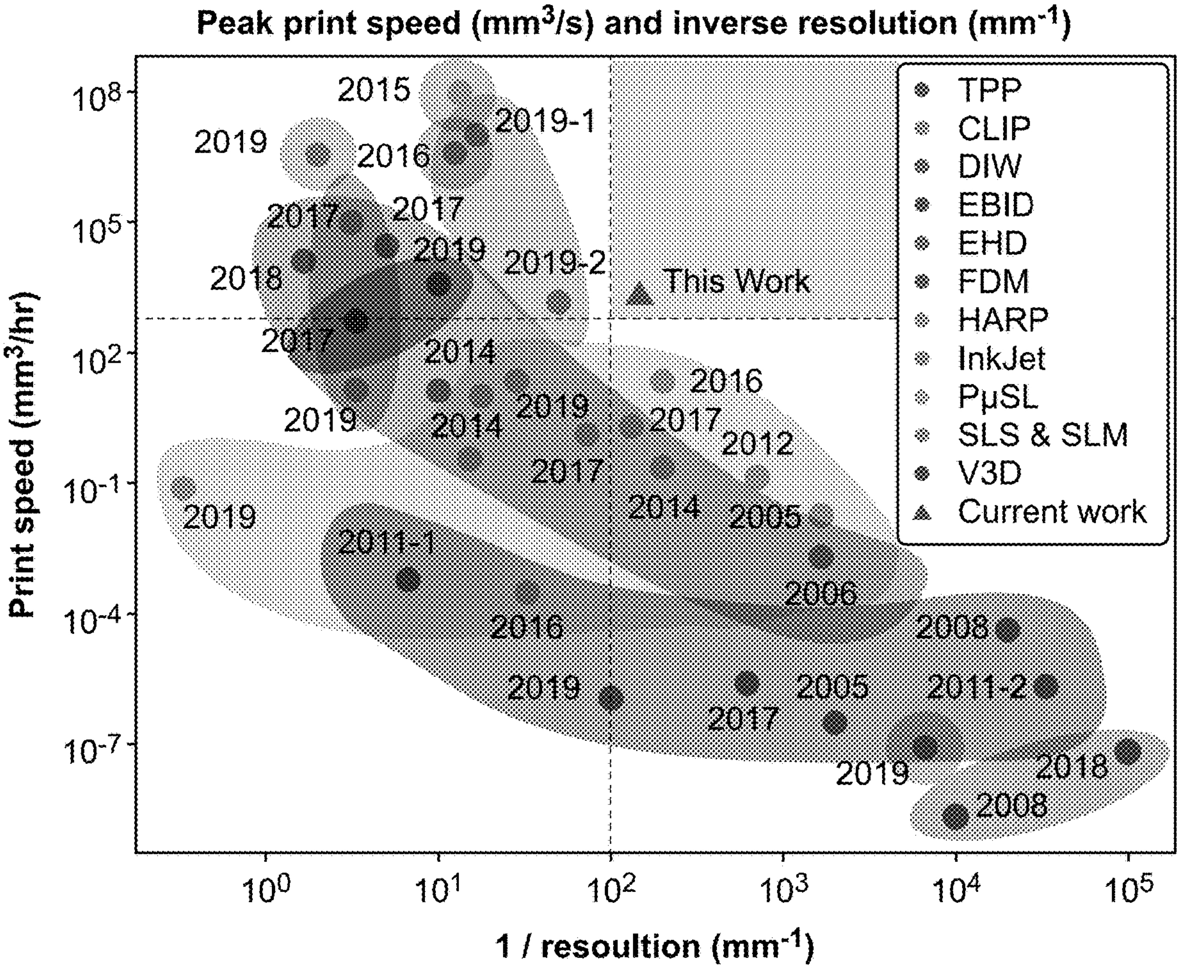

Single-Digit-Micron-Resolution and High Print Speed Achieved with High-Resolution CLIP 3D Printing Technology Among current high-resolution 3D printing technologies, it is generally difficult to achieve a high printing resolution while maintaining a high-print speed. Nanometer scale or micron scale patterning of has been achieved with technologies such as Electron Beam Induced Deposition (EBID), Electrohydrodynamic (EHD) jet printing, DIW, TPP, and micro-stereolithography (PμSL), however their print speeds are slow in comparison to IJ, Selective Laser Sintering (SLS & SLM), HARP, and CLIP printing technologies, resulting in lower throughput and scalability. Volumetric 3D printing (V3D) can achieve faster print speed than TPP but current geometries and resolution are still limited. In comparison to other high-resolution 3D printers, single-digit-micron-resolution CLIP-based 3D printer described herein provides a technological platform with high print speed and excellent resolution (FIG. 16A).

Figure 16B:
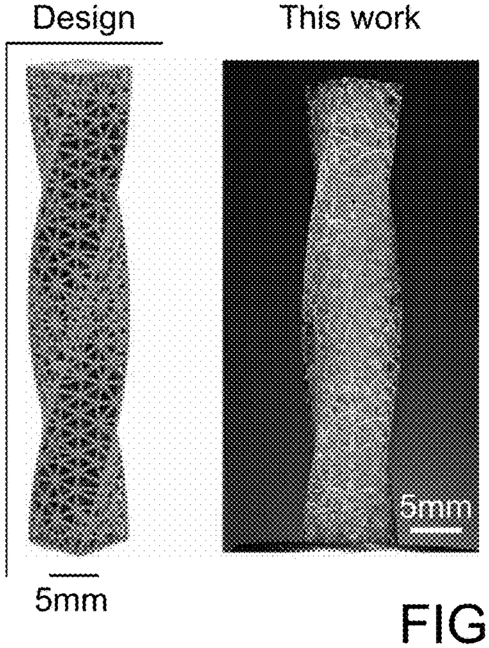

To provide a comparison in the practical usage of the newly developed single-digit-micron-resolution CLIP-based 3D printer and the commercial TPP printer (NanoScribe Photonics GT, NanoScribe, Germany), we have designed and printed a twisted lattice bar structure (2 cm in height with minimum strut thickness of 100 μm) and compared the total print time and quality. Although TPP is mainly used for nanometer length scale prints, since there are no other commercially available single-digit-micron-resolution 3D printers available, we have thus selected NanoScribe Photonics GT as a baseline for comparison. While the single-digit-micron-resolution CLIP-based 3D printer took 1.5 hour to completely print the 2 cm height design, TPP took more than 48 hours to print only 200 μm (FIG. 16B). The ratio of the print times is strikingly around 105 time shorter, highlighting the print speed and ultimate scalability of single-digit-micron-resolution CLIP.

2D patterns including lines and holes were designed to characterize and understand the high-resolution printability of our single-digit-micron-resolution CLIP-based 3D printer. Sample SEM images and geometric analyses of the print patterns are presented in FIG. 16C. The designed length scales of tested line patterns range from 135 μm to 4.5 μm (90 pixels to 3 pixels). It is observed that the print accuracy of the line patterns is optimal at length scales at or above 6 μm (4 pixels), with the dimension precision degrading below this value. As can be observed in the insets of FIG. 16C, the printed lines resolve cleanly for both 30 μm and 15 μm structures and the border becomes less sharp for 7.5 μm structures, corroborating with the larger standard deviation in print widths. Analysis of μm/pixel also showed reductions from our designed projection optics nominal resolution of 1.5 μm/pixel to 1.12 μm/pixel, indicating that the current limit to resolve line patterns is at 6 μm (FIGS. 16C and 16D). The designed length scale of tested hole patterns ranges from 45 μm to 18 μm (30 pixels to 12 pixels). It is observed that the print accuracy of the hole patterns is optimal at 22.5 μm and degrades at a smaller length scale as shown qualitatively and quantitatively in FIGS. 16C and 16D, respectively.

Discussion

Herein, we present a single-digit-micron-resolution CLIP-based 3D printer that has the capability to generate millimeter-scale 3D prints with single-digit-micron resolution in just a few minutes. For single-digit-micron resolution, we have designed and implemented a custom projection lens system that includes a tube lens and microscope objectives. Moreover, due to the extremely thin depth-of-field (tens of micrometers) of our high-magnification microscope objectives, we have incorporated a focusing algorithm with an in-line beam splitter and an adjustable tube lens that allows us to visualize the projection pattern with a CCD camera. We have utilized a digitally designed mesh pattern and have developed a contrast-based algorithm to search for the optimal focal plane position. After scanning through a depth of 400 μm and analyzing the through focus projected image stacks, we locate the maximum sharpness location and confirm the performance with actual print results. This contrast-based focusing system overcomes the challenge of focusing to the very thin depth-of-field from high-magnification projection optics and allows us to easily re-adjust to the optimal focal plane reproducibly.

The resolution performance of the single-digit-micron-resolution CLIP-based 3D printer was evaluated through line and hole patterns with the dimensions ranging from 4.5 μm to 13 5 μm. While our designed optical resolution is 1.5 μm, the smallest features that were successfully and repeatedly printed were 6 μm lines and 18 μm holes. It is observed that the printer resolution and print performance are strongly dependent on optical resolution, resin formulation, printing strategies, design patterns, and finally, cleaning strategies.

Next, we have developed a simulation model that seeks to provide a better understanding of CLIP printing process and guidance for developing the optimal printing strategies for various materials and designs. The model incorporates an optical simulation of projection optics via a point spread function (PSF) approximated with Gaussian distribution, a prediction of momentum transport and flow field using lubrication theory, and photopolymerization kinetics modeling to predict dead-zone thickness, oxygen concentration gradient, and cured-height. The model provides insights to improve the printing process, including adopting a printing strategy of stepped process (stop-move-expose) to allow for an efficient resin reflow, and an estimation of required interlayer time to eliminate resin convection-induced print artifacts. The model also provides an estimation of parameter values (light intensity, oxygen diffusion coefficient) required to maintain a steady dead-zone for continuous printing. Finally, we presented 3D print demonstration of our single-digit-micron-resolution CLIP-based 3D printers and the capability to print with viscous elastomeric material.

Achieving Automatic Focusing and its Role in High-Resolution 3D Printing Technologies Due to the shallow depth of focus of the highly magnified projection optics system in the single-digit-micron-resolution CLIP-based 3D printers and the micron-scale features that we are trying to resolve, a robust focusing mechanism to guarantee the print reproducibility and monitor the occurrence of any focus drift. Moreover, it has been observed experimentally that the focal plane of the projection optics at the surface of the dead-zone is strongly dependent on the window material, resin refractive index, and build platform reflectivity. Changing any material in between the path of the projection optics would require a whole new recalibration process. Currently, our method requires several steps of manual focusing, including (1) focusing the CCD camera on the build platform, (2) focusing the projection pattern onto the build-platform, and (3) obtaining through-focus image stacks to find the optimal z-location with the best focus performance. While this method has allowed us to achieve single-digit-micron resolution, much of the procedure still requires serial steps of manual focusing. It is thus desirable for the single-digit-micron-resolution CLIP-based 3D printer to have the capability to auto-focus. To achieve auto-focus in our current system, a real-time feed-back control of a camera imaging system along with a motorized translational z-stage actuator for the microscope objective should be designed and implemented. As 3D printing technologies venture into the single-digit-micron and nanometer length scales, and as auto-alignment and multi-layer 3D patterning becomes increasingly common, autofocusing systems have grown into one of the critical components for resolving small print parts.

Print Speed and its Role in Scalability of High-Resolution 3D Printing Technology For a long time, despite its many advantages, 3D printing technology was considered a non-scalable manufacturing process due to its limited applications in low-volume production with customized use cases. This was mainly due to the limited resolution and slow print speed of traditional 3D printers. The newly developed high-resolution and high-speed CLIP-based 3D printer introduced herein can resolve the main challenges that have been limiting the scalability of additive manufacturing. With 105 times faster print speeds than NanoScribe and 25-100 times faster print speeds than DLP and PμSL along with extraordinary resolution performance, the single-digit-micron-resolution CLIP-based 3D printer can achieve scalability in many ways that may ultimately elevate the additive manufacturing industry to a mainstream manufacturing process. These advantages have allowed it to start playing a significant role especially in biomedical and microelectronics applications, where creating millimeter length scale 3D objects with micro-meter patterning resolution within just a few minutes is highly desirable.

The current dependencies of print speed and resolution can be further explored. It is mentioned in High-resolution CLIP modeling of optics, momentum, and mass transport section that we have adopted a stepped printing process. The print speed is therefore determined by the interlayer time that includes: (1) exposure time and dark time. Dark time consists of: (2) stage travel time and (3) resin reflow time. Based on our kinetics simulation, the exposure time required for our z-resolution 0.5 μm is around 1 ms, the stage travel time at stage speed of 1 mm/s and acceleration 1 mm/s2 is measured to be around 50 ms, and the resin stress-relaxation time during the printing process is measured to be in the range of 200-1000 ms, depending on the print diameter. It can be concluded that the major time-consuming step (aka. speed limiting step) is the resin stress-relaxation time in between each layer. While a simple scaling relation between print resolution and print speed is not yet attainable, an experimental measured stress-relaxation time and print diameter relation has been developed.

It is important to mention that the current print speed can be further enhanced. Methods to reduce the interlayer time include: (1) reducing or removing the vacuum pressure experienced at the deepest pixel regime or (2) increasing the dead-zone thickness. Based on Equation (11), considerations to increase the dead-zone thickness includes (3) increasing the oxygen diffusivity through the oxygen-permeable window or (4) increasing the oxygen concentration at the window surface. Aside from overcoming the limitation in mass-transport within the dead-zone regime, there are other potential methods for developing a complete automatic cycle of a 3D printing process. Streamlining the cleaning, collection, in-line inspection, and storage into a full cycle can help reduce the waiting time and lead to faster turn-around times. The in-line inspection specifically can be bundled with the high-resolution 3D CLIP model development to create a machine-learning algorithm that adjusts the printing parameters to achieve the optimal printing accuracy and minimize print defects.

Print Area and its Implication for High-Resolution 3D Printer

One of the trade-offs of UV projection-based vat photopolymerization (e.g., DLP and CLIP) is that as the resolution improves, the overall print area reduces proportionally to the pixel size. For example, for a light engine that has a 2560×1600 array of pixels (>4M pixels), reduction optics method can be applied to modify the pixel size for the user's selected resolution from a few μm to hundreds of μm, so that the corresponding area will be in the range from 5 $mm^2$ to 500 $cm^2$. There resolution printers. One can implement an xy-translational stage that moves the vat by a certain distance to add multiple projections in one layer, similar to the stepper-motion introduced in the field of lithography. Although the overall print area while conserving the high resolution, the 605 overall manufacturing process is slowed down by either the translation stage speed or the post-processing steps and could introduce additional alignment errors. Recent advances with scanning lens projection methods and introduction of lens array in PμSL have significantly increase the build area and scalability.

Achieving 1.5 μm Resolution in Single-Digit-Micro-Resolution CLIP-Based 3D Printer The difference in theoretical resolution and actual print resolution in x, y, and z is critical to understand our system's limitation. The theoretical minimum resolvable distance d in x, y resolution in our 5× objective system, according to from Abbe diffraction limit, is $$\frac{\lambda}{2NA} \sim 1.4\ \mu m$$

Figure 12A:
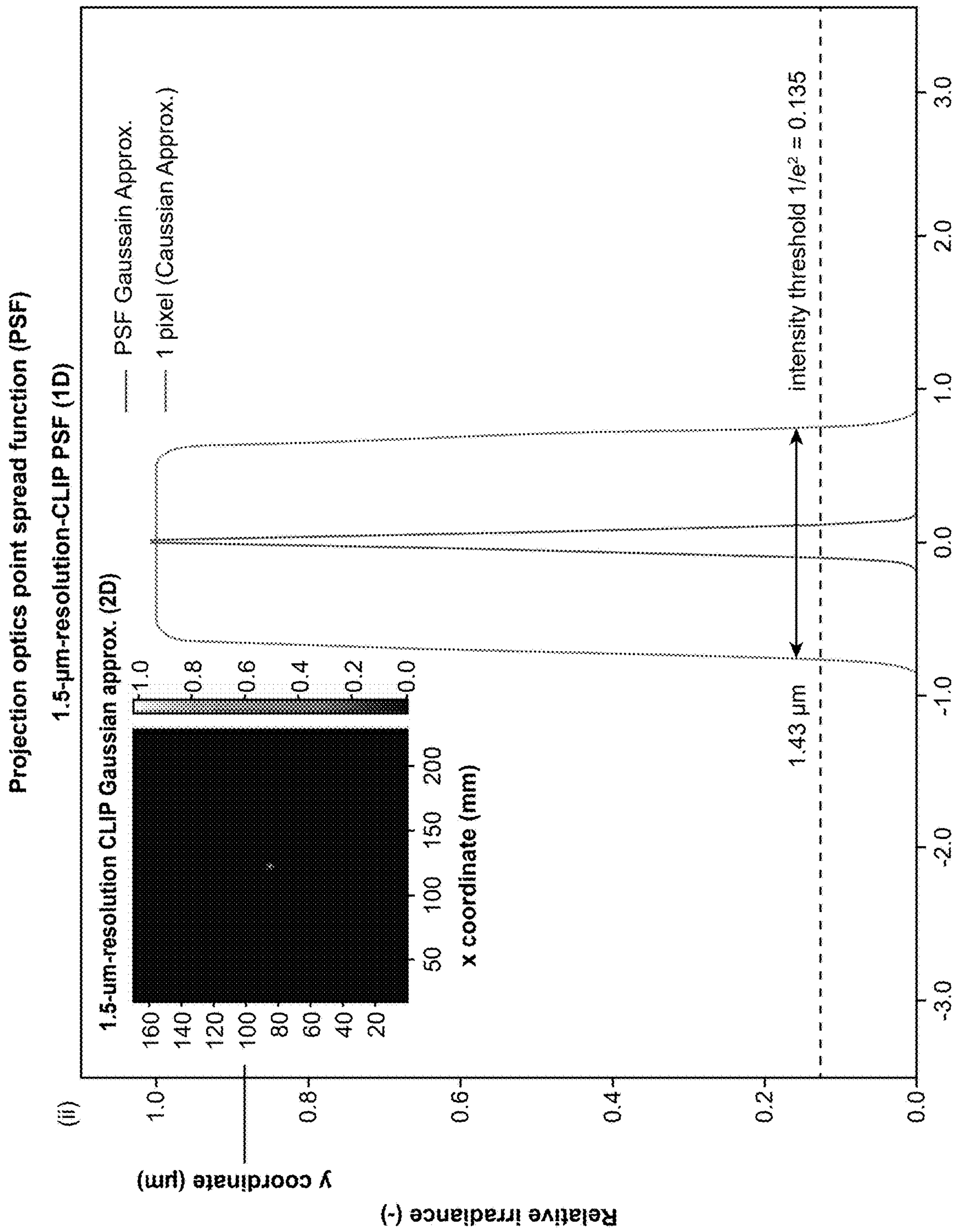
Figure 12B:
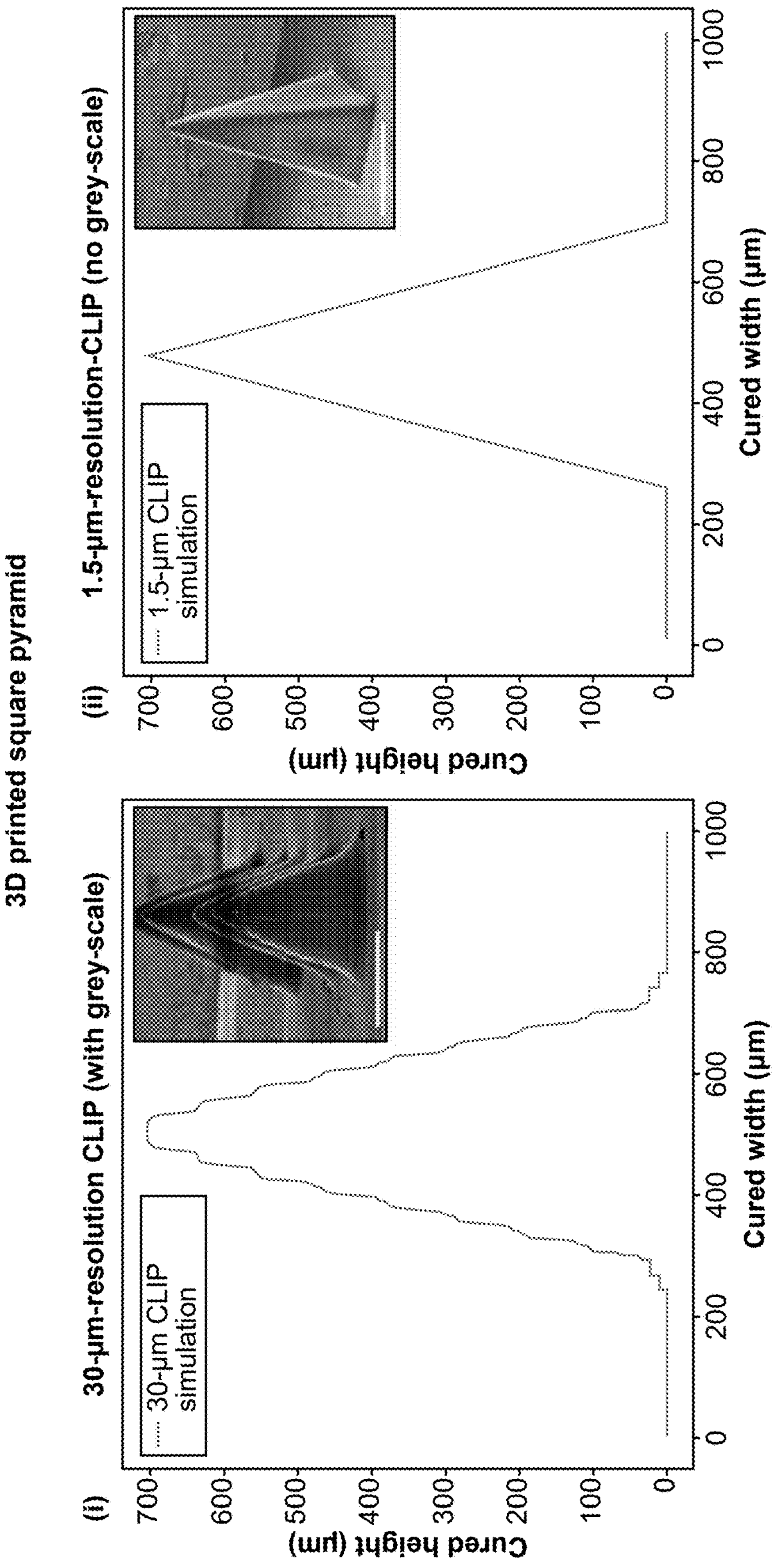
Figure 16B:
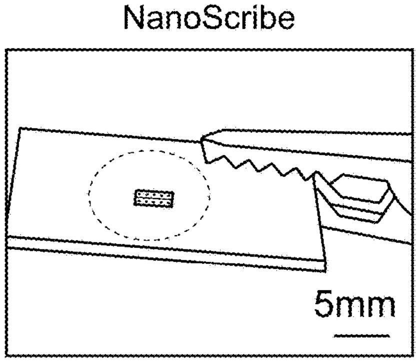

(FIG. 12). However, the current achievable minimum x, y resolution is around 6 μmm (FIG. 16). While our current model has only taken into account the light penetration distance in Beer's law (Eq. (4)), we believe the impact of resin formulation, reaction-diffusion termination kinetics and light scattering of cured parts all play a significant role in x, y print resolution. The minimum radical diffusion length scale LL can be used as an estimation of minimum x, y resolution. Previous studies have shown that termination reaction coefficient and radical diffusion coefficient is viscosity dependent, and we can estimate the diffusion coefficient to slow down based on degree of conversion and increase in resin viscosity. From pre-existing measurements, the estimated radical diffusion coefficient $D \sim 10^{-9}$ $m^2/s$ (roughly 1-2 orders of magnitude increase post photocuring), and taking the diffusion length scale to be $L=2\sqrt{Dt}$, radical life time to be t ~ 10-20 ms. the minimum resolution can be estimated to be around 4.5-6.3 μm, which corroborates with our current observations (FIG. 16). Our current modeling hasn't accounted for reaction-diffusion termination kinetics and light scattering, and future studies on Fourier Transform Infrared Spectroscopy (FTIR) and photorheology will be beneficial to understand the resolution limitation. The z resolution in our current system on the other hand, is only limited by the minimum stage travel distance 0.1 μm. The prediction of steady state dead-zone thickness from our kinetics model post initial exposure is ~3 μm. The dead-zone thickness governs the border of photopolymerization reactions and the cured height and z resolution in each layer is determined by the stage step size Ah post the initial exposure.

Supplemental

Figure 17A:
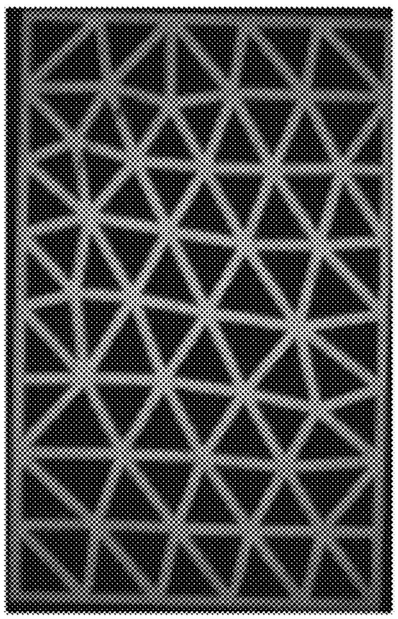
FIGS. 17A-17D depict detail on mesh design line edge profiles extraction for through focus contrast-based sharpness analysis according to certain embodiments.
Figure 17B:
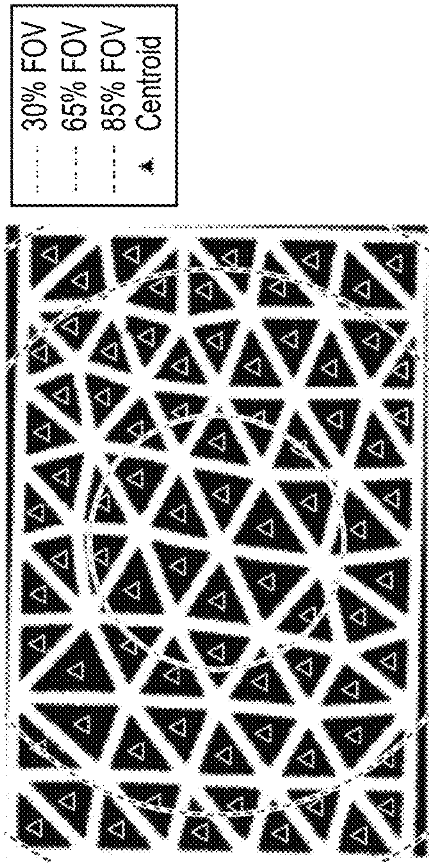
Figure 17C:
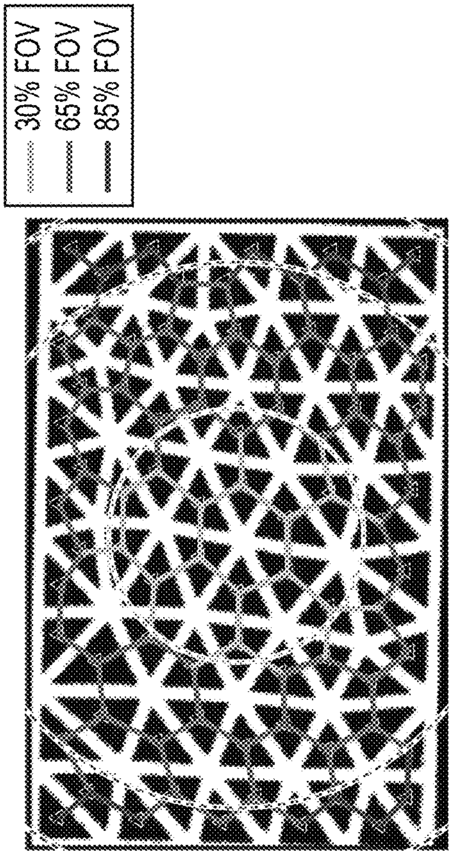
Figure 17D:
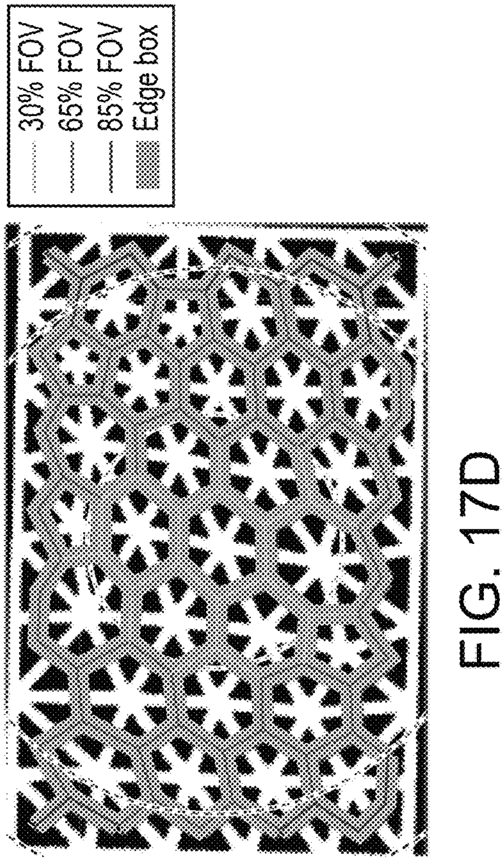
Figure 18A:
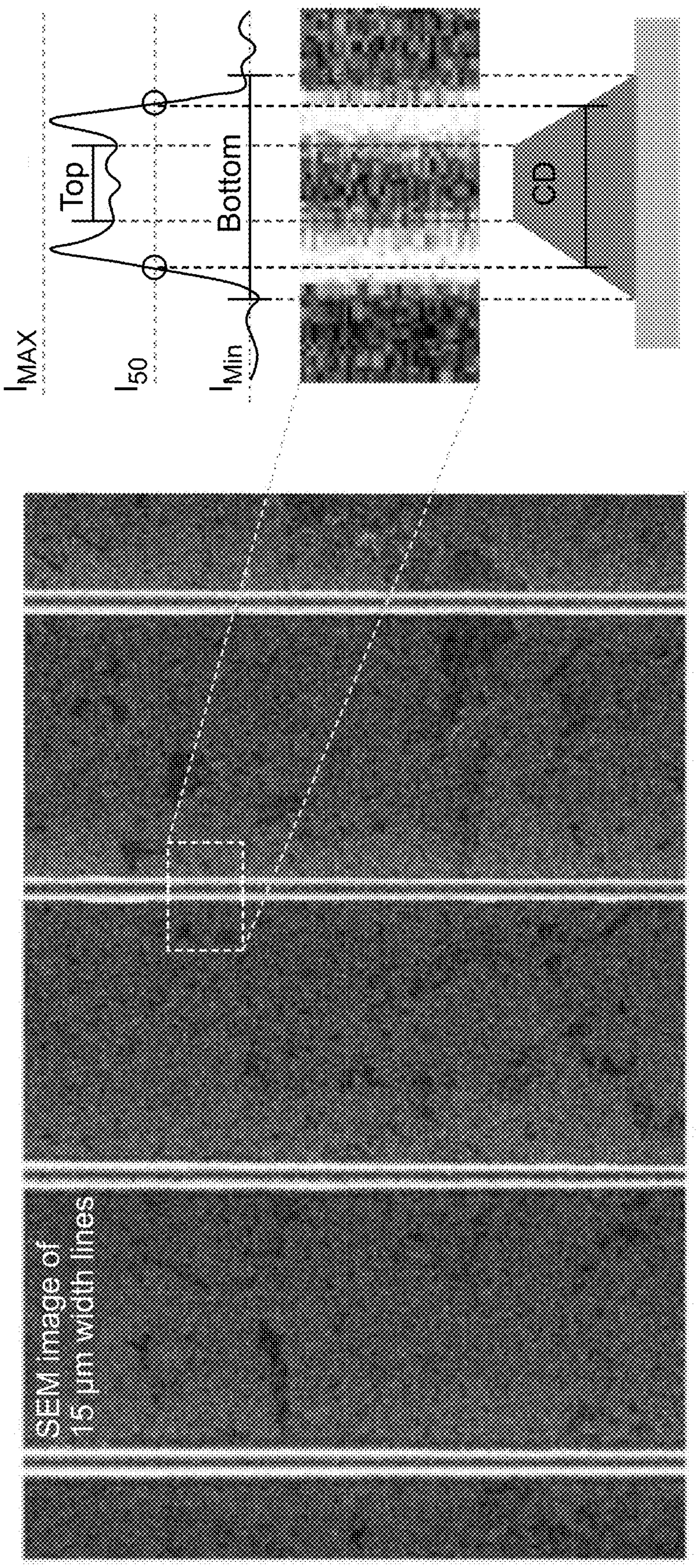
FIGS. 18A-18D depict details on extraction of feature sizes from line edge profiles in SEM images according to certain embodiments.
Figure 18B:
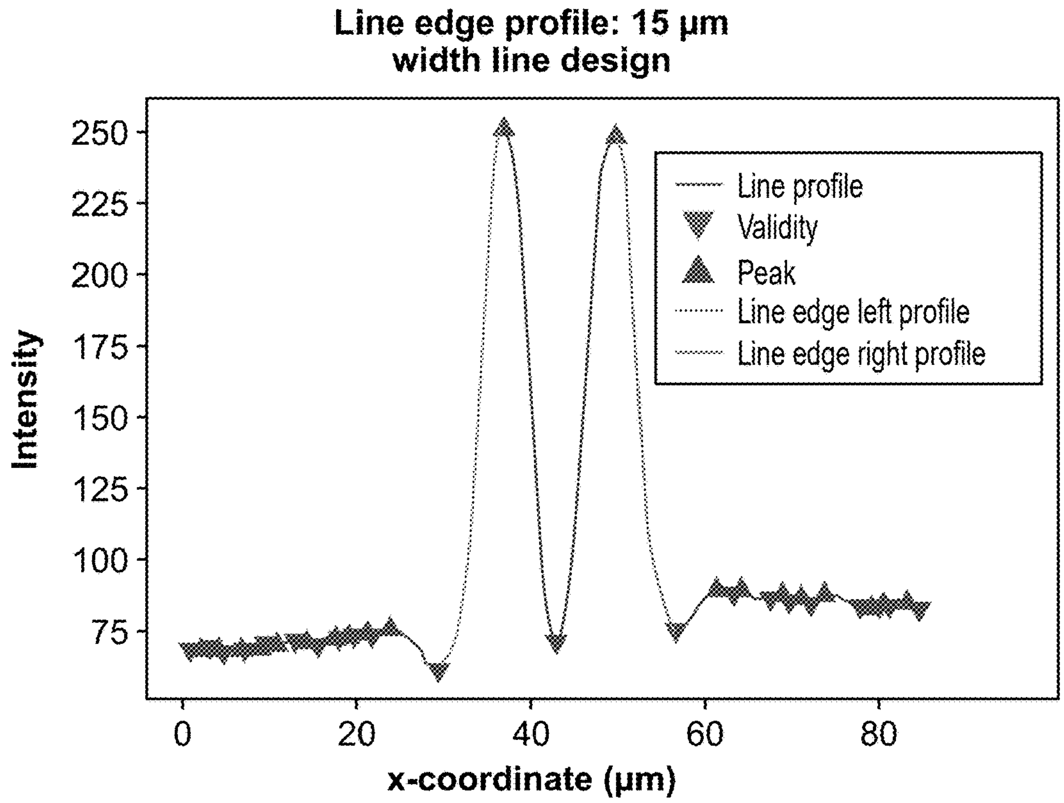
Figure 18C:
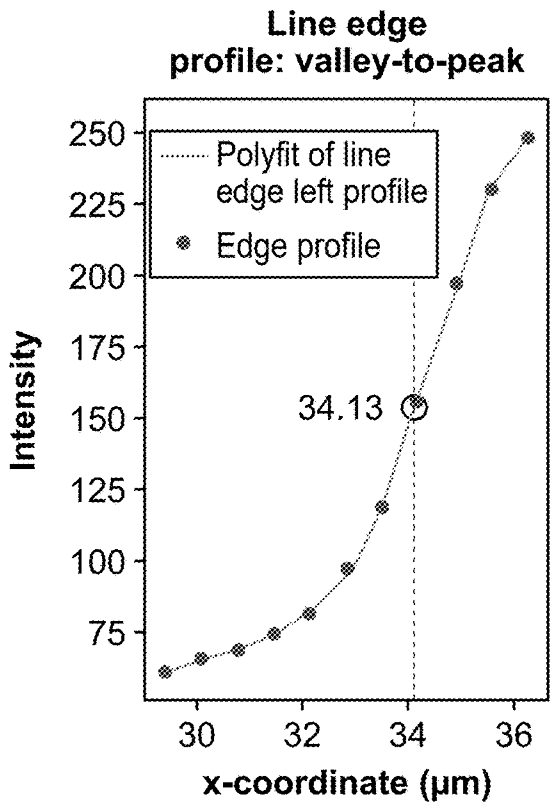
Figure 18D:
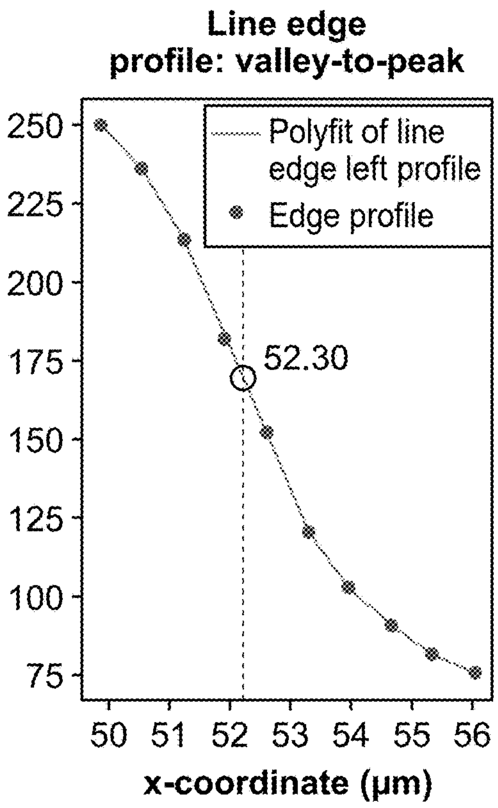

Contrast-based focusing algorithm for searching the optimal focal plane An image sharpness assessment algorithm is developed to extract the edge profiles within the full field of view (FOV) to obtain the full FOV sharpness analysis. A mesh design is selected for spatial resolution characterization (FIG. 17A). Feature detection and centroid extraction are applied for finding all triangular elements within the projected image (FIG. 17B). Distances are then calculated for each centroid, and they are further characterized based on their distance relative to the image center, ranging from 30% FOV, 65% FOV, and 85% FOV. Nearest adjacent neighbor calculation is conducted for each centroid to obtain the line pair for edge profile extraction. The edge profile extraction line segments are color-coded by their respective FOV (FIG. 17C). Finally, an average box for each line segment with 10 pixels away from the center of the line segment is calculated and plotted (FIG. 17D). This allows us to obtain the average edge profile for each edge. The obtained edge profile is thus the edge spread function (ESF) required for line spread function (LSF) and modulation transfer function (MTF) for image sharpness through focus.

Image Analysis Scheme for Extracting 2D Printed Feature from SEM Images

An image analysis scheme is applied to extract the line width from the SEM images. Shown here is a sample line edge profile extracted from a 15 μm width line design obtained from SEM. The SEM images are first imported into ImageJ and α single line or hole edge profile is extracted (FIGS. 18A-18D). The edge profile is then subjected to a simple algorithm through peak and valley extraction. The critical dimension (CD) extracted from the SEM is based on the 50% intensity threshold method, where the line width reported is based on the x-coordinates extracted at the 50% intensity threshold at the outer edge.

Model Parameters Used in the Transport and Kinetics Model

The final solution of the coupled partial differential equations (PDEs) for both the un-reacted monomer concentration and the oxygen concentration is obtained through MATLAB PDE solver and the parameters used can be found in FIGS. 13A-13D. While some parameters are directly obtained through references, there are also values that were estimated or directly measured. We provide a brief discussion of the estimated parameters.

The initial exposure time for resin to cure onto the build platform is roughly around 3s experimentally, depending on the design. Therefore, this gives us a rough estimation of H which should be around 10 μm, given that 3s is sufficient for print part to adhere onto the build platform for continuous print to proceed.

A rough estimation from the intensity that was configured for the 30 μm lens. The intensity/is obtained using the approximation of the known maximum intensity of our light engine for a 30 μm printer, which is around 40 $mW/cm^2$. The current value is assumed to linearly scaled by the related Lightcrafter 0-255 control. Nonlinearities in the LED itself as well as temperature fluctuations in the final light intensity have not been considered. To obtain the rough estimation of the light intensity, we took account for the single pixel projected area reduction (30 μm: 30; 3.5 μm: 3.75; 1.5 μm: 1.5) along with f #differences (30 μm: 1.3; 3.5 μm: 12; 1.5 μm: 16). With the listed details, we estimated the initial exposure at UV intensity 1 is 1.1 $W/m^2$ for 3.5 μm lens and 4 for 1.5 μm lens.

The [PI] concentration is obtained from known photoinitiator concentration 2.5 wt % that is used in our system.

The oxygen concentration at the surface of the window is estimated to be 3 times the concentration of a PDMS surface, due to the fact that a Teflon AF 2400 has 3 times higher permeability to oxygen than PDMS. Further experimental validation of the modeling parameters is crucial for a more accurate prediction. We also note that several key elements of oxygen transport are currently ignored, including the solubility of oxygen in the TMPTA resin as well as the permeability of oxygen through the Teflon AF 2400 window. We use model parameters obtained from known references as a rational framework to understand the CLIP printing process and dead-zone formation.

Thus, we can calculate the critical dimensionless parameters: Dα1=7.34*107, Dα2=5.51*103, α=8.09*10-7, β=7.8*10-4. We can also obtain the rough estimation of steady state dead-zone thickness as approximately 3 μm given the parameters above.

Derivation of Lubrication Theory Applied to CLIP Technology-Newtonian Fluid

From the CLIP schematic in (FIG. 4), the derivation of the lubrication theory after applying the appropriate scaling $$\varepsilon \sim \frac{h}{L};\ \tilde{u}_z \sim \frac{u_z}{U};\ \tilde{u}_x \tilde{u}_y \sim \frac{U}{\varepsilon};\ x = \frac{x}{L};\ \tilde{y} = \frac{y}{L};\ \tilde{z} = \frac{z}{h}$$

and assuming ε<<1, we obtained the simplified governing equations for Newtonian fluid as follows:

Continuity equation:

$$\nabla_s \cdot u_r + \frac{\partial u_z}{\partial z} = 0 \tag{1}$$

Momentum equation:

$$\frac{\partial^2 u_r}{\partial z^2} - \nabla_s p = 0 \tag{2}$$

$$\frac{\partial p}{\partial z} = 0 \tag{3}$$

Where $\nabla_s$ is the gradient operator in the x-y plane, The corresponding boundary conditions for the velocity are $$u_z = u_s = 0, \text{ at } z = 0$$

$$u_z = u_z(h), \text{ at } z = h$$

and $u_z(h)$ is used to describe the velocity of the top plate. From (Eq. (3)), pressure is thus only a function of $p^{(0)}(x_s t)$. We can then integrate (Eq. (2)) and applied boundary conditions $$u_s = \nabla_s p\left(\frac{z^2}{2} - \frac{zh}{2}\right) \tag{4}$$

To solve for $u_s$, and determine p we integrate (Eq. (4)) from 0 to h:

$$\int_0^h (\nabla_s \cdot u_s)dz + u_z^{(0)} \Big|_0^h = 0 \tag{5}$$

Applying boundary conditions, we obtain $$\int_0^h (\nabla_s \cdot u_s)dz = -u_z(h) \tag{6}$$

From (Eq. (4)), we know $$\nabla_s \cdot u_s = \nabla_s^2 p\left(\frac{z^2}{2} - \frac{zh}{2}\right) + \nabla_s p \cdot \left(-\frac{z}{2}\nabla_s h\right) \tag{7}$$

Substituting into (Eq. (6)), we obtain $$u_z(h) = -\int_0^h \nabla_s \cdot u_s dz = \nabla_s^2 p\left(\frac{h^3}{12}\right) + \nabla_s p \cdot \left(\frac{h^2}{4}\nabla_s h\right) \tag{8}$$

Assuming gap thickness h is a constant, we obtain $$u_z(h) = \nabla_s^2 p\left(\frac{h^3}{12}\right) \tag{9}$$

We can further express $u_z$ as $$u_z = -\int_0^z \nabla_s \cdot u_s d\xi = -\int_0^z \nabla_s^2 p\left(\frac{\xi^2}{2} - \frac{\xi h}{2}\right)d\xi = -\int_0^z \frac{12}{h^3}u_z(h)\left(\frac{\xi^2}{2} - \frac{\xi h}{2}\right)d\xi \tag{10}$$

Therefore, $$u_z = \frac{6}{h^3}u_z(h)\left(\frac{z^2 h}{2} - \frac{z^3}{3}\right) \tag{11}$$

If we assume at surface of plate, both velocity and height are maximum and normalized to 1, we can thus set $u_z(h)=1$ and h=1, we can obtain the velocity profile in both x and z direction in the dead-zone regime as follows:

$$u_z = (3z^2 - 2z^3) \tag{12}$$

$$u_r = \frac{1}{\varepsilon}z(z-1) \tag{13}$$

We can solve for the pressure field within the dead-zone regime if we first assume the part footprint is instantaneously a cylinder and L is the radius of the cylinder. Moreover, we assume p=0,ř=1. Integrating (Eq. (9)) then gives:

$$P = \frac{12}{h^3}\left\{\frac{r^2-1}{4}\right\} \tag{14}$$

We can integrate the pressure within the circular build area to obtain the Stefan force:

$$F_{stefan}^{Newtonian} = \int_0^R \frac{12}{h^3}\left\{\frac{r^2-1}{4}\right\}2\pi r dr = -\frac{3\pi\mu U}{2h^3}R^4 \tag{15}$$

Derivation of Lubrication Theory Applied to CLIP Technology—Non-Newtonian Fluid

For a non-Newtonian power-law fluid we assume. Note that for Newtonian fluid, n=0

$$\tau_{rz} = \mu_0\left(\left|\frac{\partial u_r}{\partial z}\right|^{-n}\right)\left(\frac{\partial u_r}{\partial z}\right) \tag{16}$$

Continuity equation:

$$\nabla_s \cdot u_r + \frac{\partial u_z}{\partial z} = 0 \tag{17}$$

Momentum equation (assuming cylindrical footprint):

$$\tau_{rz} = \frac{dP}{dr}\left(z - \frac{h}{2}\right) \tag{18}$$

$$\frac{\partial p}{\partial z} = 0 \tag{19}$$

Using (Eq. (16)) and (Eq. (18)) we can obtain expression for $u_r$ at $$z > \frac{h}{2}:$$

$$\mu_0\left(\frac{\partial u_r}{\partial z}\right)^{1-n} = \frac{dP}{dr}\left(z - \frac{h}{2}\right) \tag{20}$$

Solving for $u_r$ with boundary condition $u_r(h)=0$, we obtain:

$$u_r(z) = \left(\frac{dP}{dr}\right)^{\frac{1}{1-n}}\left(\frac{1-n}{2-n}\right)\left[\left(z - \frac{h}{2}\right)^{\frac{2-n}{1-n}} - \left(\frac{h}{2}\right)^{\frac{2-n}{1-n}}\right] \tag{21}$$

By symmetry we can obtain $u_r$ at $$z < \frac{h}{2}:$$

$$u_r(z) = \left(\frac{dP}{dr}\right)^{\frac{1}{1-n}}\left(\frac{1-n}{2-n}\right)\left[\left(\frac{h}{2} - z\right)^{\frac{2-n}{1-n}} - \left(\frac{h}{2}\right)^{\frac{2-n}{1-n}}\right] \tag{22}$$

Next, we use the continuity equation to solve for $$\frac{dP}{dr}.$$

From the continuity equation (Eq. (17)) we obtain:

$$\frac{1}{2}\frac{\partial}{\partial r}(ru_r)+\frac{\partial u_z}{\partial z}=0 \tag{23}$$

We can integrate (Eq. (23)) from 0 to h in z to obtain:

$$\frac{1}{r}\frac{d}{dr}r\left[\int_0^h u_r dz\right]=-U \tag{24}$$

To get expression for $$\left[\int_0^h u_r dz\right],$$

we integrate $u_r$ from $$\frac{h}{2}$$

to h and get:

$$\int_{h/2}^h u_r dz=\frac{1}{\mu_0}\left(\frac{dP}{dr}\right)^{\frac{1}{1-n}}\left(\frac{1-n}{3-2n}\right)\left(\frac{h}{2}\right)^{\frac{3-2n}{1-n}} \tag{25}$$

By symmetry, we can express $$\left[\int_0^h u_r dz\right]$$

as:

$$\int_0^h u_r dz=\frac{-2}{\mu_0}\left(\frac{dP}{dr}\right)^{\frac{1}{1-n}}\left(\frac{1-n}{3-2n}\right)\left(\frac{h}{2}\right)^{\frac{3-2n}{1-n}} \tag{26}$$

$$\text{We set } \alpha(n)=2\left(\frac{1-n}{3-2n}\right)\left(\frac{h}{2}\right)^{\frac{3-2n}{1-n}}$$

and rewrite (Eq. (24)) as:

$$\alpha(n)\frac{1}{r}\frac{d}{dr}r\left(\frac{dP/dr}{\mu_0}\right)^{\frac{1}{1-n}}=U \tag{27}$$

After integrating (Eq. (27)) and applying boundary condition of P(0)→0 and P(0)=0, we obtain expression for pressure P as:

$$P=\frac{\mu_0}{2-n}\left(\frac{U}{2\alpha}\right)^{1-n}\left[r^{2-n}-R^{2-n}\right] \tag{28}$$

After we obtained the expression for P, we can then rewrite $u_r$ for $$z>\frac{h}{2}$$

as:

$$u_r=\left(\frac{Ur}{2\alpha}\right)\left(\frac{1-n}{2-n}\right)\left[\left(z-\frac{h}{2}\right)^{\frac{2-n}{1-n}}-\left(\frac{h}{2}\right)^{\frac{2-n}{1-n}}\right] \tag{29}$$

And $u_r$ for $$z<\frac{h}{2}$$

as:

$$u_r=\left(\frac{Ur}{2a}\right)\left(\frac{1-n}{2-n}\right)\left[\left(\frac{h}{2}-z\right)^{\frac{2-n}{1-n}}-\left(\frac{h}{2}\right)^{\frac{2-n}{1-n}}\right] \tag{30}$$

We can then solve for $u_z$ at $$z>\frac{h}{2}.$$

Using continuity equation, we can express $u_z$ as:

$$u_z=\int_{\frac{h}{2}}^{z}-\frac{1}{r}\left(\frac{\partial(ru_r)}{\partial r}\right)dz= \tag{31}$$

$$\int_{\frac{h}{2}}^{z}-\frac{1}{r}\left(\frac{\partial}{\partial r}\left(\frac{dP}{dr}\right)^{\frac{1}{1-n}}\left(\frac{1-n}{2-n}\right)r\right)\left[\left(z-\frac{h}{2}\right)^{\frac{2-n}{1-n}}-\left(\frac{h}{2}\right)^{\frac{2-n}{1-n}}\right]dz$$

For simplicity going forward, we set:

$$M(r)=-\frac{1}{r}\left(\frac{\partial}{\partial r}\left(\frac{dP}{dr}\right)^{\frac{1}{1-n}}\left(\frac{1-n}{2-n}\right)r\right)=-\left(\frac{1-n}{2-n}\right)\left[\frac{1}{1-n}\left(\frac{rU}{2\alpha}\right)^{n}+\frac{U}{2\alpha}\right] \tag{32}$$

We can proceed to solve for (Eq. (23)) and apply boundary condition $u_z(b)=U$ $$\frac{U}{M(r)}=\left(\frac{1-n}{3-2n}\left(\frac{h}{2}\right)^{\frac{3-2n}{1-n}}-\left(\frac{h}{2}\right)^{\frac{3-2n}{1-n}}+K_1\right) \tag{33}$$

We thus obtain $K_I$ as:

$$K_1 = \frac{U}{M(r)} - \frac{n-2}{3-2n}\left(\frac{h}{2}\right)^{\frac{3-2n}{1-n}} \tag{34}$$

We can then obtain $u_z$ at $$z > \frac{h}{2}$$

as:

$$u_z = M(r)\left[\left(\frac{1-n}{3-2n}\right)\left(z-\frac{h}{2}\right)^{\frac{3-2n}{1-n}} - \left(\frac{h}{2}\right)^{\frac{2-n}{1-n}}\left(z-\frac{h}{2}\right) + \frac{U}{M(r)} - \frac{n-2}{3-2n}\left(\frac{h}{2}\right)^{\frac{3-2n}{1-n}}\right] \tag{35}$$

Similarly we can obtain $u_z$ at $$z < \frac{h}{2}$$

with boundary condition as $u_z(0)=0$:

$$u_z = M(r)\left[\left(\frac{1-n}{3-2n}\right)\left(\frac{h}{2}-z\right)^{\frac{3-2n}{1-n}} - \left(\frac{h}{2}\right)^{\frac{2-n}{1-n}}\left(\frac{h}{2}-z\right) - \left(\frac{n-2}{3-2n}\right)\left(\frac{h}{2}\right)^{\frac{3-2n}{1-n}}\right] \tag{36}$$

Finally, we can solve for the Stefan force for a non-Newtonian fluid to be:

$$F_{stefan}^{non-Newtonian} = \int_0^R \frac{\mu_0}{2-n}\left(\frac{U}{2\alpha}\right)^{1-n}\left\{\frac{R^{4-n}}{4-n} - \frac{R^{4-n}}{2}\right\}2\pi r dr = -\frac{\mu_0 \pi}{4-n}\left(\frac{U}{2\alpha}\right)^{1-n} R^{4-n} \tag{37}$$

Rheological Characterization of Resins

In this example, two resins are used for printing: TMPTA+0.3 wt % BLS1326+2.5 wt % TPO and EPU 40 (Carbon Inc.). The rheological characterizations including flow sweep of the viscosity as a function of shear rate was performed. A parallel plate device with 25 mm diameter was used and approximately 250 μL of solution was employed for each experiment.

All rheological properties were characterized using ARES G2 (TA Instruments, New Castle, DE). Flow sweep of the TMPTA resin is done at temperature 20° C. for soak time 120 s, with shear rate sweeping from 0.01 to 100 (1/s). Flow sweep of the EPU 40 resin is done at temperature 20° C. for soak time 120 s, with shear rate sweeping from 0.01 to 1000 (1/s). Shear thinning is observed for both TMPTA and EPU 40 resins with different shear thinning coefficients of −0.87 and −0.72, indicating that both resins are non-Newtonian (FIGS. 19A-19B). Stress relaxation characterization of the TMPTA resin is done at temperature 20° C. for a soak time of 60 s, with stress relaxation duration 100s under strain % 500%. Stress relaxation characterization of the EPU 40 resin is done at temperature 20° C. for a soak time of 60 s, with stress relaxation duration 100s under strain % 500%. The longest relaxation time for TMPTA resin is characterized to be 112 ms, and the longest relaxation time for EPU 40 resin is characterized to be 221 ms (FIG. 19C).

Resin Stress Relaxation Time and Print Radius

Figures 21A, 21B, 21C, 21D, 21E, 21F:
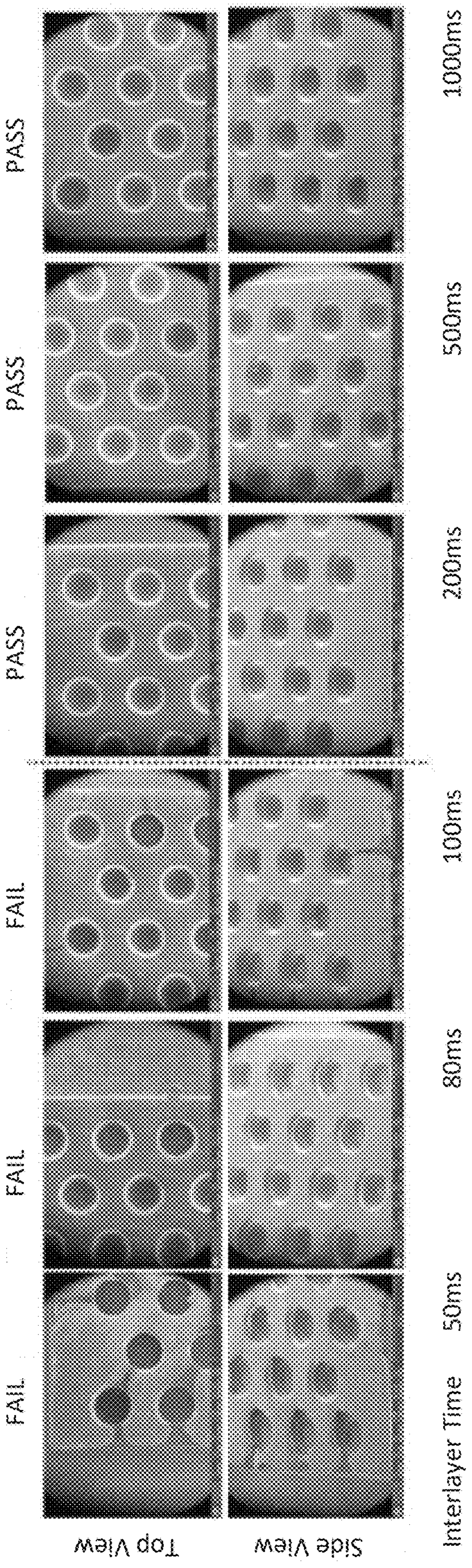
FIGS. 21A-21F depict the lateral print resolution and the impact of the interlayer time for resin reflow according to certain embodiments. Interlayer time (FIG. 21A) 50 ms, (FIG. 21B) 80 ms, (FIG. 21C) 100 ms, (FIG. 21D) 200 ms, (FIG. 21E) 500 ms (FIG. 21F) 1000 ms

The transient stress relaxation time required for resin (TMPTA+0.3 wt % BLS1326+2.5 wt % TPO) with print diameter ranging from 0.4 cm to 2.2 cm is plotted in FIG. 21A. The longest relaxation time is extracted by replotting FIG. 21A in semi-log plot to extract the average longest relaxation time t within the transient stress-relaxation process. It is found that the stress-relaxation time increases with increased diameter. There is an effect of resin shrinkage during curing has a potential impact on the stress-relaxation. However, from FIGS. 20A-2B within the 100 ms during exposure time, there's no observable relaxation occurring.

Resin Re-Flow and Print Defects Under Insufficient Interlayer Time

Based on our prediction on the required time for resin to reflow for the 8.9 mm by 5.6 mm square area for a resin (TMPTA+0.3 wt % BLS1326+2.5 wt % TPO) with viscosity approximately 0.2 PaS at shear rate of 0.1 (1/s), we have conducted a characterization of the defect versus the interlayer time. The measured interlayer time showed that the defect is gone after approximately at >200 ms (FIG. 20).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112(f) or 35 U.S.C. § 112(6) is not invoked.

What is claimed is:

1. A polymeric microneedle comprising a lattice microstructure having one or more lattice cell units;

wherein the microneedle comprises a gradient in the lattice cell units such that the density of lattice cell units increases across a longitudinal axis of the microneedle.

2. The microneedle according to claim 1, wherein the microneedle comprises 2 or more repeating lattice cell units.

3. The microneedle according to claim 1, wherein the lattice cell unit comprises a lattice shape selected from the group consisting of tetrahedral, Kagome, rhombic, icosahedral, Voronoi and triangular.

4. The microneedle according to claim 1, wherein the microneedle comprises lattice cell units having a size of from 200 μm to 500 μm.

5. The microneedle according to claim 1, wherein the lattice microstructure comprises a plurality of struts.

6. The microneedle according to claim 1, wherein the microneedle comprises:

a tip section comprising a solid structure;

a body section comprising a lattice structure; and a base section comprising a solid structure.

7. The microneedle according to claim 1, wherein the lattice structure is formed from polyethylene glycol dimethacrylate (PEGDMA).

8. A patch comprising:

a backing layer; and a plurality of polymeric microneedles in contact with the backing layer, wherein each microneedle comprises a lattice microstructure having one or more lattice cell units;

wherein the microneedle comprises a gradient in the lattice cell units such that the density of lattice cell units increases across a longitudinal axis of the microneedle.

9. The patch according to claim 8, wherein one or more of the microneedles further comprise an active agent compound.

10. A method comprising applying to a skin surface of a subject a patch according to claim 1.

11. A method of making a polymeric microneedle comprising a lattice microstructure having one or more lattice cell units, the method comprising:

a) irradiating a polymerizable composition positioned between a build elevator and a build surface to generate a polymerizable composition comprising a first polymerized region of the polymerizable composition in contact with the build elevator and a first non-polymerized region of the polymerizable composition in contact with the build surface;

b) displacing the build elevator away from the build surface;

c) irradiating the first non-polymerized region of the polymerizable composition to generate a second polymerized region of the polymerizable composition in contact with the first polymerized region and a second non-polymerized region in contact with the build surface; and d) repeating steps a)-c) in a manner sufficient to generate a microneedle comprising a lattice microstructure.

12. The method according to claim 11, wherein the polymerizable composition is irradiated with a micro-digital light projection system comprising:

a light beam generator component comprising:

a light source;

a tube lens; and one or more projection lenses; and a light projection monitoring component comprising charge-coupled device (CCD).

13. The method according to claim 11, wherein the micro-digital light projection system provides for a lattice microstructure resolution of from 1.5 μm to 3.8 μm.

14. A system for making a polymeric microneedle comprising a lattice microstructure having one or more lattice cell units, the system comprising:

a micro-digital light projection system comprising:

a light beam generator component; and a light projection monitoring component;

a liquid interface polymerization module comprising a build elevator and a build surface configured for generating the microneedle from a polymerizable composition positioned therebetween; and a processor comprising memory operably coupled to the processor wherein the memory comprises instructions stored thereon, which when executed by the processor, cause the processor to:

a) irradiate a polymerizable composition positioned between a build elevator and a build surface to generate a polymerizable composition comprising a first polymerized region of the polymerizable composition in contact with the build elevator and a first non-polymerized region of the polymerizable composition in contact with the build surface;

b) displace the build elevator away from the build surface;

c) irradiate the first non-polymerized region of the polymerizable composition to generate a second polymerized region of the polymerizable composition in contact with the first polymerized region and a second non-polymerized region in contact with the build surface; and d) repeat steps a)-c) in a manner sufficient to generate the polymeric microneedle comprising a lattice microstructure.

* * * * *